(12) United States Patent
Honjo et al.

(10) Patent No.: US 11,662,339 B1
(45) Date of Patent: May 30, 2023

(54) EFFICACY DETERMINATION MARKERS IN DISEASE TREATMENT BY PD-1 SIGNAL INHIBITOR

(71) Applicant: Kyoto University, Kyoto (JP)

(72) Inventors: Tasuku Honjo, Kyoto (JP); Kenji Chamoto, Kyoto (JP); Fumihiko Matsuda, Kyoto (JP); Yasushi Okuno, Kyoto (JP); Sidonia Fagarasan, Saitama (JP)

(73) Assignee: Kyoto University, Kyoto (JP)

( * ) Notice: Subject to any disclaimer, the term of this patent is extended or adjusted under 35 U.S.C. 154(b) by 716 days.

(21) Appl. No.: 16/346,566

(22) PCT Filed: Nov. 1, 2017

(86) PCT No.: PCT/JP2017/039619
§ 371 (c)(1),
(2) Date: May 1, 2019

(87) PCT Pub. No.: WO2018/084204
PCT Pub. Date: May 11, 2018

(30) Foreign Application Priority Data

Nov. 2, 2016 (JP) .............................. JP2016-214785
Aug. 4, 2017 (JP) .............................. JP2017-151547

(51) Int. Cl.
*A61K 39/395* (2006.01)
*G01N 33/49* (2006.01)
(Continued)

(52) U.S. Cl.
CPC ............ *G01N 33/492* (2013.01); *A61P 31/00* (2018.01); *A61P 35/00* (2018.01); *A61P 37/04* (2018.01);
(Continued)

(58) Field of Classification Search
None
See application file for complete search history.

(56) References Cited

U.S. PATENT DOCUMENTS

2017/0114137 A1* 4/2017 Li .................... A61K 39/39558

FOREIGN PATENT DOCUMENTS

| CN | 103536915 A | 1/2014 |
| JP | 2016-064989 A | 4/2016 |
| WO | 2016/012615 A1 | 1/2016 |

OTHER PUBLICATIONS

Raedler et al., Opdivo (Nivolumab): Second PD-1 Inhibitor Receives FDA Approval for Unresectable or Metastatic Melanoma, American Health & Drug Benefits, Mar. 2015, vol. 8, pp. 180-183. (Year: 2015).*

(Continued)

*Primary Examiner* — Claire Kaufman
(74) *Attorney, Agent, or Firm* — Morgan, Lewis & Bockius LLP

(57) ABSTRACT

The present invention provides markers for judging the efficacy of therapy with a PD-1 signal inhibitor before or at an early stage of the therapy. As biomarkers for predicting or judging the efficacy of therapy with a PD-1 signal inhibitor, surrogate indicators of metabolic changes relating to mitochondrial activity in T cells and/or T cell activation in a subject are used. As such indicators, intestinal flora-related metabolites in the serum or plasma, energy metabolism-related metabolites in the serum or plasma, amino acid metabolism-related metabolites and/or derivatives thereof in the serum of plasma, oxygen consumption rate and/or ATP turnover in peripheral blood $CD8^+$ cells, amino acids in T cells, and T-bet in peripheral blood $CD8^+$ cells may be used.

18 Claims, 15 Drawing Sheets

(51) Int. Cl.
    *A61P 35/00*     (2006.01)
    *A61P 37/04*     (2006.01)
    *C07K 16/28*     (2006.01)
    *G01N 33/50*     (2006.01)
    *A61P 31/00*     (2006.01)
    *G01N 33/68*     (2006.01)

(52) U.S. Cl.
    CPC ...... *C07K 16/2818* (2013.01); *C07K 16/2827* (2013.01); *G01N 33/5011* (2013.01); *G01N 33/6872* (2013.01); *G01N 2800/52* (2013.01); *G01N 2800/7028* (2013.01)

(56) References Cited

OTHER PUBLICATIONS

Hamanishi, Junzo, PD-1 signal inhibitors: Future perspectives and Issues, Annals of Onocology 27, Supplemental 7. Jul. 2016 (Year: 2016).*

Li et al., PD-1/SHP-2 Inhibits Tc1/Th1 Phenotypic Responses and the Activation of T Cells in the Tumor Microenvironment, Canc. Res. 75(3):508-518, Feb. 2015.*

Tkachev et al., Programmed death-1 controls T cell survival by regulating oxidative metabolism, J. Immunol. 194(12):5789-5800, Jun. 2015.*

Patsoukis et al., PD-1 alters T-cell metabolic reprogramming by inhibiting glycolysis and promoting lipolysis and fatty acid oxidation, Nat. Commun. 6:6692, DOI: 10.1038/ncomms7692, Mar. 26, 2015.*

Wang, Intestinal microbiota-associated metabolites: crucial factors in the effectiveness of herbal medicines and diet therapies, Front . Physiol. 10:1343, doi: 10.3389/fphys.2019.01343, Oct. 2019.*

Lee et al., Reinvigorating exhausted T cells by blockade of the PD-1 pathway, Immunopathol. Dis. Therap. 6(1-2): 7-17, 2015.*

Berrien-Elliott et al., Checkpoint blockade immunotherapy relies on T-bet but not Eomes to induce effector function in tumor-inflitrating CD8+ T cells, Canc. Immunol. Res. 3(2):116-124, Feb. 2015.*

Chamoto et al.,Mitochondrial activation chemicals synergize with surface receptor PD-1 blockade for T cell-dependent antitumor activity, Proc. Natl. Acad. Sci., doi/10.1073/pnas.16204331114, E761-E770, Jan. 12, 2017.*

Schönrich et al., The PD-1/PD-L1 Axis and Virus Infections: A Delicate Balance, Front. Cell Infect. Microbiol. 9:207, doi: 10.3389/fcimb.2019.00207, Jun. 13, 2019.*

Routy et al., Gut microbiome influences efficacy of PD-1-based immunotherapy against epithelial tumors, Science, 359(6371):91-97, doi: 10.1126/science.aan3706, Epub Nov. 2, 2017, Jan. 8, 2018.*

Yamauchi et al., A High Serum Uric Acid Level Is Associated with Poor Prognosis in Patients with Acute Myeloid Leukemia, Anticanc. Res. 33:3947-3952, 2013.*

Chen et al., Characteristic biosignature for discrimination of gastric cancer from healthy population by high throughput GC-MS analysis, Oncotarget, 7(52):87496-87510, 2016.*

Stotz et al., Evaluation of Uric Acid as a Prognostic Blood-Based Marker in a Large Cohort of Pancreatic Cancer Patients, PLoS One 9(8): e104730. doi:10.1371/journal.pone.0104730, 2014.*

Partial European Search Report issued in corresponding European Patent Application No. 17867434.7 dated Mar. 11, 2020.

Meng et al., "Predictive biomarkers in PD-1/PD-L1 checkpoint blockade immunotherapy," Cancer Treatment Reviews, 41 (10): 868-876 (2015).

Topalian et al., "Mechanism-driven biomarkers to guide immune checkpoint blockade in cancer therapy," Nature Reviews: Cancer, 16 (5): 275-287 (2016).

Inoue et al., "Intratumoral expression levels of PD-L1, GZMA, and HLA-A along with oligoclonal T cell expansion associate with response to nivolumab in metastatic melanoma," Oncoimmunology, 5 (9): e1204507 (2016).

Holmes et al., "Understanding the role of gut microbiome-host metabolic signal disruption in health and disease," Trends in Microbiology, 19 (7): 349-359 (2011).

Qin et al., "The Diverse Function of PD-1/PD-L Pathway Beyond Cancer," Frontiers in Immunology, 10: 2298 (2019).

Patel et al., "PD-L1 Expression as a Predictive Biomarker in Cancer Immunotherapy," Molecule Cancer Therapeutics, 14 (4): 847-856 (2015).

Tumeh et al., "PD-1 blockade induces responses by inhibiting adaptive immune resistance," Nature, 515 (7528): 568-571 (2014).

Bengsch et al., "Bioenergetic Insufficiencies Due to Metabolic Alterations Regulated by the Inhibitory Receptor PD-1 Are an Early Driver of CD8+ T Cell Exhaustion," Immunity, 45: 358-373 (2016).

Scharping et al., "THe Tumor Microenvironment Represses T cell Mitochondrial Biogenesis to Drive Intratumoral T cell Metabolic Insufficiency and Dysfunction," Immunity, 45: 374-388 (2016).

International Search Report issued in corresponding International Patent Application No. PCT/JP2017/039619 dated Jan. 30, 2018.

Office Action issued in corresponding Chinese Patent Application No. 201780066425.4 dated Oct. 8, 2022.

* cited by examiner

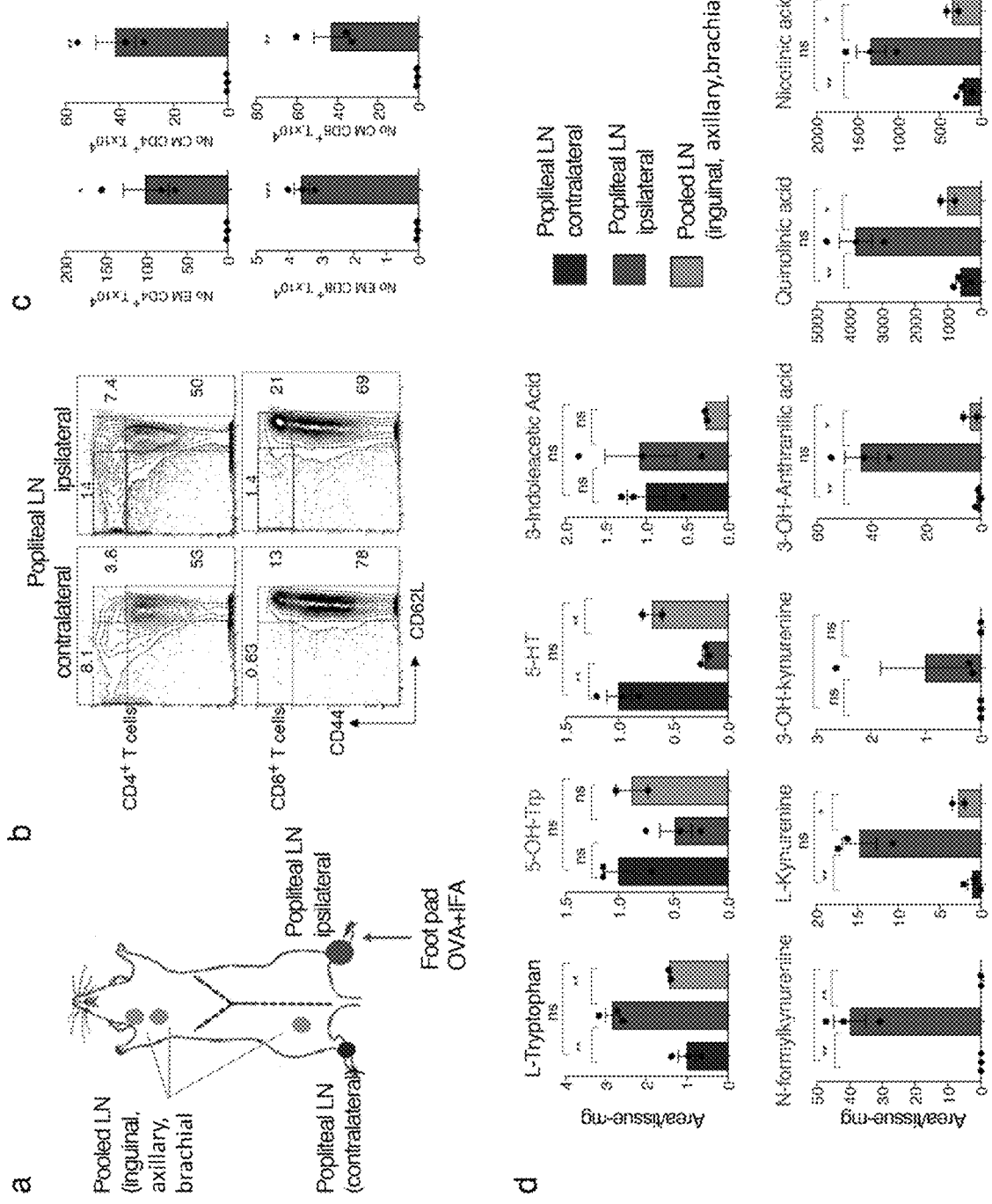

| Metabolites | P-value |
|---|---|
| 2weeks after 1st Nivolumab | |
| Gluconic acid | 0.0037 |
| Cystine | 0.0101 |
| Thyroxine | 0.0127 |
| Indoxyl sulfate | 0.0428 |
| 3-Methyl-2-oxobutyric acid | 0.0015 |
| Nicotinamide | 0.0294 |
| 2-Aminoethanol | 0.0356 |
| Lactic acid | 0.0429 |

| Metabolites | P-value |
|---|---|
| Pre-treatment | |
| Hippurate | 0.0101 |
| Indoxyl sulfate | 0.0499 |
| Uric acid | 0.0356 |
| Aminoadipic acid | 0.0101 |
| 2weeks after 1st Nivolumab | |
| Gluconic acid | 0.0037 |
| Cystine | 0.0101 |
| Thyroxine | 0.0127 |
| Indoxyl sulfate | 0.0428 |
| 3-Methyl-2-oxobutyric acid | 0.0015 |
| Nicotinamide | 0.0294 |
| 2-Aminoethanol | 0.0356 |
| Lactic acid | 0.0429 |

| Metabolites | P-value |
|---|---|
| 4weeks after 1st Nivolumab | |
| Ornithine | 0.0089 |
| Cystine | 0.0499 |
| 4-Cresol | 0.0258 |
| Decanoic acid | 0.0499 |
| Pyruvic acid | 0.0090 |
| 2-Hydroxybutyric acid | 0.0111 |
| 2-Oxoglutaric acid | 0.0249 |
| Pyroglutamic acid | 0.0299 |
| Lactic acid | 0.0169 |

EFFICACY DETERMINATION MARKERS IN DISEASE TREATMENT BY PD-1 SIGNAL INHIBITOR

TECHNICAL FIELD

The present invention relates to markers for judging the efficacy of disease therapies with PD-1 signal inhibitors.

BACKGROUND ART

The results of recent clinical trials have revealed that the anti-PD-1 antibody therapy is more effective than conventional standard therapies in various cancers (Non-Patent Documents Nos. 1-3). The response rate of PD-1 antibody therapy was 20-30% when used alone and 60-70% when combined with other therapies, showing a dramatic improvement compared to conventional immunotherapies. However, about one half of the patients were non-responsive. Little is known about why those patients are non-responsive to the PD-1 antibody therapy.

PRIOR ART LITERATURE

Non-Patent Documents

Non-Patent Document No. 1: Borghaei H, Paz-Ares L, Horn L, et al: Nivolumab versus Docetaxel in Advanced Non-squamous Non-Small-Cell Lung Cancer. N Engl J Med, 373:1627-1639, 2015

Non-Patent Document No. 2: Hamanishi J, Mandai M, Ikeda T, et al: Safety and Antitumor Activity of Anti-PD-1 Antibody, Nivolumab, in Patients with Platinum-Resistant Ovarian Cancer. J Clin Oncol, 2015

Non-Patent Document No. 3: Motzer R J, Escudier B, McDermott D F, et al: Nivolumab versus Everolimus in Advanced Renal-Cell Carcinoma. N Engl J Med, 373: 1803-1813, 2015

DISCLOSURE OF THE INVENTION

Problem for Solution by the Invention

It is an object of the present invention to provide markers for judging efficacy prior to or at an early stage of disease therapy with a PD-1 signal inhibitor.

Means to Solve the Problem

The present inventors have measured blood metabolites in mice treated with PD-1 blockade antibody and found that tricarboxylic acid (TCA) cycle-related metabolites in the serum were significantly reduced in treated mouse group compared to non-treated mouse group. This is consistent with the finding that TCA cycle-related metabolites are reduced in PD-1 knockout (PD-$1^{-/-}$) mice. Therefore, it is believed that the efficacy of PD-1 antibody therapy (i.e., whether the administration of PD-1 antibody inhibits the tumor growth or not) can be judged by measuring the absolute levels of these TCA cycle-related metabolites and compared the changes in these metabolites before and after administration of PD-1 antibody.

Using PD-1 antibody-administered mice, the present inventors have also found that oxygen consumption rate (OCR) and ATP turnover calculated therefrom in killer T cells are higher in PD-1 blockade treated group than untreated group for cancers sensitive to the PD-1 inhibitory antibody therapy, but this not the case for non-sensitive cancers. This suggests that OCR and ATP turnover could serve as biomarkers for predicting the efficacy of the PD-1 blockade therapy.

Further, the present inventors have found that the expression of T-bet in killer T cells increases after administration of anti-PD-L1 antibody in the treated mice with cancer sensitive to the PD-1 inhibitory antibody therapy. This suggests that increase in T-bet expression could also be one of the biomarkers.

Further, the present inventors have confirmed that the concentrations of amino acid metabolism-related metabolites and derivatives thereof in the serum or plasma and uptake of amino acids into T cells could also serve as indicators of T cell activation during the PD-1 blockade therapy.

For exertion of anti-tumor immunity by PD-1 blockade, T cell activation is necessary, and what have been described above can be indicators of T cell activation. Further, using plasma samples from cancer patients, the present inventors have confirmed that levels of metabolites relating to intestinal flora that regulates T cell activation capacity and energy metabolism-related metabolites as an indicator of T cell activation could also be served as markers for judging the efficacy of PD-1 inhibitory antibody therapy.

Intestinal flora is already known to be responsible for regulating T cell activation capacity and, from the above-described finding, the present inventors have noted that the T cell-mediated anti-tumor immunological competence through the PD-1 blockade therapy can be predicted by examining intestinal flora-related metabolism. While therapeutic effect is believed to be high in those patients whose T cells have been activated as a result of inhibition of PD-1 signal, it is believed that oxygen consumption and ATP turnover in mitochondria, T-bet, intestinal flora-related metabolites, amino acids, amino acid metabolism-related metabolites and derivatives thereof, as well as energy metabolism (including TCA cycle)-related metabolites can be indicators of T cell activation.

A summary of the present invention is described as below.

(1) A test method comprising predicting or judging the therapeutic efficacy with a PD-1 signal inhibitor based on metabolic changes relating to mitochondrial activity in T cells and/or T cell activation in a subject.

(2) A method of using a surrogate indicator of metabolic changes relating to mitochondrial activity in T cells and/or T cell activation in a subject as a biomarker for predicting or judging the efficacy of therapy with a PD-1 signal inhibitor.

(3) A method of diagnosis and therapy for a disease, comprising predicting or judging the therapeutic efficacy with a PD-1 signal inhibitor based on metabolic changes relating to mitochondrial activity in T cells and/or T cell activation in a subject, and administering to the subject in a therapeutically effective amount when the therapy with the PD-1 signal inhibitor has been predicted or judged effective.

(4) The method according to any one of (1) to (3) above, wherein at least one member selected from the following (i) to (vi) is used as an indicator of metabolic changes relating to mitochondrial activity in T cells and/or T cell activation in a subject:

(i) intestinal flora-related metabolites in the serum or plasma, (ii) energy metabolism-related metabolites in the serum or plasma, (iii) amino acid metabolism-related metabolites and/or derivatives thereof in the serum or plasma,
(iv) oxygen consumption rate and/or ATP turnover in peripheral blood CD8$^+$ cells,
(v) amino acids in T cells, and
(vi) T-bet expression in peripheral blood CD8$^+$ cells.
(5) The method according to any one of (1) to (4) above, wherein the PD-1 signal inhibitor is an antibody.
(6) The method according to (5) above, wherein the antibody is at least one antibody selected from the group consisting of anti-PD-1 antibody, anti-PD-L1 antibody and anti-PD-L2 antibody.
(7) The method according to any one of (1) to (6) above, wherein the PD-1 signal inhibitor is used as an active ingredient of an anticancer agent, an anti-infective agent or a combination thereof
(8) A pharmaceutical composition comprising a PD-1 signal inhibitor as an active ingredient, which is for use in a method of diagnosis and therapy for a disease, comprising predicting or judging the therapeutic efficacy with a PD-1 signal inhibitor based on metabolic changes relating to mitochondrial activity in T cells and/or T cell activation in a subject, and administering to the subject the PD-1 signal inhibitor in a therapeutically effective amount when the therapy with the PD-1 signal inhibitor has been predicted or judged effective.
(9) The pharmaceutical composition according to (8) above, wherein at least one member selected from the following (i) to (vi) is used as an indicator of metabolic changes relating to mitochondrial activity in T cells and/or T cell activation in a subject:
(i) intestinal flora-related metabolites in the serum or plasma,
(ii) energy metabolism-related metabolites in the serum or plasma,
(iii) amino acid metabolism-related metabolites and/or derivatives thereof in the serum or plasma,
(iv) oxygen consumption rate and/or ATP turnover in peripheral blood CD8$^+$ cells, (v) amino acids in T cells, and
(vi) T-bet expression in peripheral blood CD8$^+$ cells.

Effect of the Invention

Since the therapy using anti-PD-1 antibody, a representative of PD-1 signal inhibitors, is very expensive, judging the efficacy prior to or at an early stage of such therapy will lead to reduction of the cost of the treatment.

The present specification encompasses the contents disclosed in the specifications and/or drawings of Japanese Patent Application Nos. 2016-214785 and 2017-151547 based on which the present patent application claims priority.

BEST MODES FOR CARRYING OUT THE INVENTION

Figure 1:
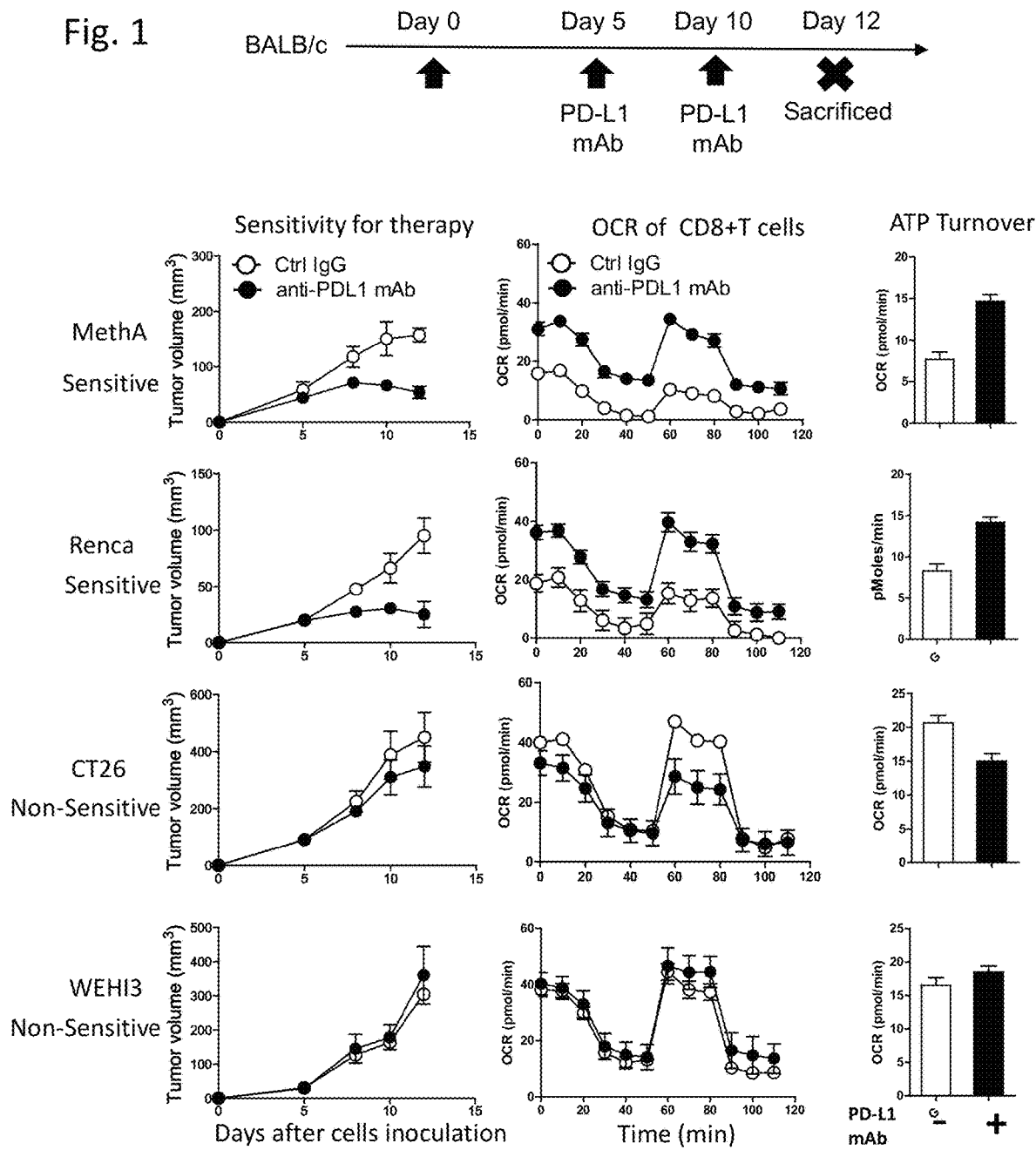
FIG. 1 Tumors sensitive to the PD-1 blockade therapy and tumors non-sensitive thereto were inoculated into BALB/c mice, which were then subjected to the PD-1 blockade therapy. CD8$^+$ T cells were isolated from draining lymph nodes (DLNs) at day 12 postinoculation, followed by examination of oxygen consumption rate (OCR) and ATP turnover.

Hereinbelow, the present invention will be described in detail.

The present invention provides a test method comprising predicting or judging the efficacy of therapy with a PD-1 signal inhibitor based on metabolic changes relating to mitochondrial activity in T cells and/or T cell activation in a subject.

A surrogate indicator of metabolic changes relating to mitochondrial activity in T cells and/or T cell activation may be used as a biomarker for predicting or judging the efficacy of therapy with a PD-1 signal inhibitor.

When the PD-1 blockade therapy are estimated effective by the marker based on metabolic changes relating to mitochondrial activity in T cells and/or T cell activation in a subject, the PD-1 signal inhibitor may be administered to the subject in a therapeutically effective amount.

Surrogate indicators of metabolic changes relating to mitochondrial activity in T cells and/or T cell activation in a subject include, but are not limited to, oxygen consumption rate and/or ATP turnover (especially in peripheral blood $CD8^+$ cells), T-bet (especially in peripheral blood $CD8^+$ cells), intestinal flora-related metabolites (especially in the serum or plasma), energy metabolism-related metabolites (especially in the serum or plasma), amino acid metabolism-related metabolites and derivatives thereof (especially in the serum or plasma), as well as amino acids (especially in T cells). Energy metabolism-related metabolites include, but are not limited to, TCA cycle-related metabolites, glycolytic pathway-related metabolites, oxidative phosphorylation-related metabolites, lipid metabolism-related metabolites, and the pentose phosphate cycle. Amino acids are also included in the amino acid metabolism-related metabolites.

A surrogate indicator of metabolic changes relating to mitochondrial activity in T cells and/or T cell activation in a subject may be measured before administration of a PD-1 signal inhibitor to predict the effect thereof. Alternatively, such a surrogate indicator may be measured before and after administration of a PD-1 signal inhibitor to judge the effect thereof.

In one embodiment of the present invention, OCR and/or ATP turnover in the peripheral blood $CD8^+$ cells of a subject is measured before administration of a PD-1 signal inhibitor; and if the level is high, it is predicted that therapy with the PD-1 inhibitor would be effective. Alternatively, OCR and/or ATP turnover in peripheral blood $CD8^+$ cells of a subject before and after administration of a PD-1 inhibitor is measured; and if the OCR and/or ATP turnover after administration of the PD-1 inhibitor is higher than that before administration, therapy with the PD-1 inhibitor is judged to be effective. If the level of OCR and/or ATP turnover in peripheral blood $CD8^+$ cells in responders is higher than non-responders to the PD-1 inhibitor, their levels (values) may be defined as "high". If a cut-off value can be set, a greater value than that may be regarded as "high" level.

Peripheral blood $CD8^+$ cells may be collected as described below. Briefly, a blood sample collected from a patient is overlayered on Ficoll and centrifuged at 2000 rpm. The resultant buffy coat between an erythrocyte layer and a plasma layer is recovered and washed in a cell culture medium. $CD8^+$ T cells are isolated from the resultant lymphocytes using a magnetic cell separator (Miltenyi Biotec).

Oxygen consumption rate (OCR) may be measured with XF96 Extracellular Flux analyzer (Seahorse Biosciences). Isolated $CD8^+$ T cells are seeded in a dedicated cell culture plate, which is then covered with a sensor cartridge. Oligomycin, FCCP, antimycin A and rotenone were injected into the injection ports of the sensor cartridge. The plate and the cartridge are mounted in the analyzer. Oxygen concentration and hydrogen ion concentration in the semi-closed microenvironment between cells and the sensor are measured.

ATP turnover may be calculated as described below.

ATP turnover=(OCR immediately before administration of oligomycin)−(OCR immediately after administration of oligomycin)

In the present invention, OCR and/or ATP turnover in peripheral blood $CD8^+$ cells may be used as a biomarker for predicting or judging the efficacy of therapy with a PD-1 signal inhibitor.

OCR and/or ATP turnover in peripheral blood $CD8^+$ cells of a subject before administration of a PD-1 inhibitor may be measured; and if the level is high, the PD-1 signal inhibitor may be administered to the subject in a therapeutically effective amount. Alternatively, OCR and/or ATP turnover in peripheral blood $CD8^+$ cells of a subject before and after administration of a PD-1 inhibitor may be measured; and if the OCR and/or ATP turnover after administration is higher than that before administration, the PD-1 inhibitor may be further administered to the subject in a therapeutically effective amount.

In another embodiment of the present invention, expression of T-bet in peripheral blood $CD8^+$ cells in a subject before administration of the PD-1 signal inhibitor is measured; and if the level is high, it is assumed that therapy with the PD-1 signal inhibitor would be effective. Alternatively, expression of T-bet in peripheral blood $CD8^+$ cells in a subject before and after administration of the PD-1 signal inhibitor is measured; and if the expression of T-bet after administration is higher than that of before administration, it suggests that therapy with the PD-1 signal inhibitor would be effective. The expression level of T-bet in peripheral blood $CD8^+$ cells in a subject may be considered to be "high" if the levels of the responders are higher than the non-responders to the PD-1 signal inhibitor. If a cut-off value can be set, a greater value than that may be regarded as "high" level.

T-bet is a transcription factor which is required for increasing the cytotoxic activity or IFN-γ production of killer T ($CD8^+$ T) cells.

Expression of T-bet may be measured as described below. After staining a cell surface marker such as CD8, CD44 or CD62L, cells are fixed and permeabilized. Then, the inside of cell nuclei was stained with an anti-T-bet antibody. After the staining, flow cytometry analysis is performed.

In the present invention, T-bet in peripheral blood $CD8^+$ cells may be used as a biomarker for predicting or judging the efficacy of therapy with a PD-1 signal inhibitor.

Expression of T-bet in peripheral blood $CD8^+$ cells derived from a subject before administration of a PD-1 signal inhibitor may be measured; and if the expression level is high, the PD-1 signal inhibitor may be administered to the subject in a therapeutically effective amount. Alternatively, expression of T-bet in peripheral blood $CD8^+$ cells from a subject before and after administration of a PD-1 signal inhibitor may be measured; and if expression of T-bet in peripheral blood $CD8^+$ cells after administration of the PD-1 inhibitor is higher than the level before administration, the PD-1 inhibitor may be further administered to the subject in a therapeutically effective amount.

Further, in another embodiment of the present invention, the level (concentration) of an intestinal flora-related metabolite in the serum or plasma derived from a subject before the administration of a PD-1 signal inhibitor may be measured; and if the level (concentration) is high or low (depending on the items), it is assumed that the therapy with the PD-1 signal inhibitor would be effective. Alternatively, the level (concentration) of an intestinal flora-related metabolite in the serum or plasma derived from a subject before and after administration of a PD-1 signal inhibitor is measured; and if the level (concentration) of the metabolite after administration has altered from the level before administration, it is judged that therapy with the PD-1 signal inhibitor is effective. The level (concentration) of an intestinal flora-related metabolite in the serum or plasma derived from a subject may be considered to be "high" or "low" if the level of responders is higher or lower than the non-responders. If a cut-off value can be set, a value above or below it may be regarded as "high" or "low".

It is known that intestinal flora is an important factor which regulates T cell-mediated immunoreactions. Therefore, intestinal flora is one of those factors which affect the therapeutic effect after PD-1 inhibitory antibody therapy. Several bacterial species in the intestinal flora are known to be involved in T cell activation and metabolites produced by these bacterial species can be detected by examining related metabolites in the blood.

As intestinal flora-related metabolites, either one metabolite or a combination of two or more metabolites may be measured.

Intestinal flora-related metabolites may be measured by mass spectrometry (e.g., GC-MS or LCMS).

In the present invention, an intestinal flora-related metabolite in the serum or plasma may be used as a biomarker for predicting or judging the efficacy of therapy with a PD-1 signal inhibitor.

The level (concentration) of an intestinal flora-related metabolite in the serum or plasma derived from a subject before administration of a PD-1 signal inhibitor may be measured; and if the level is high or low, the PD-1 signal inhibitor may be administered to the subject in a therapeutically effective amount. Alternatively, the level (concentration) of an intestinal flora-related metabolite in the serum or plasma in a subject before and after administration of a PD-1 signal inhibitor may be measured; and if the level (concentration) of the intestinal flora-related metabolite in the serum or plasma after administration of the PD-1 signal inhibitor has altered from the level before administration, the PD-1 signal inhibitor may be further administered to the subject in a therapeutically effective amount.

Still further, in another embodiment of the present invention, the level (concentration) of an energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) in the serum or plasma derived from a subject before administration of a PD-1 signal inhibitor is measured; and if the level (concentration) is high or low, it is predicted that therapy with the PD-1 signal inhibitor would be effective. Alternatively, the level (concentration) of an energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) in the serum or plasma derived from a subject before and after administration of a PD-1 signal inhibitor is measured; and if the level (concentration) of the energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) after administration of the PD-1 signal inhibitor has altered from the level before administration, it is judged that the therapy with the PD-1 signal inhibitor is effective. The level (concentration) of an energy metabolism-related metabolite may be defined as "high" or "low" if the level of responders is higher or lower than non-responders to the PD-1 signal inhibitor. If a cut-off value can be set, a value above or below it may be regarded as "high" or "low".

The TCA cycle is a metabolic pathway in which the acetyl group in acetyl-CoA is completely oxidized into $CO_2$ and $H_2O$. Examples of TCA cycle-related metabolites include, but are not limited to, oxaloacetic acid, citric acid, cis-aconitic acid, isocitric acid, oxalosuccinic acid, 2-oxoglutaric acid, succinyl-CoA, succinic acid, fumaric acid, L-malic acid and oxaloacetic acid.

The glycolytic pathway governs the production of those metabolites which are fed into the TCA cycle. Since part of the glycolytic pathway is also incorporated in the pentose phosphate cycle necessary for nucleic acid synthesis, the glycolytic pathway is critical for cell division and activation.

Oxidative phosphorylation is an essential pathway for energy production and is the substantial part of the electron transport chain.

Fatty acid oxidation is a pathway through which fats and lipids are degraded. The degraded fats and lipids are fed into the TCA cycle as acetyl CoA and used as energy sources.

The pentose phosphate cycle is a pathway which produces not only components necessary for nucleic acid synthesis but also reducing agents.

As energy metabolism-related metabolites, either one metabolite or a combination of two or more metabolites may be measured.

Energy metabolism-related metabolites may be measured by mass spectrometry (e.g., GC-MS or LCMS).

In the present invention, energy metabolism-related metabolites (such as TCA cycle-related metabolites, glycolytic pathway-related metabolites, oxidative phosphorylation-related metabolites, lipid metabolism-related metabolites, or pentose phosphate cycle-related metabolites) in the serum or plasma may be used as biomarkers for predicting or judging the efficacy of therapy with a PD-1 signal inhibitor.

The level (concentration) of an energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) in the serum or plasma derived from a subject before administration of a PD-1 signal inhibitor may be measured; and if the level is low or high, the PD-1 signal inhibitor may be administered to the subject in a therapeutically effective amount. Alternatively, the level (concentration) of an energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) in the serum or plasma derived from a subject before and after administration of a PD-1 signal inhibitor may be measured; and if the level (concentration) of the energy metabolism-related metabolite (such as TCA cycle-related metabolites, glycolytic pathway-related metabolites, oxidative phosphorylation-related metabolites, lipid metabolism-related metabolites, or pentose phosphate cycle-related metabolites) in the serum or plasma after administration of the PD-1 signal inhibitor has altered from the level before administration, the PD-1 signal inhibitor may be further administered to the subject in a therapeutically effective amount.

In another embodiment of the present invention, the level (concentration) of an amino acid metabolism-related metabolite and/or a derivative thereof in the serum or plasma derived from a subject before administration of a PD-1 signal inhibitor is measured; and if the level is low or high, it is predicted that therapy with the PD-1 signal inhibitor will be effective. Alternatively, the level (concentration) of an amino acid metabolism-related metabolite and/or a derivative thereof in the serum or plasma derived from a subject before and after administration of a PD-1 signal inhibitor is measured; and if the level (concentration) of the amino acid metabolism-related metabolite and/or a derivative thereof in the serum or plasma after administration of the PD-1 signal inhibitor has altered from the level before administration, it is judged that therapy with the PD-1 signal inhibitor is effective. The level (concentration) of an amino acid metabolism-related metabolite and/or a derivative thereof in the serum or plasma derived from a subject may be considered to be "low" or "high" if the level is different from the corresponding level for non-responders to the PD-1 signal inhibitor. If a cut-off value can be set, a value above and below may be regarded as "high" or "low".

Specific examples of amino acid include, but are not limited to, tryptophan, phenylalanine, leucine, isoleucine, tyrosine, histidine, lysine, methionine, threonine, valine, alanine, arginine, asparagine, aspartic acid, cysteine, glutamic acid, glutamine, glycine, proline, serine, ornithine, citrulline and analogues thereof. The amino acid may be either one amino acid or a combination of two or more amino acids. The amino acid may be L-amino acid.

Amino acids are components that constitute cytoskeletons when T cells are activated, and are essential for T cell activation. Amino acids are also produced from intestinal bacteria. Amino acid metabolism not only enters the TCA cycle and produces energy ultimately, but changes into neurotransmitters and plays an important role in controlling biorhythms in the human body.

A derivative of amino acid metabolism-related metabolite means a substance generated from an amino acid metabolism-related metabolite in vivo.

As amino acid metabolism-related metabolites and/or derivatives thereof, either one or a combination of two or more may be measured.

Amino acid metabolism-related metabolites and/or derivatives thereof may be measured by mass spectrometry (e.g., GC-MS or LC-MS).

In the present invention, an amino acid metabolism-related metabolite and/or a derivative thereof in the serum or plasma may be used as a biomarker for predicting or judging the efficacy of therapy with a PD-1 signal inhibitor.

The level (concentration) of an amino acid metabolism-related metabolite and/or a derivative thereof in the serum or plasma derived from a subject before administration of a PD-1 signal inhibitor may be measured; and if the level is low or high, the PD-1 signal inhibitor may be administered to the subject in a therapeutically effective amount. Alternatively, the level (concentration) of an amino acid metabolism-related metabolite and/or a derivative thereof in the serum or plasma derived from a subject before and after administration of a PD-1 signal inhibitor may be measured; and if the level (concentration) after administration of the PD-1 signal inhibitor has altered from the level before administration, the PD-1 signal inhibitor may be further administered to the subject in a therapeutically effective amount.

Further, in another embodiment of the present invention, the level (concentration) of an amino acid in T cells derived from a subject before administration of a PD-1 signal inhibitor is measured; and if the level is high, it is predicted that therapy with the PD-1 signal inhibitor will be effective. Alternatively, the level (concentration) of an amino acid in T cells derived from a subject before and after administration of a PD-1 signal inhibitor is measured; and if the level (concentration) of the amino acid after administration of the PD-1 signal inhibitor has risen compared to the level before administration, it is judged that therapy with the PD-1 signal inhibitor is effective. The level (concentration) of an amino acid in T cells derived from a subject may be considered to be "high" if the level is higher than the corresponding level for non-responders to the PD-1 signal inhibitor. If a cut-off value can be set, a value higher than that may be regarded as "high".

T cells may be collected as described below. Briefly, a blood sample collected from a patient is overlayered on Ficoll and centrifuged at 2000 rpm. The resultant buffy coat between an erythrocyte layer and a plasma layer is recovered and washed in a cell culture medium. T cells are isolated from the resultant lymphocytes using a magnetic cell separator (Miltenyi Biotec) system.

Specific examples of amino acid include, but are not limited to, tryptophan, phenylalanine, leucine, isoleucine, tyrosine, histidine, lysine, methionine, threonine, valine, alanine, arginine, asparagine, aspartic acid, cysteine, glutamic acid, glutamine, glycine, proline, serine, ornithine, citrulline and analogues thereof. As amino acids, either one amino acid or a combination of two or more amino acids may be measured. Amino acids may be L-amino acids.

Amino acids may be measured by imaging mass spectrometry (such as MALDI-MS) or mass spectrometry (e.g., GC-MS or LC-MS).

In the present invention, an amino acid in T cells may be used as a biomarker for predicting or judging the efficacy of therapy with a PD-1 signal inhibitor.

The level (concentration) of an amino acid in T cells derived from a subject before administration of a PD-1 signal inhibitor may be measured; and if the level is high, the PD-1 signal inhibitor may be administered to the subject in a therapeutically effective amount. Alternatively, the level (concentration) of an amino acid in T cells derived from a subject before and after administration of a PD-1 signal inhibitor may be measured; and if the level after administration of PD-1 signal inhibitor has risen compared to the level before administration, the PD-1 signal inhibitor may be further administered to the subject in a therapeutically effective amount.

In examples described later, the following substances were measured as intestinal flora-related metabolites, energy metabolism-related metabolites, and amino acid metabolism-related metabolites and derivatives thereof: phenol, lactic acid, 2-hydroxyisobutyric acid, caproic acid, glycolic acid, oxalic acid, 2-hydroxybutyric acid, 4-cresol, 3-hydroxybutyric acid, 3-hydroxyisobutyric acid, 2-hydroxyisovaleric acid, 2-aminobutyric acid, 3-hydroxyisovaleric acid, valine, octanoic acid, glycerol, phosphoric acid, proline, succinic acid, glyceric acid, fumaric acid, serine, threonine, decanoic acid, aspartic acid, methionine, lauric acid, citric acid, myristic acid, palmitoleic acid, palmitic acid, margaric acid, stearic acid, pyruvic acid, 2-oxoisocaproic acid, 2-aminoethanol, malic acid, thereitol, erythritol, threonic acid, 2-oxoglutaric acid, pyrophosphate, arabitol, fucose, isocitric acid, hypoxanthine, ornithine, 1,5-anhydro-D-sorbitol, fructose, mannose, lysine, glucose, scyllo-inositol, myo-inositol, oleic acid, sucrose, indoxyl sulfate, 3-methyl-2-oxobutyric acid, maltose, gluconic acid, ribitol, glycine, benzoic acid, 3-methyl-2-oxovaleric acid, linoleic acid, hypotaurine, elaidic acid, quinolinic acid, nicotinamide, kynurenine, kynurenic acid, indoleacetate, indolelactate, 5-OH-Trp (5-hydroxy-tryptophan), 5-HIAA (5-hydroxyindole acetic acid), 3-OH-kynurenine, 3-OH-anthralinic acid, 3-indolepropionate, serotonin, tryptophan, N'-formylkynurenine, tyrosine, histidine, adenosine, guanosine, inosine, uridine, xanthosine, GSSG (glutathione-S-S-glutathione), GSH (glutathione-SH), AC_C0 (carnitine), aminoadipic acid, choline, AC_C6 (hexanoylcarnitine), AC_C5 (valerylcarnitine), AC_C2 (acetylcarnitine), 3-methylhistidine, phenylalanine, cysteine, arginine, glutamine, glutamic acid, alanine, citruline, creatinine, pyroglutamic acid, taurine, asparagine, cystine, cystathionine, isoleucine, leucine, creatine, asy-dimethylarginine, sym-dimethylarginine, 2-aminoisobutyric acid, thyroxine, hippurate, citric acid, isocitric acid, succinic acid, 2-hydroxybutyric acid, 3-hydroxybutyric acid, lactic acid, 2-hydroxyglutaric acid, 2-hydroxyisovaleric acid, 3-hydroxyisovaleric acid, glyceric acid, malic acid, betaine, urea, uric acid, acetylglycine and 4-hydroxyproline.

As used herein, the term "PD-1 signal" refers to the signal transduction mechanism which PD-1 bears. As one aspect of this mechanism, PD-1 inhibits T cell activation in collaboration with its ligands PD-L1 and PD-L2. PD-1 (Programmed cell death-1) is a membrane protein expressed in activated T cells and B cells. Its ligands PD-L1 and PD-L2 are expressed in various cells such as antigen-presenting cells (monocytes, dendritic cells, etc.) and cancer cells. PD-1, PD-L1 and PD-L2 work as inhibitory factors which inhibit T cell activation. Certain types of cancer cells and virus-infected cells escape from host immune surveillance by expressing the ligands of PD-1 to thereby inhibit T cell activation.

As PD-1 signal inhibitors, substances which specifically bind to PD-1, PD-L1 or PD-L2 may be given. Such substances include, but are not limited to, proteins, polypeptides, oligopeptides, nucleic acids (including natural-type and artificial nucleic acids), low molecular weight organic compounds, inorganic compounds, cell extracts, and extracts from animals, plants, soils or the like. These substances may be either natural or synthetic products. Preferable PD-1 signal inhibitors are antibodies. More preferably, antibodies such as anti-PD-1 antibody, anti-PD-L1 antibody and anti-PD-L2 antibody may be given. Any type of antibody may be used as long as it is capable of inhibiting PD-1 signal. The antibody may be any of polyclonal antibody, monoclonal antibody, chimeric antibody, single chain antibody, humanized antibody or human-type antibody. Methods for preparing such antibodies are known. The antibody may be derived from any organisms such as human, mouse, rat, rabbit, goat or guinea pig. As used herein, the term "antibody" is a concept encompassing antibodies of smaller molecular sizes such as Fab, F(ab)'$_2$, ScFv, Diabody, V$_H$, V$_L$, Sc(Fv)$_2$, Bispecific sc(Fv)$_2$, Minibody, scFv-Fc monomer or scFv-Fc dimer.

PD-1 signal inhibitors may be used as active ingredients in anticancer agents, anti-infective agents or combinations thereof.

The present invention also provides a pharmaceutical composition comprising a PD-1 signal inhibitor as an active ingredient, which is used for a method of diagnosis and therapy for a disease, comprising predicting or judging the therapeutic efficacy of a PD-1 signal inhibitor based on metabolic changes relating to mitochondrial activity in T cells and/or T cell activation in a subject, and administering the PD-1 signal inhibitor to the subject in a therapeutically effective amount when the metabolic markers indicate the PD-1 blockade therapy would be effective.

For indicators of metabolic changes relating to mitochondrial activity in T cells and/or T cell activation in a subject, reference should be had to the foregoing description.

One embodiment of the present invention provides a pharmaceutical composition comprising a PD-1 signal inhibitor as an active ingredient, which is for use in a method of therapy for a disease, comprising measuring OCR and/or ATP turnover in peripheral blood CD8+ cells derived from a subject before administration of a PD-1 signal inhibitor and, if the level is high, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring OCR and/or ATP turnover in peripheral blood CD8+ cells derived from a subject before and after administration of a PD-1 signal inhibitor and further administering to the subject the PD-1 signal inhibitor in a therapeutically effective amount if the OCR and/or ATP turnover in peripheral blood CD8+ cells after administration has risen compared to the level before administration.

Further, another embodiment of the present invention provides a pharmaceutical composition comprising a PD-1 signal inhibitor as an active ingredient, which is for use in a method of therapy for a disease, comprising measuring expression of T-bet in peripheral blood CD8+ cells in a subject before administration of PD-1 signal inhibitor and, if the level is high, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring expression of T-bet in peripheral blood CD8+ cells derived from a subject before and after administration of PD-1 signal inhibitor and further administering the PD-1 signal inhibitor to the subject in a therapeutically effective amount if the expression of T-bet in peripheral blood CD8+ cells after administration of the PD-1 signal inhibitor has risen compared to the expression before administration.

Further, still another embodiment of the present invention provides a pharmaceutical composition comprising a PD-1 signal inhibitor as an active ingredient, which is for use in a method of therapy for a disease, comprising measuring an intestinal flora-related metabolite in the serum or plasma derived from a subject before administration of a PD-1 signal inhibitor and, if the value is high or low, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring an intestinal flora-related metabolite in the serum or plasma derived from a subject before and after administration of a PD-1 signal inhibitor and further administering the PD-1 signal inhibitor to the subject in a therapeutically effective amount if the intestinal flora-related metabolite in the serum or plasma after administration of the PD-1 signal inhibitor has altered compared to the value before administration.

Further, still another embodiment of the present invention provides a pharmaceutical composition comprising a PD-1 signal inhibitor as an active ingredient, which is for use in a method of therapy for a disease, comprising measuring an energy metabolism-related metabolite in the serum or plasma derived from a subject before administration of a PD-1 signal inhibitor and, if the value is high or low, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring an energy metabolism-related metabolite in the serum or plasma derived from a subject before and after administration of a PD-1 signal inhibitor and further administering the PD-1 signal inhibitor to the subject in a therapeutically effective amount if the energy metabolism-related metabolite in the serum or plasma after administration of the PD-1 signal inhibitor has altered compared to the value before administration.

Another embodiment of the present invention provides a pharmaceutical composition comprising a PD-1 signal inhibitor as an active ingredient, which is for use in a method of therapy for a disease, comprising measuring the level (concentration) of an amino acid metabolism-related metabolite and/or a derivative thereof in the serum or plasma derived from a subject before administration of a PD-1 signal inhibitor and, if the level is high or low, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring the level (concentration) of an amino acid metabolism-related metabolite and/or a derivative thereof in the serum or plasma derived from a subject before and after administration of a PD-1 signal inhibitor and further administering the PD-1 signal inhibitor to the subject in a therapeutically effective amount if the level (concentration) of the amino acid metabolism-related metabolite after administration of the PD-1 signal inhibitor has altered compared to the level before administration.

Further, another embodiment of the present invention provides a pharmaceutical composition comprising a PD-1 signal inhibitor as an active ingredient, which is for use in a method of therapy for a disease, comprising measuring the level (concentration) of an amino acid in T cells derived from a subject before administration of a PD-1 signal inhibitor and, if the level is high, administering the PD-1 signal inhibitor to the subject in a therapeutically effective amount. Alternatively, the present invention provides a pharmaceutical composition comprising a PD-1 signal inhibitor as an active ingredient, which is for use in a method of therapy for a disease, comprising measuring the level (concentration) of an amino acid in T cells derived from a subject before and after administration of a PD-1 signal inhibitor and further administering the PD-1 signal inhibitor to the subject in a therapeutically effective amount if the level (concentration) of the amino acid after administration of the PD-1 signal inhibitor has risen compared to the level before administration.

The pharmaceutical composition of the present invention may be used as an anticancer agent, an anti-infective agent or a combination thereof.

When the pharmaceutical composition of the present invention is administered as an anticancer agent, target cancers or tumors includes, but are not limited to, leukemia, lymphoma (e.g., Hodgkin's disease, non-Hodgkin's lymphoma), multiple myeloma, brain tumors, breast cancer, endometrial cancer, cervical cancer, ovarian cancer, esophageal cancer, stomach cancer, appendix cancer, colon cancer, liver cancer, gallbladder cancer, bile duct cancer, pancreatic cancer, adrenal cancer, gastrointestinal stromal tumor, mesothelioma, head and neck cancer (such as laryngeal cancer), oral cancer (such as floor of mouth cancer), gingival cancer, tongue cancer, buccal mucosa cancer, salivary gland cancer, nasal sinus cancer (e.g., maxillary sinus cancer, frontal sinus cancer, ethmoid sinus cancer, sphenoid sinus cancer), thyroid cancer, renal cancer, lung cancer, osteosarcoma, prostate cancer, testicular tumor (testicular cancer), renal cell carcinoma, bladder cancer, rhabdomyosarcoma, skin cancer (e.g., basal cell cancer, squamous cell carcinoma, malignant melanoma, actinic keratosis, Bowen's disease, Paget's disease) and anal cancer.

When the pharmaceutical composition of the present invention is administered as an anti-infective agent, target infections include, but are not limited to, bacterial infections [various infections caused by *Streptococcus* (e.g., group A β hemolytic *streptococcus*, pneumococcus), *Staphylococcus aureus* (e.g., MSSA, MRSA), *Staphylococcus epidermidis, Enterococcus, Listeria, Neisseria* meningitis aureus, *Neisseria gonorrhoeae*, pathogenic *Escherichia coli* (e.g., 0157: H7), *Klebsiella* (*Klebsiella pneumoniae*), *Proteus, Bordetella pertussis, Pseudomonas aeruginosa, Serratia, Citrobacter, Acinetobacter, Enterobacter, mycoplasma, Clostridium* or the like; tuberculosis, cholera, plague, diphtheria, dysentery, scarlet fever, anthrax, syphilis, tetanus, leprosy, *Legionella* pneumonia (legionellosis), leptospirosis, Lyme disease, tularemia, Q fever, and the like], rickettsial infections (e.g., epidemic typhus, scrub typhus, Japanese spotted fever), chlamydial infections (e.g., trachoma, genital chlamydial infection, psittacosis), fungal infections (e.g., aspergillosis, candidiasis, cryptococcosis, trichophytosis, histoplasmosis, *Pneumocystis* pneumonia), parasitic protozoan infections (e.g., amoebic dysentery, malaria, toxoplasmosis, leishmaniasis, cryptosporidiosis), parasitic helminthic infections (e.g., echinococcosis, schistosomiasis *japonica*, filariasis, ascariasis, diphyllobothriasis *latum*), and viral infections [e.g., influenza, viral hepatitis, viral meningitis, acquired immune deficiency syndrome (AIDS), adult T-cell leukemia, Ebola hemorrhagic fever, yellow fever, cold syndrome, rabies, cytomegalovirus infection, severe acute respiratory syndrome (SARS), progressive multifocal leukoencephalopathy, chickenpox, herpes zoster, hand-foot-and-mouth disease, dengue, erythema infectiosum, infectious mononucleosis, smallpox, rubella, acute anterior poliomyelitis (polio), measles, pharyngoconjunctival fever (pool fever), Marburg hemorrhagic fever, hantavirus renal hemorrhagic fever, Lassa fever, mumps, West Nile fever, herpangina and chikungunya fever].

The pharmaceutical composition of the present invention is administered to human or animal subjects systemically or locally by an oral or parenteral route.

PD-1 signal inhibitors (e.g., anti-PD-1 antibody, anti-PD-L1 antibody or anti-PD-L2 antibody) may be dissolved in buffers such as PBS, physiological saline or sterile water, optionally filter- or otherwise sterilized before being administered to human or animal subjects by injection or infusion. To the solution of PD-1 signal inhibitors, additives such as coloring agents, emulsifiers, suspending agents, surfactants, solubilizers, stabilizers, preservatives, antioxidants, buffers, isotonizing agents and the like may be added. As routes of administration, intravenous, intramuscular, intraperitoneal, subcutaneous or intradermal administration and the like may be selected.

The content of the PD-1 signal inhibitor (e.g., anti-PD-1 antibody, anti-PD-L1 antibody or anti-PD-L2 antibody) in a preparation varies with the type of the preparation and is usually 1-100% by weight, preferably 50-100% by weight. Such a preparation may be formulated into a unit dosage form.

The dose, frequency and number of administration of PD-1 signal inhibitor (e.g., anti-PD-1 antibody, anti-PD-L1 antibody or anti-PD-L2 antibody) may vary with the symptoms, age and body weight of the human or animal subject, the method of administration, dosage form and more. For example, in terms of the amount of the active ingredient usually ranges from 0.1 to 100 mg/kg body weight, preferably 1-10 mg/kg body weight, and may be administered once per adult at a frequency that enables confirmation of efficacy. The efficacy of therapy with a PD-1 signal inhibitor is predicted or judged based on metabolic changes relating to mitochondrial activity in T cells and/or T cell activation in the subject and when the therapy with a PD-1 signal inhibitor is predicted or judged effective, it may be administered to the subject in a therapeutically effective amount. For indicators of metabolic changes relating to mitochondrial activity in T cells and/or T cell activation in a subject, reference should be had to the foregoing description.

EXAMPLES

Hereinbelow, the present invention will be described more specifically with reference to the following Examples.

Example 1

Various types of tumors were inoculated into BALB/c mice (Charles River Laboratories Japan): Meth A (Cell Resource Center for Biomedical Research) and RENCA (American Type Culture Collection), both of which are sensitive to PD-1 inhibitory antibody therapy, and CT26 (American Type Culture Collection) and WEHI (American Type Culture Collection), both of which are non-sensitive to PD-1 inhibitory antibody therapy. At day 5 post tumor inoculation, a PD-L1 antibody (1-111A; prepared in the present inventors' laboratory; 150 µg/ml) was administered to the mice, followed by the $2^{nd}$ administration after a further 5 days. At day 2 after the $2^{nd}$ administration, $CD8^+$ T cells in draining lymph nodes were isolated, and mitochondrial oxygen consumption rate was measured with XF96 Extracellular Flux analyzer (Seahorse Biosciences). Based on the results obtained, ATP turnover was calculated. The results are shown in FIG. 1.

MC38 (Dr. Jim Allison), sensitive to PD-1 inhibitory antibody therapy, and LLC (American Type Culture Collection), non-sensitive to PD-1 inhibitory antibody therapy, were inoculated into C57BL/6N mice (Charles River Laboratories Japan). At day 5 post tumor inoculation, a PD-L1 antibody (1-111A; prepared in the present inventors' laboratory; 150 µg/ml) was administered to the mice, followed by the $2^{nd}$ administration after 5 days. At day 2 after the $2^{nd}$ administration, $CD8^+$ T cells in draining lymph nodes were isolated, and mitochondrial oxygen consumption rate was measured with XF96 Extracellular Flux analyzer (Seahorse Biosciences). Based on the results obtained, ATP turnover was calculated. The results are shown in FIG. 2.

Figure 2:
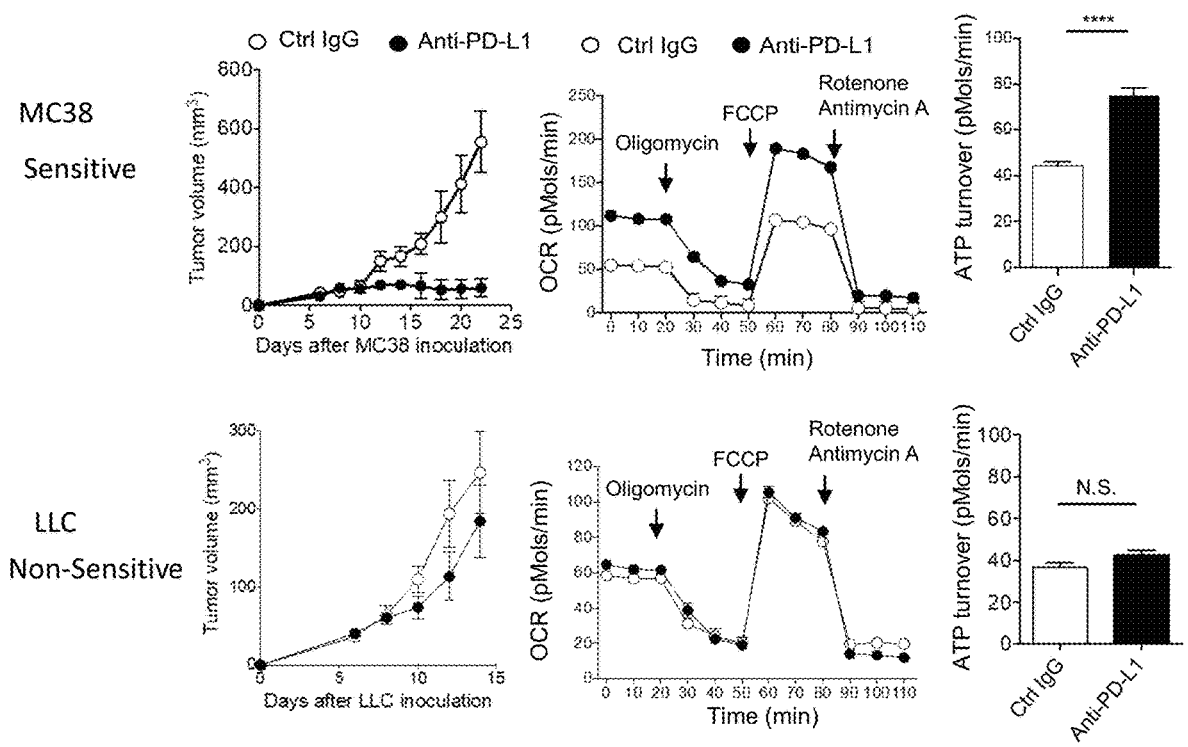
FIG. 2 A tumor sensitive to the PD-1 blockade therapy and a tumor non-sensitive thereto were inoculated into C57BL/6 mice, which were then subjected to PD-1 blockade therapy. CD8$^+$ T cells were isolated from draining lymph nodes (DLNs) at day 12 postinoculation, followed by examination of oxygen consumption rate (OCR) and ATP turnover.

The results of FIGS. 1 and 2 revealed that the percent increase in OCR following administration of PD-L1 antibody was greater when highly sensitive tumors were treated. This suggests that the percent increase in mitochondrial oxygen consumption rate in the peripheral blood of a patient before and immediately after treatment could serve as a biomarker for predicting efficacy.

Example 2

Figure 3:
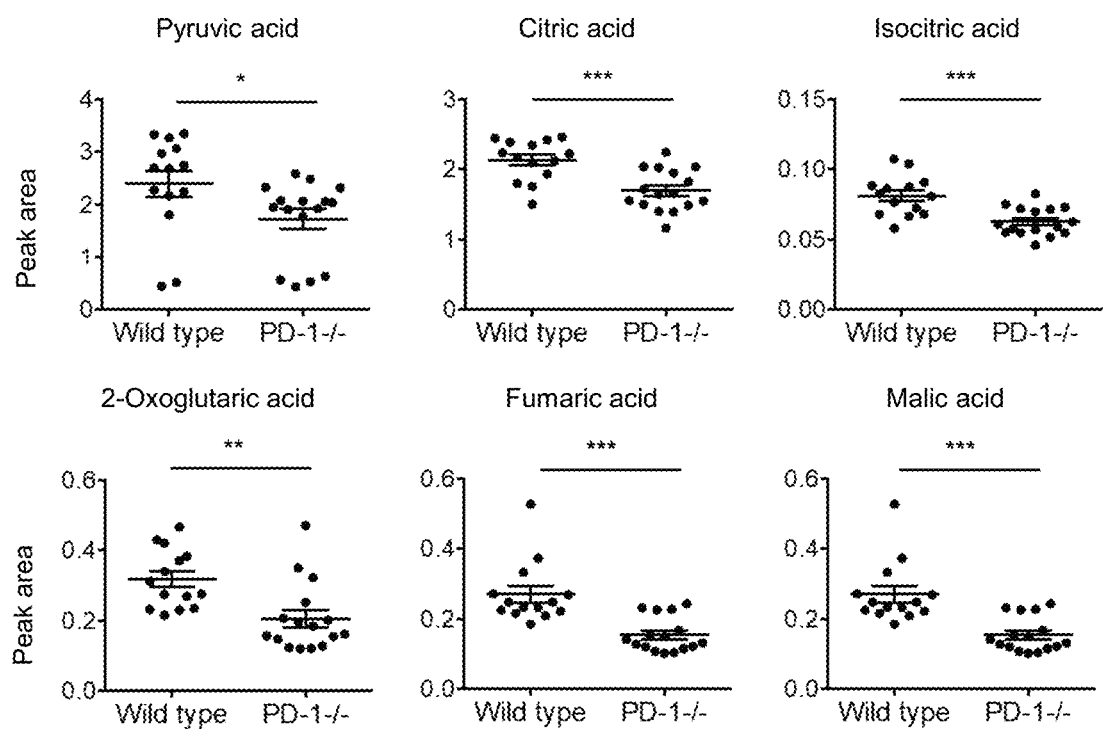
FIG. 3 Metabolite levels in the sera of wild-type mice and PD-1$^{-/-}$ mice were measured by gas-chromatography-mass spectrometry (GC-MS). TCA cycle-related metabolites were extracted.

Serum samples collected from wild-type C57BL/6N mice (Charles River Laboratories Japan) and $PD^{-/-}$ mice (Immunity 11, 141-151 (1999); Science 291, 319-322 (2001); Nat. Med. 9, 1477-1483 (2003)) were extracted with a mixed solution of methanol, chloroform and water to produce methoxyamine derivatives. After separation of metabolites using a methylpolysiloxane nonpolar column, concentrations of TCA cycle-related metabolites were measured by mass spectrometry. TCA cycle-related metabolites in the serum showed a tendency to decrease in $PD^{-/-}$ mice. The results are shown in FIG. 3.

Figure 4:
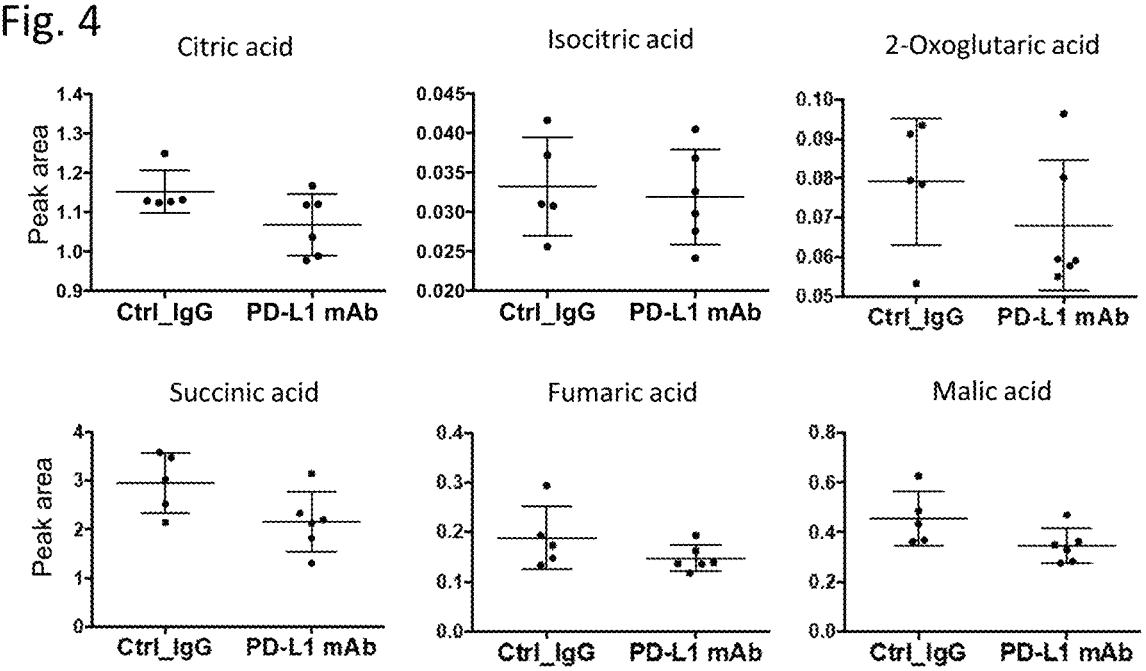
FIG. 4 MC38 was inoculated to C57BL/6 mice, and PD-L1 antibody was administered intraperitoneally at day 5 and 10 postinoculation. Sera were collected from mice at day 13 postinoculation, followed by measurement of metabolites in the same manner as in FIG. 3.

PD-L1 antibody (1-111A; prepared in the present inventors' laboratory; 200 µg) or control IgG (Bio X Cell) was administered to C57BL/6N mice three times at 1-day intervals. Then, concentrations of TCA cycle-related metabolites in the serum were measured by GC-MS. The results are shown in FIG. 4. When PD-L1 antibody was administered, TCA cycle-related metabolites in the serum showed a tendency to decrease. This is likely caused by the mitochondrial activation of CD8+ T cells (killer T cells) and subsequent consumption of blood metabolites.

In view of the above results, it is believed that if $CD8^+$ T cells are activated above a cancer rejecting threshold by administration of PD-1 inhibitory antibody to a cancer-bearing subject, mitochondria of the $CD8^+$ T cells are activated and the cells consumes blood metabolites, reducing their levels. On the other hand, in the case of a cancer that provides so strong immunosuppression which prevents rejection following administration of PD-1 inhibitory antibody, CD8+ T cells cannot be activated and there is no decrease in blood metabolites. Therefore, blood metabolites serve as an indicator of mitochondrial activation (i.e., activation of killer T cells) and may probably be used as biomarkers for predicting the efficacy of PD-1 blockade.

Example 3

Mitochondrial activation is correlated with cellular activation. mTOR signal plays an important role in cellular activation. It is known that the mTOR pathway also activates mitochondria and simultaneously activates T-bet, a transcription factor important for Th1 immunity. The present inventors therefore compared T-bet activity before and after treatment, using CD8+ T cells obtained in Example 1.

Figure 5:
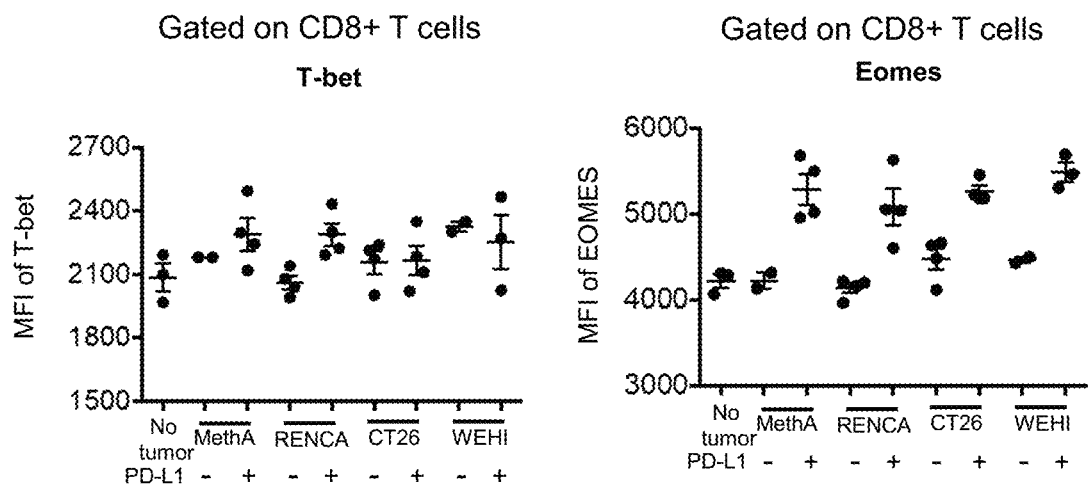
FIG. 5 MethA, RENCA, CT26 or WEHI was inoculated to BALB/c mice, and PD-L1 antibody was administered intraperitoneally at day 5 and 10 postinoculation. DLNs were isolated from mice at day 12 postinoculation. The DLN cells were stained for T-bet and Eomes. Then, fluorescence intensities (MFI) were compared by gating on CD8$^+$ T cells.

The draining lymph node cells used in Example 1 were stained with anti-CD8 antibody (BioLegend), anti-T-bet antibody (BioLegend) and anti-EOMES antibody (eBioscience). After gating on CD8+ T cells, expressions of T-bet and EOMES were compared before and after administration of PD-L1 antibody. The results are shown in FIG. 5.

As predicted, expression of T-bet increased after administration of the antibody in the treatment of highly sensitive cancers. On the other hand, expression of EOMES increased regardless of whether the cancer being treated was sensitive or non-sensitive. These results indicate that CD8+ T cells are activated (likely via mTOR) against sensitive cancers, leading to the increase in mitochondrial OCR. Further, these results also indicate that the rise in T-bet expression can serve as one of the biomarkers for this metabolic change.

Example 4

Figure 6:
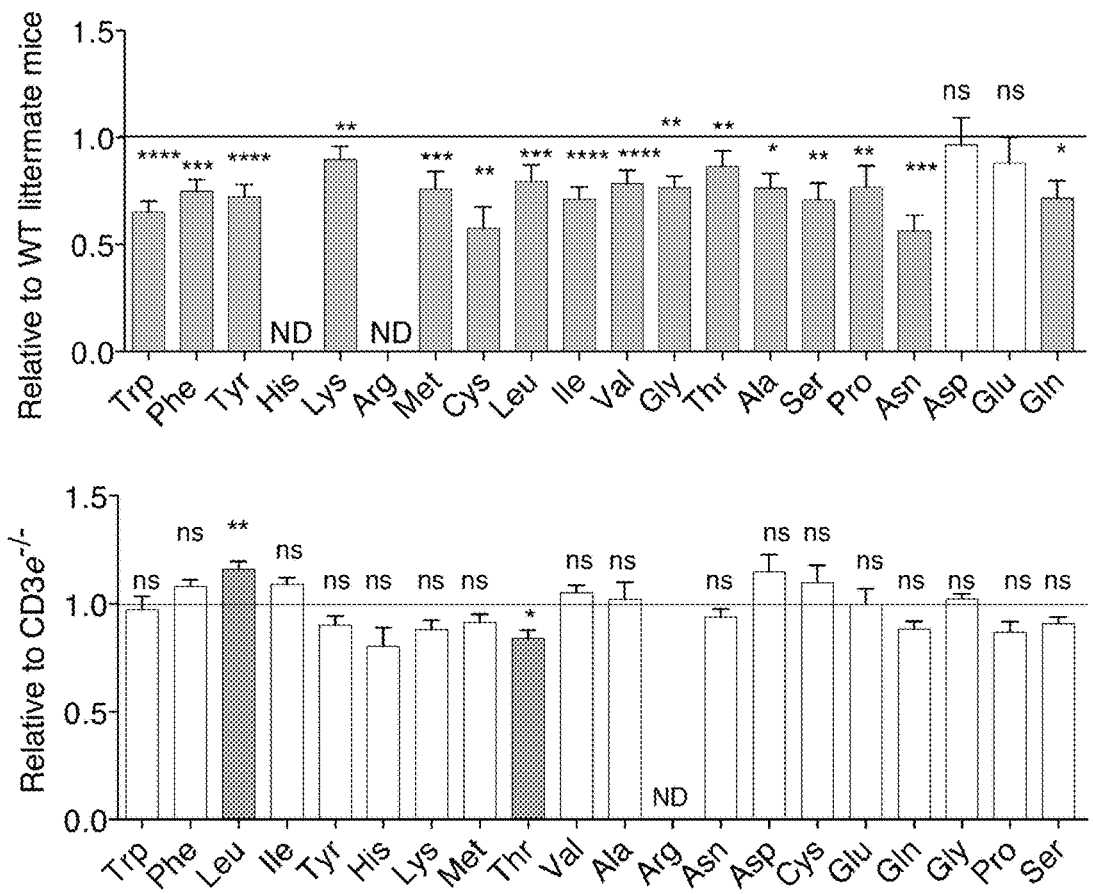
FIG. 6 Blood amino acid levels are decreased in a T cell dependent manner in a state of PD-1 signal blockade. When blood amino acid levels in PD-1$^{-/-}$ mice were compared with those levels in wild-type mice by GC-MS analysis, the blood amino acid levels in PD-1$^{-/-}$ mice were lower (upper graph). No remarkable difference was observed when blood amino acid levels were compared between CD3$^{-/-}$ mice and PD1$^{-/-}$ CD3$^{-/-}$ mice. From these results, it was assumed that consumption of blood amino acids was occurring in PD-1$^{-/-}$ mice due to constitutive activation of T cells. n=5 mice/group (upper graph), n=11 (lower graph). Two tailed unpaired Student's t-test; ns, not significant, *p<0.05, p<0.005, *p<0.0005, ****p<0.0001.
Figure 7:
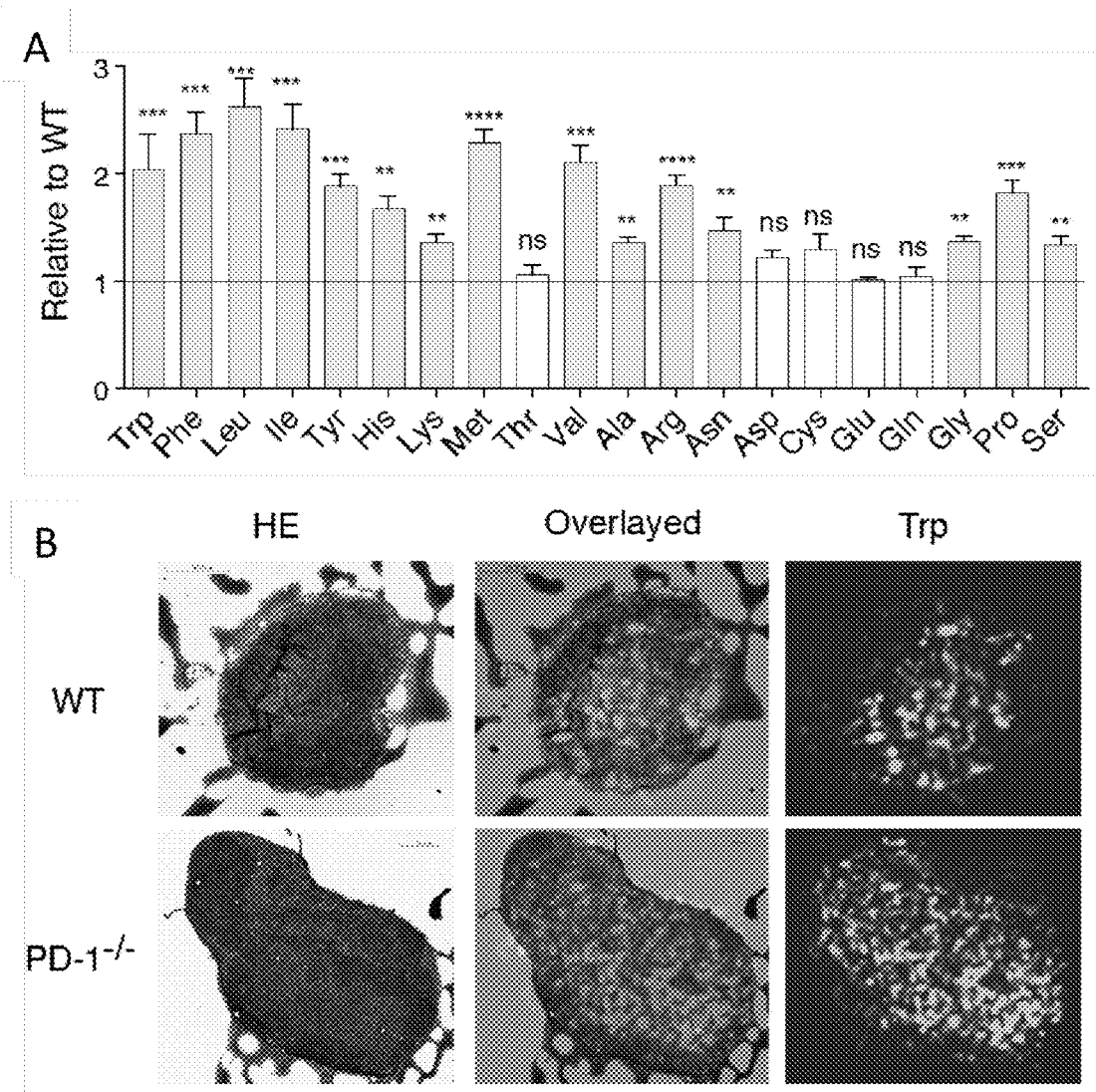
FIG. 7 Amino acids are taken up into T cells by the activation during PD-1 blockade. A) Intracellular amino acid levels in lymph nodes of PD-1$^{-/-}$ mice and wild-type mice were measured and compared. As it turned out, amino acid levels in PD-1$^{-/-}$ mice were higher than those in wild-type mice. Data show values±SEM. n=5 mice/group. Two tailed unpaired Student's t-test; ns, not significant, *p<0.05, p<0.005, *p<0.0005, ****p<0.0001. B) Distributions of tryptophan (Trp) in wild-type (WT) and PD1$^{-/-}$ mice lymph nodes are shown.
Figure 8:
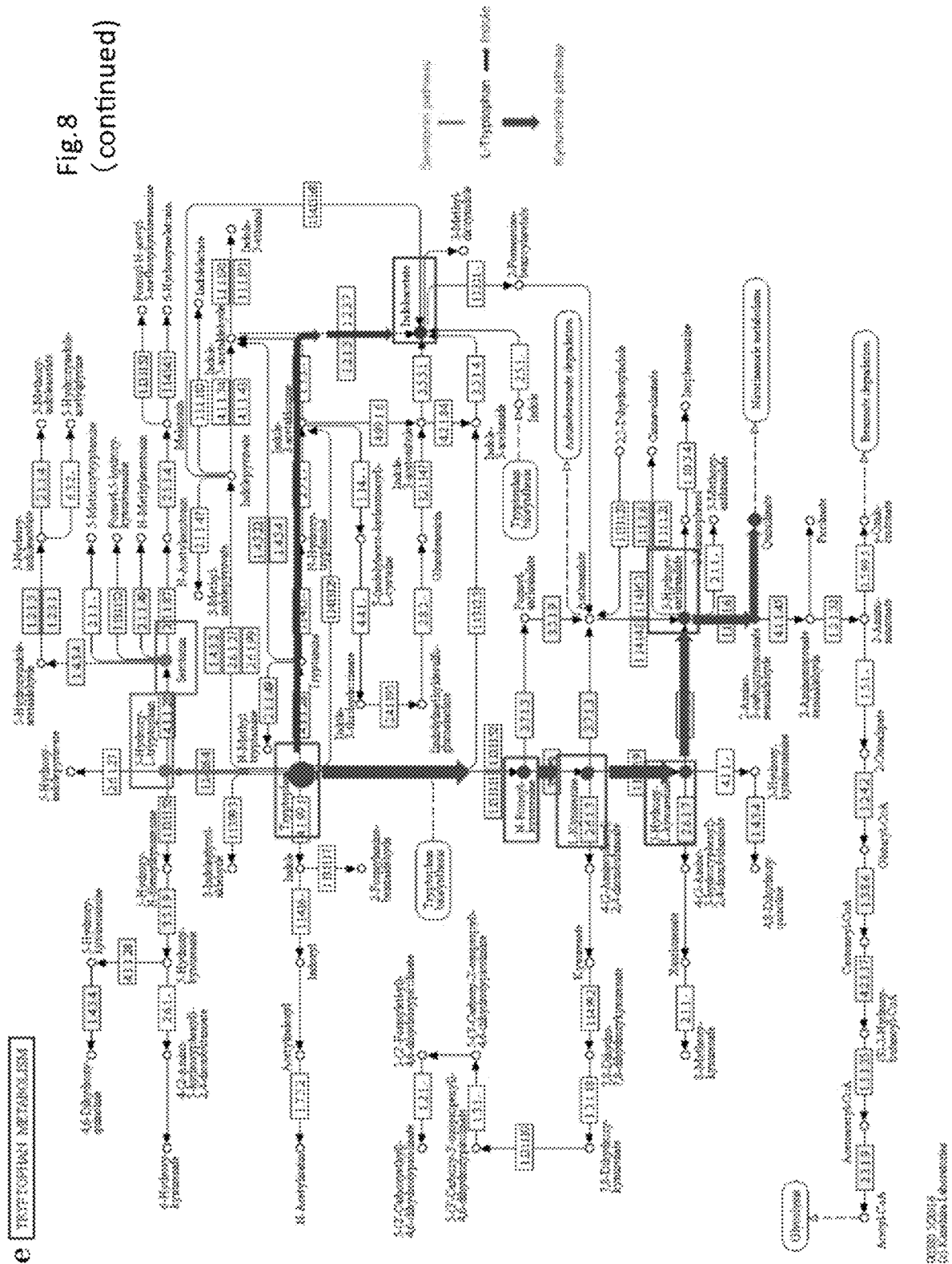
FIG. 8 Tryptophan taken up into T cells is metabolized mainly into kynurenine intracellularly. (a) Schematic diagram of experiment. A mixture of 'Complete Freund's Adjuvant' (CFA) and Ovalbumin (OVA) (1 mg/mL OVA, 30 μL/mouse) was administered subcutaneously to the left footpad of 8-9 week-old male WT C57BL/6 mice. One week after administration, the following lymph nodes (LNs) were isolated and analyzed: popliteal LN ipsilateral (the site indicated with medium gray circle), popliteal LN contralateral (the site indicated with dark gray circle), and pooled LN (mixture of brachial, axillary and inguinal LNs: the sites indicated with light gray circles). (b) Flow cytometry of CD4$^+$ T cells (upper row) and CD8$^+$ T cells (lower row) in popliteal LN ipsilateral and contralateral. Digits appearing in the diagrams represent percentages of CD62L$^+$ CD44$^{lo}$ cells (naïve T cells: Naïve), CD62L$^+$ CD44$^{hi}$ cells (central memory T cells: CM) and CD62L$^-$ CD44$^{hi}$ cells (effector memory T cells: EM). (c) Cell counts of various types of cells in popliteal LN ipsilateral (dark gray) and contralateral (medium gray). These counts correspond to CD62L$^+$ CD44hi cell (central memory T cells: CM) and CD62L$^-$ CD44$^{hi}$ cell (effector memory T cells: EM) populations in the diagrams shown in (b) above. (d) Concentrations of tryptophan metabolites in popliteal LN ipsilateral (medium gray bars), popliteal LN contralateral (dark gray bars), and pooled LN (mixture of brachial, axillary and inguinal LNs: light gray bars). Individual compound concentrations of three pathways of tryptophan metabolism are shown. (serotonin pathway: 5-OH-Trp, 5-HT; indole pathway: 3-indoleacetic acid; kynurenine pathway: N-formyl kynurenine, L-kynurenine, 3-OH-kynurenine, 3-OH-anthranilic acid, quinolinic acid, nicotinic acid) (e) Outline of tryptophan degradation pathways. Serotonin pathway (shown by arrows pointing upwards from tryptophan), indole pathway (shown by arrows pointing to the right from tryptophan) and kynurenine pathway (shown by arrows pointing downwards from tryptophan) are shown. These show that tryptophan taken up into activated T cells is mainly metabolized via kynurenine pathway intracellularly.

The preceding Examples showed that it is possible to predict the antitumor effect of PD-1 inhibitory antibody by measuring mitochondrial activity. Mitochondrial activity is brought about by T cell activation upon stimulation with a tumor antigen. As T cells are activated and proliferate, the TCA cycle is induced to meet increased energy demands. A preceding Example showed that concentrations of TCA cycle-related metabolites in plasma decreased. At the same time, levels of blood amino acids were measured, revealing that they decreased, like those of TCA cycle-related metabolites (FIG. 6). This is because the growing cells consume TCA cycle-related metabolites and amino acids for energy production and constituting cytoskeletons. Briefly, TCA cycle-related metabolites and amino acids are necessary for activation and growth of T cells, and such activation and growth would likely consume blood metabolites. In agreement with this, T cells were activated in PD-1$^{-/-}$ mice and antigen-stimulated mice, and a large number of amino acids were taken up into T cells (FIG. 7). Further, it was also revealed that Trp (tryptophan), an amino acid essential for T cell activation, was metabolized (mainly into kynurenine) and consumed during T cell activation (FIG. 8). As indicators of T cell activation during PD-1 blockade (i.e., indicators capable of judging the efficacy of PD-1 inhibitory antibody therapy), decreased levels of amino acids may compliment TCA cycle-related metabolites as biomarkers of the PD-1 blockade efficacy.

Footpad Immunization and Isolation of Lymph Nodes

A mixture of complete Freund's adjuvant (CFA) and ovalbumin (OVA) (1 mg/ml OVA, 30 μl/mouse) was administered subcutaneously to the left footpad of 8-9 week-old male C57BL/6N mice.

One week after administration, mice were euthanized using carbon dioxide, and popliteal lymph nodes (LNs), brachial LNs, axillary LNs and inguinal LNs were isolated.

Flow Cytometry

Isolated popliteal LNs were homogenized on slide glass and counted. Popliteal LN cells were stained with anti-CD3ε antibody, anti-TCR β antibody, anti-CD4 antibody, anti-CD8 antibody, anti-CD44 antibody and anti-CD62L antibody for 10 min on ice. Then, cell populations were analyzed with FACS-Aria cell sorter.

Metabolome Analysis

For isolation of ipsilateral and contralateral popliteal LN, lymph nodes from 6 mice were collected into a tube as one sample and frozen quickly in liquid nitrogen. For branchial, axillary and inguinal LNs, lymph nodes from 6 mice were collected into a tube as one sample and frozen quickly in liquid nitrogen. The frozen lymph nodes were homogenized together with internal standard substances, methionine sulfone and trimesic acid, in 500 μl of ice-cooled methanol. After addition of an equivalent volume of chloroform and 400 μl of ultrapure water, the homogenate was centrifuged at 4° C.×15000 g for 15 min to recover the aqueous layer. The supernatant was ultrafiltered, concentrated in a vacuum condenser, dissolved in 50 μl of ultrapure water and subjected to analysis by LC-MS/MS.

Imaging Mass Spectrometry

After isolation, lymph nodes were embedded in SCEM and frozen quickly in liquid nitrogen. Then, sections were prepared in a cryostat (MC050, Leica Microsystems).

MALDI-MS imaging was analyzed with Nd:YAG laser-mounting 7T FT-ICR-MS (Solarix Bruker Daltonik). Laser output was optimized for a smaller in-source decay of tryptophan. Data were obtained in positive mode of laser scanning with pitch distance 80 μm. For construction of images from the data, Fleximaging 4.0 software (Bruker Daltonics) was used.

Example 5

Results and Observation

It has been revealed from mouse models that when PD-1 inhibitory antibody exerts antitumor effect, killer T cells are activated and energy metabolism is enhanced. In order to examine whether these events would also occur in human patients, peripheral blood was collected from PD-1 inhibitory antibody (Nivolumab)-administered patients with non-small-cell lung cancer (NSCLC), and metabolites in plasma were examined. Blood samples were collected immediately before the 1$^{st}$, 2$^{nd}$ and 3$^{rd}$ administrations of Nivolumab, and plasma metabolites were detected by mass spectrometry in the same manner as the mouse blood samples.

Figure 9:
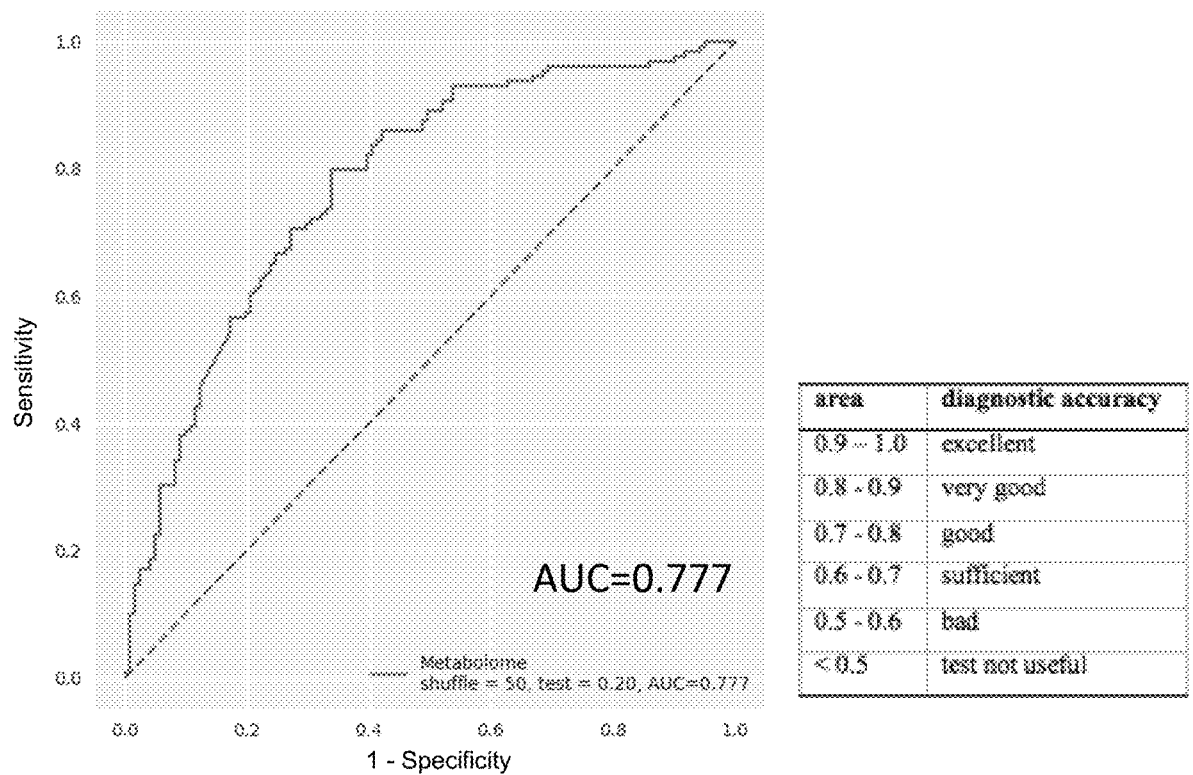
FIG. 9 Nivolumab was administered to a total of 22 patients (responders: 10, non-responders: 12). At three time points before and after the administration, metabolites were tested (145 items/time point). All the test results were collected together thereby to obtain data on a total of 435 items. With these data, ROC analysis was performed.
Figure 10:
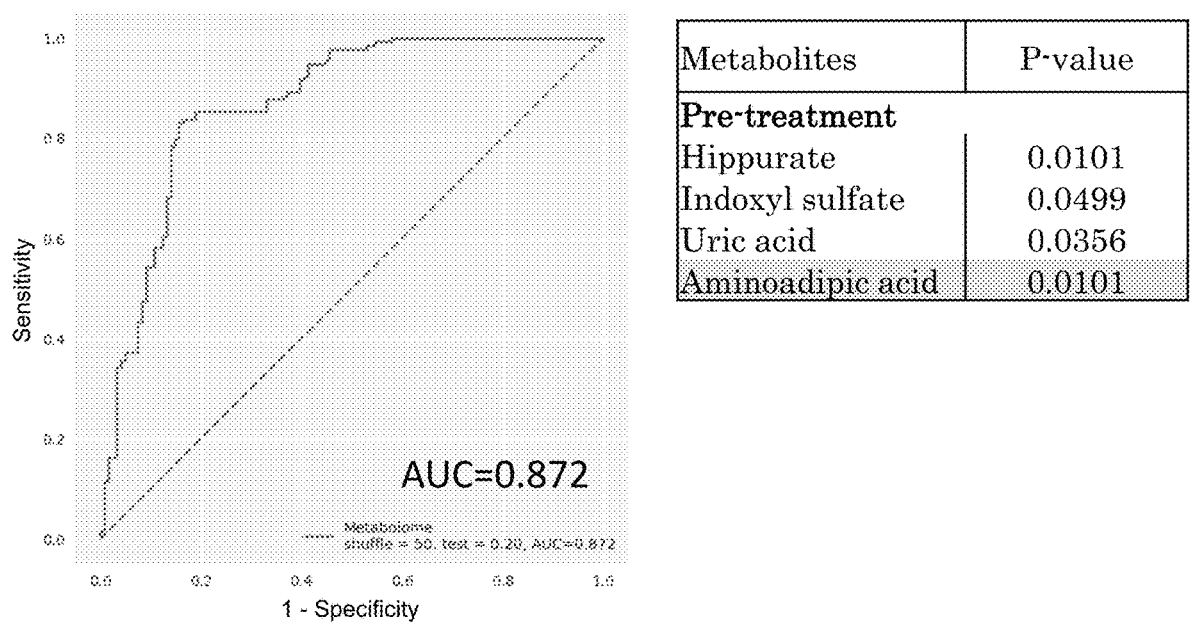
FIG. 10 ROC analysis was performed on the pretreatment metabolite items as shown in Table 2.
Figure 11:
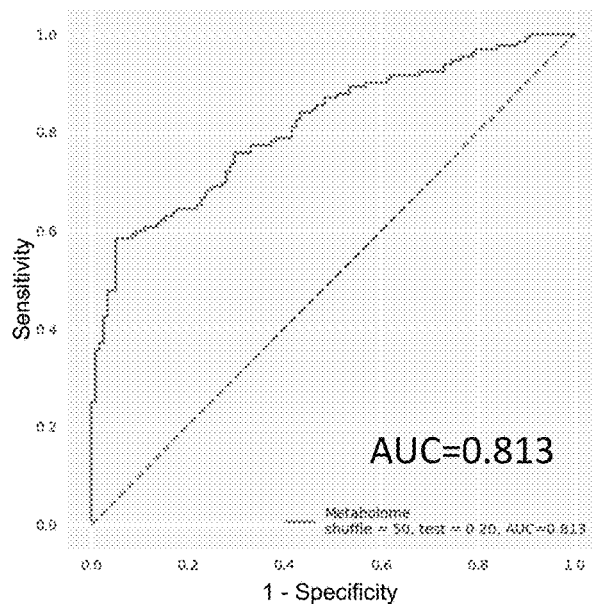
FIG. 11 ROC analysis was performed on the metabolite items 2 weeks after $1^{st}$ Nivolumab as shown in Table 2.
Figure 12:
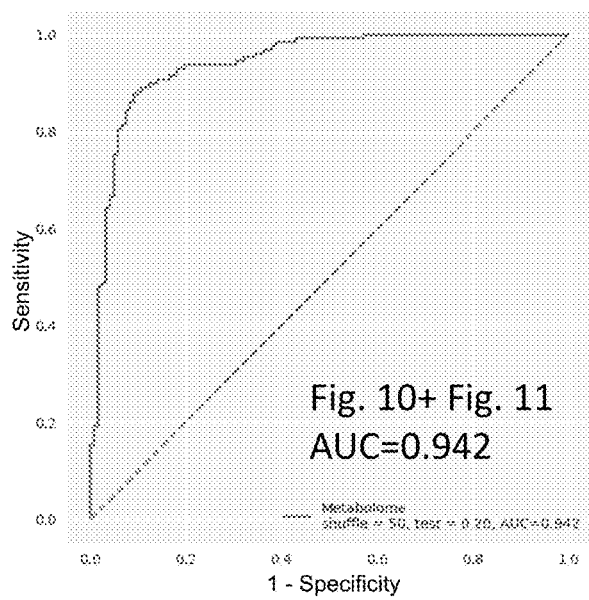
FIG. 12 The pretreatment metabolite items and the metabolite items 2 weeks after $1^{st}$ Nivolumab as shown in Table 2 were collected together and subjected to ROC analysis.

The results of 145 metabolites for each patient measured at the three time points are shown in Table 1. All of these values were divided into responder and non-responder groups. Based on the results obtained, probability of therapeutic effect calculated by machine learning (ROC analysis) was AUC=0.777 (FIG. 9). Subsequently, both the responder and non-responder groups were analyzed by Mann-Whitney U test for each metabolite item. Metabolite items with significant difference are shown in Table 2. As biomarkers for predicting therapeutic effect, early ones are more useful. For the 4 metabolites which showed significant difference before treatment (immediately before the Pt administration), ROC analysis by machine learning demonstrated AUC=0.872 (FIG. 10). Further, based on the data for 8 metabolites which showed significant difference before treatment and after the 1$^{st}$ treatment (immediately before the 1st and $2^{nd}$ administrations), ROC analysis produced a high predictive effect with AUC=0.813 (FIG. 11). When the data immediately before treatment was combined with the data after the $1^{st}$ treatment, a high effect predicting rate of AUC=0.942 could be obtained (FIG. 12).

Figure 13:
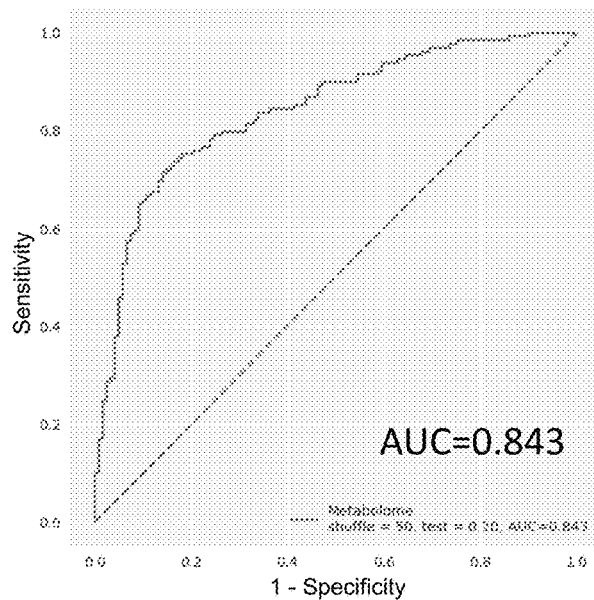
FIG. 13 ROC analysis was performed on the metabolite items 2 weeks after $2^{nd}$ Nivolumab as shown in Table 2.

For PD-1 inhibitory antibody therapy to be effective, T cell activation by PD-1 blockade is necessary. Indicators of such T cell activation include the activation of mitochondria and the resulting enhancement of energy metabolism. As indicators of these phenomena in mouse models, energy metabolism-related metabolites including blood amino acids were found to decrease as a result of consumption of metabolites by T cells. In the present study, the same tendency was observed in human. Briefly, several energy metabolism-related metabolites in blood (e.g., aminoadipic acid, 2-oxobutyric acid, nicotinamide, lactic acid, pyruvic acid, 2-hydroxybutyric acid, 2-oxoglutaric acid, pyroglutamic acid, etc.) showed a tendency to decrease in responders following administration of PD-1 antibody (Table 2). These results show that enhancement of energy metabolism/amino acid metabolism is also critical in patients for PD-1 inhibitory antibody therapy. Even after the $2^{nd}$ administration (immediately before the $3^{rd}$ administration), a high value of AUC=0.843 could be obtained when ROC analysis was performed based on the 9 metabolites shown in Table 2 (FIG. 13). Although the term "after the $2^{nd}$ administration" means 4 weeks after the start of treatment, these metabolites are effective as predictive biomarkers or markers to confirm efficacy.

Human differ from mouse models in that every patient varies in genetic background and living environment, which greatly affect the immune system. On the other hand, in mice have identical genetic background and rearing environment, making it impossible to evaluate the effect of genetic background and/or environment on T cells, and to identify corresponding differences in metabolites. In other words, in experiments using mice, causes derived from genetic background and rearing environment that may affect T cell activating capacity before administration of PD-1 inhibitory antibody are difficult to study. However, in the case of human, genetic background and living environment vary from one patient to another, so it is possible to identify factors that may affect activation and potential of T cells. This is where analysis of human specimens has great merit.

Figure 14:
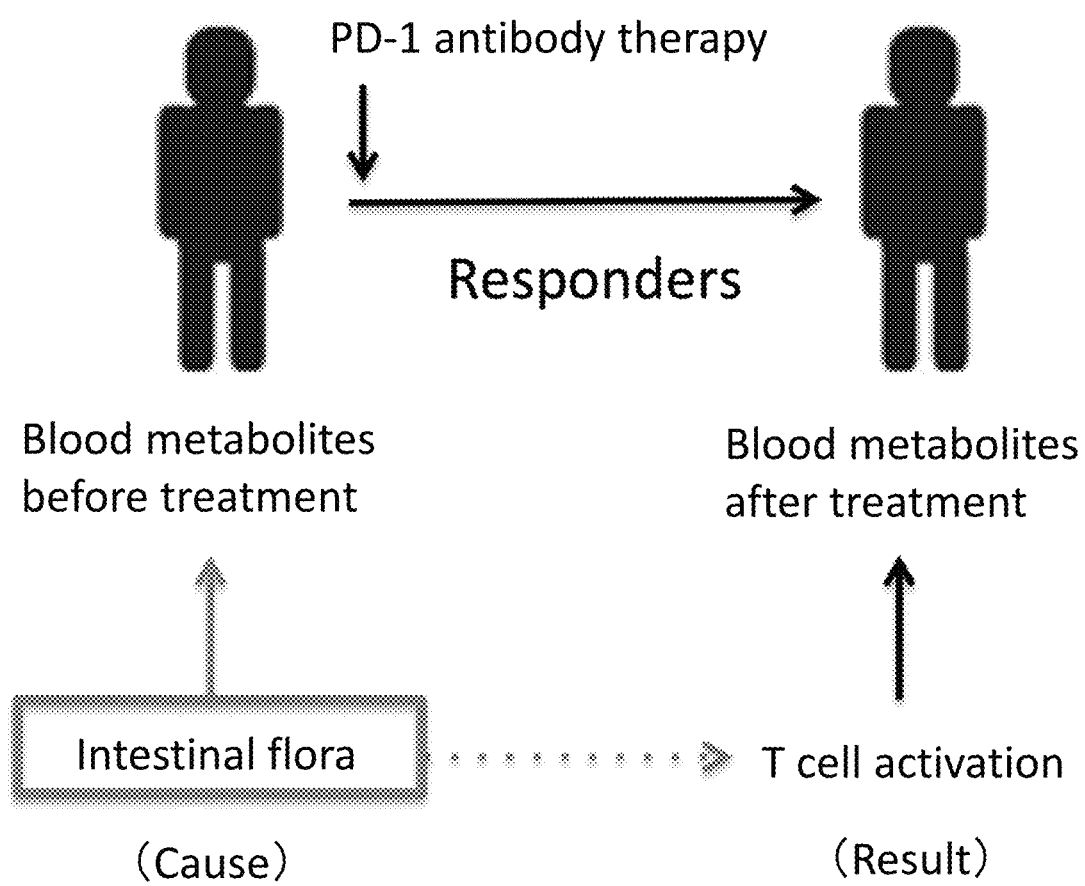
FIG. 14 It appears that pretreatment metabolites are affected by the balance of intestinal flora which regulates (or is responsible for regulating) T cell activation capacity whereas posttreatment metabolites are affected by energy metabolism caused by T cell activation.

As an example factor that is greatly affected by genetic background and living environment, intestinal flora may be preferable. It has already been known that intestinal flora is an important causative factor regulating human immunocompetence and T cell activation capacity[1], and it has also been reported that intestinal flora regulates the therapeutic effect of T cell-mediated antitumor immunity[2,3,4]. Further, a relationship between the metabolism of intestinal bacteria and metabolites detected in the blood has also been reported[5,6]. Therefore, the activation capacity of T cells responsible for antitumor immunity and the reactivity to PD-1 antibody therapy could be predicted by examining intestinal bacteria-related blood metabolites in cancer patients. In the present analysis of metabolites in cancer patients-derived plasma, it was confirmed that aside from energy metabolism-related metabolites, intestinal flora-related metabolites (e.g., hippurate, indoxyl sulfate, uric acid, 4-cresol) also increased in "responders" to PD-1 antibody therapy. These results suggest that intestinal flora, affected by genetic background and living environment could regulate T cell activation capacity, as well as the activation of killer T cells by PD-1 blockade. Importantly, energy metabolism-related metabolites show the "result" in which T cells were activated by PD-1 blockade whereas intestinal flora-related metabolites reflect the "cause" which determines the activation capacity of T cells. Accordingly, intestinal flora-related metabolites reflecting the "cause" are higher in responders than non-responders before treatment, whereas energy metabolism-related metabolites reflecting the "result" show greater differences after treatment. In other words, it appears that pretreatment metabolites are affected by the balance of intestinal flora which regulates T cell activation capacity and that posttreatment metabolites are more affected by energy metabolism triggered by T cell activation (FIG. 14). This is consistent with the following observation: although a high predictive effect is obtainable even from pretreatment metabolites (FIG. 10), a still higher predictive effect is obtainable when the pretreatment metabolites and the metabolites immediately after treatment (after the 1st administration) are combined (FIG. 12).

Experimental Methods
Peripheral Blood Specimens

Collection of specimens from progressive non-small-cell lung cancer patients was performed in cooperation with the Department of Respiratory Medicine, Kyoto University Hospital. Nivolumab was administered every 2 weeks, and peripheral blood samples (7 ml each) were collected in EDTA blood collection tubes immediately before the $1^{st}$, $2^{nd}$ and $3^{rd}$ administrations. Immediately after the collection, blood was preserved at 4° C. and separated into plasma and leucocytes within 4 hours. Immediately after the isolation, plasma was preserved at −80° C. Specimens from a total of 22 patients were analyzed. Those patients who were judged PD (progressive disease) according to the RECIST classification within 3 months after the start of treatment are regarded as non-responders, and those patients who were not judged PD within 3 months are regarded as responders[7].

Data Sets

For independent variable, PD at 3 months from the start of treatment was used. Briefly, "1" was assigned to patients who were not judged PD within 3 months, and "0" was assigned to patients who were judged PD within 3 months. Out of the 22 patients, 12 were responders and 10 were non-responders.

For explanatory variable, each item for metabolome analysis was used. The same measurement at 3 times of blood collection were treated as different items. The total number of these items amounted to 435.

Preprocessing of Data

Since the technique used for analysis requires inter-item products, accurate analysis will become difficult if there are missing values of measurement and if there is a big difference in absolute value between items. Therefore, complementing and scaling of missing values are necessary as preprocessing.

As a scaling technique, linear transformation was employed, with each item being transformed using a minimum value of "0" and a maximum value of "1". As a calculation formula, the following was used:

$$\text{Scaling } (x) = \frac{x - \min(x)}{\max(x) - \min(x)}$$

Missing value was regarded as 0.

Evaluation Technique

Data sets are randomly divided into 4:1. The larger portion is used as training data and the smaller portion is used as test data. Learning is performed only with training data. With a constructed model, test data are predicted; ROC curve is plotted; and area under the curve (AUC) is calculated. In order to prevent any bias resulting from the dividing of training data and test data, the same trial was repeated 50 times while solely changing the random data division. Evaluation for all the trials was performed using the average AUC for prediction accuracy.

Analysis Technique

For prediction, a support vector machine (which is machine learning) was used. Support vector machine is a technique for discrimination which learns high-dimensional hyperplane that maximally separates input samples into individual independent variables using kernel transformation. The present inventors also performed classifications by logistic regression, stochastic gradient descent, discriminant analysis, decision tree, k-nearest neighbor algorithm, naïve Bayes classifier, adaptive boosting, gradient boosting and random forest, and confirmed that support vector machine achieves a comparable or higher accuracy.

When performing kernel transformation, support vector machine requires the definition of kernel function. Here, Gaussian kernel was used as the kernel function. Support vector machine with Gaussian kernel has two hyper-parameters: cost parameter C defining a function that minimizes misclassification and coefficient $\gamma$ defining distribution of decision boundary (high-dimensional hyperplane). Against these two hyper-parameters, C was varied from 1 to 100,000 and $\gamma$ from 0.00001 to 0.1, respectively, according to a logarithmic scale. Learning and evaluation were performed using combinations of individual hyper-parameters, followed by calculation of the mean AUC which would give the highest prediction accuracy.

TABLE 1

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

|  | | | | | GCMS | | | | | |
|---|---|---|---|---|---|---|---|---|---|---|
| ID | 2<br>Phenol-TMS | 3<br>Lactic<br>acid-2TMS | 4<br>2-Hydroxyisobutyric<br>acid-2TMS | 5<br>Caproic<br>acid-TMS | 6<br>Glycolic<br>acid-2TMS | 9<br>Oxalic<br>acid-2TMS | 10<br>2-Hydroxybutyric<br>acid-2TMS | 11<br>4-Cresol-TMS |
| Non-responders | | | | | | | | |
| L1-1 | 0.008625376 | 1.414600929 | 0.037819388 | 0.049101313 | 0.021997792 | 0.018035387 | 3.30725731 | 0.13589311 |
| L1-2 | 0.028128329 | 1.181514309 | 0.02631974 | 0.041308335 | 0.029124152 | 0.016925324 | 0.903910435 | 0.013176345 |
| L1-3 | 0.03588066 | 1.436551017 | 0.004542139 | 0.039854473 | 0.034699257 | 0.021274215 | 0.950219947 | 0.023189521 |
| L5-1 | 0.007836503 | 1.400298895 | 0.029176371 | 0.036701841 | 0.030052572 | 0.017615063 | 1.1911864 | 0.006027204 |
| L5-2 | 0.007479039 | 1.46066253 | 0.071039108 | 0.061357124 | 0.034243649 | 0.016925833 | 1.031609522 | 0.018529044 |
| L5-3 | 0.007600274 | 1.400462681 | 0.03877037 | 0.060219037 | 0.036674848 | 0.014598166 | 1.01653348 | 0 |
| L6-1 | 0 | 3.32942148 | 0.065412671 | 0.052947653 | 0.03657384 | 0.028788365 | 1.225953113 | 0 |
| L6-2 | 0.005271468 | 2.26057194 | 0.11649692 | 0.04802837 | 0.031124361 | 0.019189152 | 0.973748594 | 0.011796048 |
| L6-3 | 0.004929482 | 2.982674115 | 0.119114288 | 0.045861534 | 0.038788595 | 0.020524654 | 1.22291951 | 0.348678047 |
| L8-1 | 0.020934464 | 1.194619285 | 0.095389618 | 0.12227707 | 0.038261139 | 0.013362753 | 0.760229164 | 0.209225268 |
| L8-2 | 0.040199003 | 1.169657866 | 0.112454209 | 0.067163526 | 0.024936820 | 0 | 1.748224228 | 0.405887255 |
| L8-3 | 0.032177133 | 1.40331824 | 0.127814962 | 0.09585263 | 0.040803526 | 0 | 1.179212455 | 0 |
| L9-1 | 0 | 1.36385477 | 0.068231719 | 0.076139184 | 0.044278623 | 0.017692357 | 2.071199007 | 0 |
| L9-2 | 0 | 2.104408392 | 0.05987366 | 0.04676062 | 0.03558045 | 0.019373707 | 1.804465307 | 0 |
| L9-3 | 0 | 4.362692155 | 0.164395459 | 0.053877672 | 0.046487034 | 0.031010121 | 8.046197521 | 0 |
| L10-1 | 0.008511065 | 0.997465133 | 0.029385675 | 0.037135957 | 0.02471414 | 0.025941106 | 1.542170079 | 0.053206299 |
| L10-2 | 0.012738045 | 1.579765178 | 0.058521345 | 0.072675434 | 0.031749862 | 0.015195484 | 1.641937758 | 0.109117925 |
| L10-3 | 0.013184613 | 1.320796829 | 0.041141516 | 0.069432061 | 0.022261978 | 0.023475745 | 1.303545234 | 0.056667376 |
| L12-1 | 0.016389656 | 1.794946928 | 0.144163313 | 0.082519727 | 0.056375956 | 0.018736246 | 2.352037156 | 0.019623816 |
| L12-2 | 0.023681816 | 1.783025662 | 0.088965543 | 0.104355407 | 0.034797771 | 0.027320799 | 2.044473295 | 0.021350593 |
| L12-3 | 0.047272094 | 2.379156446 | 0.054166243 | 0.125596888 | 0.022672324 | 0.010602476 | 2.27072362 | 0.019456015 |
| L17-1 | 0 | 1.108116835 | 0.047962719 | 0.062780895 | 0.021415668 | 0.017732941 | 1.226330625 | 0 |
| L17-2 | 0 | 1.527534815 | 0.061573848 | 0.049359775 | 0.021240605 | 0.014007063 | 1.247762383 | 0 |
| L17-3 | 0.005110882 | 1.175798279 | 0.037483447 | 0.053290335 | 0.018882172 | 0.012589331 | 1.587831651 | 0 |
| L19-1 | 0.008461406 | 1.275556365 | 0.044962245 | 0.055769011 | 0.031223782 | 0.015878842 | 0.97903478 | 0.18563134 |
| L19-2 | 0.004100327 | 1.171576711 | 0.036431224 | 0.046272815 | 0.020880623 | 0.013083148 | 0.808421596 | 0.144362151 |
| L19-3 | 0 | 1.371179324 | 0.051370166 | 0.082972559 | 0.019516664 | 0.016005803 | 0.980855348 | 0.031388487 |
| L22-1 | 0.004703251 | 2.261236689 | 0.049333706 | 0.064034802 | 0.023901314 | 0.013775115 | 1.747720574 | 0.004726171 |
| L22-2 | 0 | 1.405641364 | 0.046274629 | 0.050669064 | 0.024967788 | 0.0199916 | 2.025626629 | 0 |
| L22-3 | 0 | 1.378856014 | 0.05541551 | 0.065845973 | 0.021373638 | 0.016898099 | 2.018852809 | 0.039617603 |
| Responders | | | | | | | | |
| L2-1 | 0 | 1.561964208 | 0.07069402 | 0.0809079 | 0.027490179 | 0.010109123 | 1.636097774 | 0.093164557 |
| L2-2 | 0.010259468 | 1.312102439 | 0.064288862 | 0.044335001 | 0.023525752 | 0.017180331 | 1.380497162 | 0.047409212 |
| L2-3 | 0.013919664 | 1.429510741 | 0.070926509 | 0.088107465 | 0.035834752 | 0 | 1.51241066 | 0.060084031 |
| L3-1 | 0 | 1.311422882 | 0.045123733 | 0.052666817 | 0.03545902 | 0.015603534 | 1.372610994 | 0.063483644 |
| L3-2 | 0.008663844 | 0.821814983 | 0.045845316 | 0.056335564 | 0.030632142 | 0.019550242 | 1.185063615 | 0.035704915 |
| L3-3 | 0.005621556 | 1.631104455 | 0.03897909 | 0.047632352 | 0.037268423 | 0.015106303 | 1.702538082 | 0.029329697 |
| L4-1 | 0.007663444 | 1.430106063 | 0.110858941 | 0.111152467 | 0.032355923 | 0.01668104 | 1.739473167 | 0.185912275 |

TABLE 1-continued

L number represents patient number. With respect to numbers appearing after hyphen (-), "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | | | | | GCMS | | | | | |
|---|---|---|---|---|---|---|---|---|---|---|
| | 12 | 13 | 14 | 15 | 16 | 17 | 21 | 23 | 25 |
| ID | 3-Hydroxybutyric acid-2TMS | 3-Hydroxyisobutyric acid-2TMS | 2-Hydroxyisovaleric acid-2TMS | 2-Aminobutyric acid-2TMS | 3-Hydroxyisovaleric acid-2TMS | Valine-2TMS | Octanoic acid-TMS | Glycerol-3TMS | Phosphoric acid-3TMS |
| L4-2 | 0.004323333 | 0.076395389 | 0.300475825 | 0.0648577 | 0.0835513 | 0.036721357 | 0.111961755 | 1.132921294 | 0.147752406 |
| L4-3 | 0 | 0.026905518 | 0.20224353 | 0.09915537 | 0.033093232 | 0.026892498 | 0.062154711 | 0.693675251 | 0.260982944 |
| L7-1 | 0.007933453 | 0.021032565 | 0.232924466 | 0.087982468 | 0.027198691 | 0.022543276 | 0.090274453 | 1.461144727 | 0.111603652 |
| L7-2 | 0.283590572 | 0.026680524 | 0.291293364 | 0.126197676 | 0.034643491 | 0.018480739 | 0.091276675 | 1.407087862 | 0.014842699 |
| L7-3 | 0.307747745 | 0.051063646 | 0.476569207 | 0.052604987 | 0.023627519 | 0.015065494 | 0.109994395 | 1.049051359 | 0.058111634 |
| L13-1 | 0.106188238 | 0.026773985 | 0.356142701 | 0.079026319 | 0.030039952 | 0.026516138 | 0.143302979 | 0.980253176 | 0.177052565 |
| L13-2 | 0.056912341 | 0.041629582 | 0.124099647 | 0.084073059 | 0.024515094 | 0.028628862 | 0.099963298 | 0.604727129 | 0.54140667 |
| L13-3 | 0.156677524 | 0.034630266 | 0.133764131 | 0.068218342 | 0.024717936 | 0.025297535 | 0.115488027 | 0.718820407 | 0.5291616 |
| L15-1 | 0.03483907 | 0.028160426 | 0.115221358 | 0.048514759 | 0.023953026 | 0.023872251 | 0.093589798 | 0.2775928 | 0.137032434 |
| L15-3 | 0.015603956 | 0.015832462 | 0.51068788 | 0.04871682 | 0.021828222 | 0.015988764 | 0.260078195 | 0.317235541 | 0.102416593 |
| L16-1 | 0.008480285 | 0.028160426 | 0.739615015 | 0.085497701 | 0.025189028 | 0.006301979 | 0.167490988 | 0.555428956 | 0.077883895 |
| L16-2 | 0 | 0.026206602 | 0.687585383 | 0.159493208 | 0.021040485 | 0.006628849 | 0.218417865 | 0.933301699 | 0.054159567 |
| L16-3 | 0.010109745 | 0.017622243 | 0.05697039 | 0.066356499 | 0.016081948 | 0.0124696 | | 0.666172965 | 0.044657745 |
| L18-1 | 0.1012053 | 0.828449894 | 0.063628869 | 0.052121304 | 0.022957984 | 0.018026493 | | 0.835237647 | 0.011800171 |
| L18-2 | 0.006614944 | 0.976539696 | 0.047822463 | 0.05744301 | 0.020082375 | 0.017964626 | | 1.045298075 | 0.004118739 |
| L18-3 | 0.006735426 | 0.697368556 | 0.066403077 | 0.048824972 | 0.019584152 | 0.014797372 | | 0.84958919 | 0.022741061 |
| L21-1 | 0 | 0.882665458 | 0.051570696 | 0.06847512 | 0.015456263 | 0.017442533 | | 0.993616939 | 0.105175872 |
| L21-2 | 0.012863206 | 0.733778879 | 0.068855985 | 0.07627372 | 0.017541434 | 0.019661616 | | 0.934197538 | 0.065088053 |
| L21-3 | 0.008891419 | 0.771305024 | 0.065076872 | 0.046217664 | 0.01649710 | 0.022513201 | | 1.516262022 | 0.104365431 |
| L23-1 | 0.007568898 | 0.808532128 | 0.034984294 | 0.063461705 | 0.018628731 | 0.012165192 | | 0.40680951 | 0.175458537 |
| L23-2 | 0 | 1.036204022 | 0.043367719 | 0.077537485 | 0.023173909 | 0.016453058 | | 0.941539023 | 0.107434615 |
| L23-3 | 0 | 1.192472552 | 0.019331363 | 0.07837345 | 0.018062996 | 0.019610224 | | 0.72619899 | 0.130097646 |
| L24-1 | 0 | 0.825318223 | 0.006368481 | 0.049974588 | 0.018114255 | 0.013752227 | | 0.712675966 | 0.004763319 |
| L24-2 | 0 | 0.980117805 | 0.029050587 | 0.057428691 | 0.020366111 | 0.016078509 | | 1.466193504 | 0 |
| L24-3 | 0 | 0.905653272 | 0.045907482 | 0.062373167 | 0.011078287 | 0.016289184 | | 0.857277672 | 0 |
| L25-1 | 0.012879063 | 1.563157711 | 0.082996748 | 0.061557759 | 0.02202788 | 0.015862265 | | 0.786399789 | 0.307653231 |
| L25-2 | 0.030836451 | 0.720549748 | 0.070056631 | 0.063892306 | 0.02148423 | 0.011474028 | | 0.266623294 | 0.225584421 |
| L25-3 | 0.018864723 | 0.823411863 | 0.062551451 | 0.067705638 | 0.027612123 | 0.006453721 | | 0.503465655 | 0.22755808 |

Non-responders

| ID | 12 3-Hydroxybutyric acid-2TMS | 13 3-Hydroxyisobutyric acid-2TMS | 14 2-Hydroxyisovaleric acid-2TMS | 15 2-Aminobutyric acid-2TMS | 16 3-Hydroxyisovaleric acid-2TMS | 17 Valine-2TMS | 21 Octanoic acid-TMS | 23 Glycerol-3TMS | 25 Phosphoric acid-3TMS |
|---|---|---|---|---|---|---|---|---|---|
| L1-1 | 0.665964232 | 0.076395389 | 0.300475825 | 1.462357154 | 0.135248589 | 1.126096387 | 0.111961755 | 0.678322227 | 0.437601932 |
| L1-2 | 0.142384336 | 0.026905518 | 0.20224353 | 0.61936509 | 0.112308295 | 1.058801132 | 0.062154711 | 0.625497454 | 0.635162791 |
| L1-3 | 0.283590572 | 0.021032565 | 0.232924466 | 0.675655478 | 0.101806563 | 0.938902637 | 0.090274453 | 0.689425095 | 0.628766283 |
| L5-1 | 0.307747745 | 0.026680524 | 0.291293364 | 0.819972842 | 0.09842663 | 0.883776239 | 0.091276675 | 0.471904657 | 0.565734075 |
| L5-2 | 0.106188238 | 0.051063646 | 0.476569207 | 0.687569822 | 0.127453325 | 0.874004853 | 0.109994395 | 0.621853845 | 0.558478008 |
| L5-3 | 0.056912341 | 0.026773985 | 0.356142701 | 0.964895192 | 0.102398636 | 0.813017873 | 0.143302979 | 0.729953155 | 0.443052414 |
| L6-1 | 0.156677524 | 0.041629582 | 0.124099647 | 0.861380006 | 0.2 | 0.840872597 | 0.099963298 | 0.98241959 | 0.757796945 |
| L6-2 | 1.893233856 | 0.034630266 | 0.133764131 | 0.848378456 | 0.244520448 | 0.638639608 | 0.115488027 | 0.718932389 | 0.906319204 |
| L6-3 | 0.97667056 | 0.028160426 | 0.115221358 | 0.75984372 | 0.182001529 | 0.565234725 | 0.093589798 | 1.120061724 | 0.828190444 |
| L8-1 | 0.319374444 | 0.015832462 | 0.51068788 | 1.058932373 | 0.083397205 | 0.673440948 | 0.260078195 | 1.089962451 | 0.638563078 |
| L8-2 | 1.870793777 | 0.026206602 | 0.739615015 | 1.520527047 | 0.158891491 | 0.790327753 | 0.167490988 | 0.727206475 | 0.627755539 |
| L8-3 | 0.377714006 | 0.017622243 | 0.687585383 | 1.202539803 | 0.137755935 | 0.681605334 | 0.218417865 | 1.089967093 | 0.736293572 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L9-1 | 0.131364157 | 0.044016101 | 0.292910329 | 1.411983708 | 0.08041908 | 0.802313371 | 0.18536403 | 0.859248711 | 0.640425126 |
| L9-2 | 0.168987417 | 0.064973487 | 0.253723437 | 0.869078143 | 0.08773393 | 1.261731011 | 0.077207436 | 0.757490547 | 0.587037987 |
| L9-3 | 1.89214413 | 0.097734958 | 0.561688508 | 1.180736892 | 0.191296096 | 0.883551206 | 0.125849944 | 1.290567085 | 0.807976099 |
| L10-1 | 2.103900392 | 0.030288904 | 0.198431814 | 0.858578403 | 0.045459254 | 0.741404763 | 0.056239721 | 0.915358766 | 0.813773099 |
| L10-2 | 1.316247674 | 0.091414202 | 0.28970479 | 0.98619516 | 0.082016243 | 0.723147554 | 0.119366781 | 1.194074206 | 0.834233971 |
| L10-3 | 1.640408654 | 0.016342708 | 0.21531417 | 0.856919333 | 0.080453753 | 0.514004337 | 0.15290585 | 1.001570419 | 0.744326647 |
| L12-1 | 1.286004353 | 0.04697788 | 0.561540239 | 1.605772855 | 0.145962771 | 0.562063054 | 0.254975865 | 1.574440405 | 0.658905492 |
| L12-2 | 1.535934953 | 0.03994352 | 0.761599257 | 1.328787764 | 0.106601342 | 0.817728668 | 0.242541981 | 1.751791062 | 0.667895455 |
| L12-3 | 0.449701737 | 0.044245925 | 0.795795295 | 1.118630169 | 0.098477482 | 0.734945355 | 0.2735308 | 1.310294779 | 0.459085038 |
| L17-1 | 1.04283697 | 0.047072581 | 0.152039026 | 1.093560464 | 0.070940492 | 0.895705521 | 0.121748161 | 0.550157519 | 0.71058304 |
| L17-2 | 1.484339401 | 0.034432672 | 0.183844814 | 0.892829847 | 0.061657158 | 0.705565517 | 0.089095355 | 1.059150593 | 0.809381509 |
| L17-3 | 1.224641673 | 0.040051435 | 0.19592078 | 1.031544464 | 0.065602416 | 0.695145574 | 0.136162498 | 0.562021881 | 0.755757494 |
| L19-1 | 0.116610098 | 0.03976146 | 0.196647853 | 0.869641904 | 0.102719091 | 1.102695256 | 0.115589963 | 0.441690184 | 0.819984174 |
| L19-2 | 0.112732785 | 0.037588347 | 0.222264332 | 0.724072588 | 0.08415145 | 1.062004846 | 0.097746634 | 0.436673949 | 0.6232551 |
| L19-3 | 0.080866043 | 0.022725265 | 0.22353718 | 0.968788218 | 0.094467721 | 0.950522444 | 0.152910759 | 0.414979051 | 0.812543304 |
| L22-1 | 0.209620119 | 0.057960916 | 0.261461308 | 0.946499379 | 0.074834859 | 1.072611888 | 0.139626032 | 0.711781505 | 0.746129903 |
| L22-2 | 0.357150044 | 0.043087528 | 0.196451348 | 1.022085766 | 0.061489629 | 0.883787652 | 0.106904195 | 0.627612238 | 0.700211283 |
| L22-3 | 0.659762871 | 0.054112369 | 0.191812647 | 1.352510147 | 0.072083956 | 0.959015168 | 0.123728904 | 0.677793207 | 0.723371075 |

Responders

| | | | | | | | | |
|---|---|---|---|---|---|---|---|---|
| L2-1 | 0.555277172 | 0.026940201 | 0.176988215 | 0.975085116 | 0.065194238 | 0.591191619 | 0.199799214 | 1.117127892 | 0.534823221 |
| L2-2 | 0.735011276 | 0.023225071 | 0.297643796 | 0.776515721 | 0.07671027 | 0.780144638 | 0.090510381 | 0.709655512 | 0.717053319 |
| L2-3 | 0.228809826 | 0.024345756 | 0.300683162 | 0.926555195 | 0.094459092 | 0.770655109 | 0.166108872 | 0.85505007 | 0.694825988 |
| L3-1 | 1.630327983 | 0.033006974 | 0.140688312 | 0.844477679 | 0.05255378 | 0.482926978 | 0.106642262 | 1.040193555 | 0.730744483 |
| L3-2 | 0.672734101 | 0.017801009 | 0.111251164 | 0.832619064 | 0.061665578 | 0.568346101 | 0.103611135 | 0.760452948 | 0.702278781 |
| L3-3 | 0.867984696 | 0.028390476 | 0.143299395 | 0.917807556 | 0.056144782 | 0.652774829 | 0.067406522 | 1.074171761 | 0.854599506 |
| L4-1 | 2.172839786 | 0.060709909 | 0.243142239 | 1.605162423 | 0.191790356 | 1.105449896 | 0.24164435 | 1.02169792 | 1.02398136 |
| L4-2 | 0.113793821 | 0.034505745 | 0.1940375 | 1.075165111 | 0.103902559 | 0.751446891 | 0.119843404 | 0.501918912 | 0.903040975 |
| L4-3 | 0.174130198 | 0.039659214 | 0.210587116 | 1.109166893 | 0.12454981 | 0.762953588 | 0.192265222 | 0.857459568 | 1.001486477 |
| L7-1 | 2.66241023 | 0.035775722 | 0.277592657 | 0.63922939 | 0.155162458 | 0.415234154 | 0.188754827 | 0.84285869 | 0.62013858 |
| L7-2 | 1.283842933 | 0.038805763 | 0.308033374 | 0.697726856 | 0.119682682 | 0.364896701 | 0.17008906 | 0.932279396 | 0.640282453 |
| L7-3 | 2.120523949 | 0.020323338 | 0.286139484 | 0.69913593 | 0.099767921 | 0.456816185 | 0.147639215 | 1.005015275 | 0.633976687 |
| L13-1 | 1.009045204 | 0.044189074 | 0.147771244 | 1.018085918 | 0.060551241 | 0.980118508 | 0.165596804 | 0.596530053 | 0.945315797 |
| L13-2 | 0.185850828 | 0.028390476 | 0.144748583 | 0.67185854 | 0.062949994 | 0.918884354 | 0.112192796 | 0.541071641 | 0.907190557 |
| L13-3 | 0.373536295 | 0.044433017 | 0.176764617 | 0.791509964 | 0.090543821 | 1.02169792 | 0.097411851 | 0.587164279 | 1.006650136 |
| L15-1 | 0.133975295 | 0.021231515 | 0.165471604 | 0.700571642 | 0.084416553 | 0.731489996 | 0.180439915 | 0.532446875 | 0.743314279 |
| L15-2 | 0.474458383 | 0.019326971 | 0.182658637 | 0.691114788 | 0.078154462 | 0.663562551 | 0.33991996 | 0.781265633 | 0.688854042 |
| L16-1 | 0.075428579 | 0.016393959 | 0.225454706 | 0.682200215 | 0.09378679 | 0.939454416 | 0.151612639 | 0.79865776 | 0.518159898 |
| L16-2 | 0.096244131 | 0.0320514 | 0.254930296 | 0.659840102 | 0.044992774 | 0.803363314 | 0.112934883 | 0.505370662 | 0.371905758 |
| L16-3 | 0.287704978 | 0.030300569 | 0.263144819 | 0.631457743 | 0.067677004 | 0.818206141 | 0.108206762 | 0.760791771 | 0.563732961 |
| L18-1 | 0.987395617 | 0.018897618 | 0.211472417 | 0.748772185 | 0.077467389 | 0.808000647 | 0.109185722 | 0.563201473 | 0.593640148 |
| L18-2 | 1.342366644 | 0.025211674 | 0.234349396 | 0.604540678 | 0.069217359 | 0.794453593 | 0.109458605 | 0.656340966 | 0.641174505 |
| L18-3 | 0.549225169 | 0.01814966 | 0.199528006 | 0.85596985 | 0.0664802 | 0.741385338 | 0.137952842 | 0.478796261 | 0.582161918 |
| L21-1 | 1.125583346 | 0.03439332 | 0.20913684 | 1.09694153 | 0.088244369 | 1.135210969 | 0.195515196 | 0.770528001 | 0.662112388 |
| L21-2 | 0.322540378 | 0.034379981 | 0.198071863 | 0.796919909 | 0.088855601 | 1.063729837 | 0.086881374 | 0.536283152 | 0.693468533 |
| L21-3 | 0.658962902 | 0.036240529 | 0.20813277 | 0.973287362 | 0.100386681 | 1.11884757 | 0.113950893 | 0.760916776 | 0.721337167 |
| L23-1 | 0.600041217 | 0.024748796 | 0.195785898 | 0.747116387 | 0.081371894 | 0.604331508 | 0.173141655 | 0.697699979 | 0.570714861 |
| L23-2 | 0.749114307 | 0.046285297 | 0.233583411 | 0.889850995 | 0.109386407 | 0.765301657 | 0.172111076 | 0.918078566 | 0.638121288 |
| L23-3 | 0.580116312 | 0.029505292 | 0.190578996 | 0.796894748 | 0.08840343 | 0.805161627 | 0.105755781 | 0.702189958 | 0.621174245 |

TABLE 1-continued

L number represents patient number. With respect to numbers appearing after hyphen (-), "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| ID | 27<br>Proline-<br>2TMS | 28<br>Succinic<br>acid-2TMS | 29<br>Glyceric<br>acid-3TMS | 30<br>Fumaric<br>acid-2TMS | 31<br>Serine-<br>3TMS | 32<br>Threonine-<br>3TMS | 35<br>Decanoic<br>acid-TMS | 36<br>Aspartic<br>acid-3TMS | 37<br>Methionine-<br>2TMS |
|---|---|---|---|---|---|---|---|---|---|
| L24-1 | 0.143337036 | 0.026477151 | 0.272083019 | 0.982692339 | 0.069660027 | 0.883401018 | 0.12815615 | 0.539113854 | 0.784559142 |
| L24-2 | 0.418624013 | 0.044463061 | 0.369217721 | 1.240126547 | 0.062513659 | 0.945057289 | 0.111357984 | 0.711835656 | 0.70830775 |
| L24-3 | 0.120080216 | 0.033492767 | 0.2618787 | 1.167979649 | 0.066756934 | 0.795497175 | 0.137183184 | 0.69251014 | 0.663460411 |
| L25-1 | 0.160176502 | 0.056845177 | 0.283867305 | 0.992843305 | 0.163523265 | 0.923348158 | 0.118038159 | 0.712492094 | 0.808761349 |
| L25-2 | 0.127020153 | 0.025313835 | 0.114244947 | 0.915704337 | 0.093536987 | 0.503703923 | 0.140386805 | 0.890863657 | 0.469252266 |
| L25-3 | 0.164327952 | 0.037999661 | 0.149239944 | 1.135873766 | 0.091062193 | 0.889061351 | 0.14174307 | 0.79285252 | 0.743107966 |

GCMS

| ID | 27<br>Proline-<br>2TMS | 28<br>Succinic<br>acid-2TMS | 29<br>Glyceric<br>acid-3TMS | 30<br>Fumaric<br>acid-2TMS | 31<br>Serine-<br>3TMS | 32<br>Threonine-<br>3TMS | 35<br>Decanoic<br>acid-TMS | 36<br>Aspartic<br>acid-3TMS | 37<br>Methionine-<br>2TMS |
|---|---|---|---|---|---|---|---|---|---|

Non-responders

| L1-1 | 0.123226866 | 0.017032176 | 0.042415105 | 0.02513633 | 0.038856227 | 0.182421943 | 0.072169571 | 0.045732989 | 0.017060198 |
| L1-2 | 0.135516089 | 0.006816992 | 0.037530067 | 0.017723447 | 0.054374847 | 0.201745619 | 0.023145555 | 0.051618029 | 0.025052995 |
| L1-3 | 0.098848579 | 0.018083531 | 0.034430756 | 0.02285837 | 0.059893584 | 0.250891646 | 0.019318634 | 0.052939413 | 0.022330319 |
| L5-1 | 0.105955894 | 0.005962722 | 0.031899802 | 0.013821983 | 0.028432927 | 0.249387418 | 0.035503228 | 0.019777119 | 0.021764692 |
| L5-2 | 0.121154155 | 0.013448942 | 0.076326961 | 0.016663204 | 0.028199269 | 0.288099783 | 0.025663138 | 0.027540737 | 0.017835234 |
| L5-3 | 0.133549508 | 0 | 0.033496318 | 0.027228976 | 0.030625389 | 0.268284555 | 0.02169218 | 0.018430345 | 0.013386992 |
| L6-1 | 0.15876038 | 0.031155664 | 0.054663486 | 0.052163142 | 0.057507914 | 0.53887691 | 0.031421755 | 0.041813094 | 0.025040143 |
| L6-2 | 0.093675752 | 0.012510278 | 0.040865227 | 0.051211429 | 0.038302638 | 0.256957237 | 0.045097535 | 0.032945414 | 0.011935209 |
| L6-3 | 0.071376643 | 0.022250677 | 0.043113031 | 0.036570094 | 0.035069025 | 0.209706998 | 0.038718241 | 0.030824504 | 0.011397374 |
| L8-1 | 0.103255526 | 0.008384624 | 0.029868773 | 0.02544807 | 0.049680641 | 0.266372469 | 0.068253784 | 0.019904773 | 0.01133434 |
| L8-2 | 0.118109471 | 0 | 0.019297834 | 0.029306307 | 0.066920603 | 0.331581044 | 0.057359129 | 0.044008046 | 0.027868199 |
| L8-3 | 0.124515625 | 0.015603117 | 0.012114755 | 0.014950123 | 0.03513279 | 0.253756863 | 0.048407468 | 0.015431277 | 0.028044369 |
| L9-1 | 0.129534462 | 0 | 0.026156686 | 0.034716477 | 0.046012856 | 0.304158977 | 0.030937759 | 0.024231528 | 0.014319353 |
| L9-2 | 0.144547693 | 0 | 0.035112732 | 0.05168576 | 0.03290381 | 0.268932756 | 0.037800707 | 0.057284618 | 0.029325414 |
| L9-3 | 0.120590447 | 0.028951358 | 0.062156957 | 0.066242315 | 0.053761063 | 0.412516637 | 0.038147435 | 0.025147471 | 0.060423896 |
| L10-1 | 0.038961385 | 0.012172539 | 0.037961488 | 0.032111547 | 0.040829805 | 0.215305026 | 0.031651839 | 0.022425314 | 0.015532937 |
| L10-2 | 0.093046145 | 0.018624469 | 0.033077006 | 0.031254564 | 0.028879674 | 0.174998889 | 0.047345394 | 0.024847442 | 0.015474883 |
| L10-3 | 0.088938616 | 0.019000339 | 0.026863937 | 0.037419681 | 0.036959486 | 0.181754382 | 0.019034854 | 0.019069369 | 0.016549796 |
| L12-1 | 0.055795348 | 0.036864566 | 0.060257517 | 0.045606527 | 0.025350469 | 0.204736951 | 0.09180882 | 0.0263961 | 0.017398811 |
| L12-2 | 0.052547288 | 0.044763295 | 0.0263921 | 0.048519768 | 0.035982336 | 0.185294341 | 0.063919108 | 0.02089572 | 0 |
| L12-3 | 0.070567062 | 0.053266507 | 0.044957111 | 0.069195489 | 0.033208029 | 0.152781608 | 0.058665583 | 0.02508019 | 0.015065531 |
| L17-1 | 0.130361553 | 0.017724214 | 0.031390448 | 0.029287279 | 0.075932245 | 0.29107506 | 0.032830376 | 0.057553517 | 0.024731868 |
| L17-2 | 0.067094087 | 0.01980259 | 0.025500317 | 0.035950376 | 0.050022639 | 0.207983338 | 0.032799058 | 0.034570316 | 0.015582722 |
| L17-3 | 0.076112374 | 0.013059926 | 0.022606805 | 0.02962925 | 0.046439346 | 0.211844404 | 0.0309726 | 0.028093433 | 0.017572532 |
| L19-1 | 0.116209671 | 0.014262833 | 0.031481199 | 0.011841202 | 0.06166101 | 0.465062734 | 0.032844558 | 0.030632675 | 0.033573907 |
| L19-2 | 0.081494503 | 0.010023022 | 0.020642747 | 0.014716021 | 0.037068246 | 0.219591257 | 0.027718533 | 0.030818977 | 0.019929121 |
| L19-3 | 0.084539659 | 0.007668091 | 0.024111008 | 0.025199143 | 0.052207192 | 0.30176194 | 0.031844202 | 0.032458021 | 0.021906839 |
| L22-1 | 0.129600682 | 0.014393964 | 0.031066208 | 0.031538366 | 0.033147373 | 0.221804563 | 0.0347793 | 0.049205352 | 0.022979917 |
| L22-2 | 0.132725556 | 0.010794601 | 0.036996477 | 0.026996238 | 0.045239308 | 0.240382712 | 0.023845575 | 0.053911339 | 0.02326389 |
| L22-3 | 0.118948943 | 0.01517304 | 0.041876736 | 0.028786584 | 0.046982482 | 0.274439222 | 0.030463576 | 0.041342662 | 0.026415296 |

Responders

| L2-1 | 0.084268878 | 0.010877346 | 0.029725011 | 0.021274553 | 0.044478394 | 0.205368835 | 0.060052379 | 0.056176342 | 0.015399389 |
| L2-2 | 0.083682833 | 0.009932865 | 0.02363462 | 0.019202157 | 0.039700355 | 0.198299593 | 0.04080976 | 0.029295731 | 0.006993442 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | 42<br>Lauric<br>acid-TMS | 48<br>Citric<br>acid-4TMS | 49<br>Myristic<br>acid-TMS | 54<br>Palmitoleic<br>acid-TMS | 55<br>Palmitic<br>acid-TMS | 57<br>Margaric<br>acid-TMS | 59<br>Stearic<br>acid-TMS | 63<br>Pyruvic acid-<br>methyloxime-<br>TMS | 67<br>2-Oxoisocaproic<br>acid-methyloxime-<br>TMS |
|---|---|---|---|---|---|---|---|---|---|
| L2-3 | 0.098634334 | 0.01049054 | 0.017746421 | 0.031271575 | 0.044356191 | 0.22304339 | 0.053088035 | 0.028062885 | 0.013636931 |
| L3-1 | 0.090721354 | 0.017564301 | 0.029454985 | 0.037189364 | 0.033106968 | 0.204750187 | 0.041494487 | 0.034646018 | 0.016012208 |
| L3-2 | 0.070344856 | 0.013854947 | 0.024057087 | 0.029474562 | 0.038050944 | 0.231387398 | 0.028759434 | 0.03350294 | 0.017368846 |
| L3-3 | 0.0870224 | 0.02364481 | 0.032704866 | 0.030652197 | 0.040118317 | 0.247441614 | 0.037350381 | 0.024937507 | 0.016201556 |
| L4-1 | 0.122630233 | 0.018428578 | 0.03601743 | 0.037477494 | 0.050943368 | 0.220227558 | 0.045519193 | 0.038831646 | 0.02647581 |
| L4-2 | 0.103397785 | 0.014330192 | 0.055999106 | 0.019901974 | 0.053469055 | 0.164267384 | 0.024163655 | 0.020495372 | 0.016830943 |
| L4-3 | 0.053572642 | 0 | 0.050310886 | 0.019562041 | 0.02011416 | 0.158772764 | 0.042063061 | 0.022050829 | 0.010651672 |
| L7-1 | 0.046981198 | 0.012967797 | 0.037772618 | 0.028449759 | 0.021069663 | 0.107603845 | 0.045718101 | 0.02420347 | 0 |
| L7-2 | 0.050825191 | 0.006480259 | 0.019011287 | 0.03458033 | 0.026900023 | 0.11451616 | 0.033462391 | 0.02360304 | 0.0117604 |
| L7-3 | 0.055600719 | 0.000658695 | 0.033330274 | 0.014816369 | 0.022513013 | 0.119645456 | 0.058124746 | 0.017340396 | 0 |
| L13-1 | 0.12851203 | 0.015316245 | 0.039502626 | 0.041109665 | 0.051176293 | 0.2843426 | 0.048862055 | 0.028769583 | 0.022413251 |
| L13-2 | 0.13808022 | 0.021651241 | 0.05263497 | 0.036112248 | 0.037252634 | 0.244629068 | 0.021532048 | 0.020903869 | 0.023345714 |
| L13-3 | 0.152033608 | 0.019462324 | 0.036580105 | 0.030849483 | 0.050743238 | 0.252923053 | 0.038144586 | 0.026923027 | 0.015453068 |
| L15-1 | 0.084435193 | 0.012079036 | 0.01375668 | 0.015105008 | 0.038225426 | 0.140052193 | 0.033242202 | 0.021803156 | 0.0196595 |
| L15-2 | 0.071930196 | 0 | 0.031842844 | 0.024791242 | 0.04099165 | 0.10178162 | 0.067092195 | 0.015902182 | 0.019355832 |
| L16-1 | 0.232191087 | 0.008291415 | 0.034135193 | 0.016387663 | 0.033801522 | 0.299983002 | 0.043100246 | 0.022828147 | 0.019138876 |
| L16-2 | 0.257335231 | 0.007761218 | 0.027780773 | 0.013563258 | 0.035700163 | 0.257676739 | 0.030142571 | 0.029380469 | 0.01565116 |
| L16-3 | 0.152319843 | 0.007262199 | 0.034762999 | 0.008948749 | 0.024648476 | 0.21847274 | 0.036702771 | 0.02439047 | 0.021280154 |
| L18-1 | 0.119498859 | 0.011415768 | 0.041257606 | 0.023681269 | 0.048126287 | 0.229195434 | 0.039805977 | 0.01783935 | 0.018957154 |
| L18-2 | 0.123562166 | 0.015472447 | 0.089460779 | 0.019989774 | 0.04439622 | 0.19021890 | 0.041549741 | 0.027981657 | 0.015565048 |
| L18-3 | 0.11915020 | 0.006123582 | 0.025620328 | 0.017193332 | 0.062413236 | 0.26206464 | 0.04580604 | 0.02650815 | 0.0225354 |
| L21-1 | 0.122256827 | 0.013908709 | 0.030083308 | 0.030488275 | 0.052983261 | 0.379035213 | 0.056295318 | 0.025435822 | 0.031409094 |
| L21-2 | 0.113644812 | 0.015240729 | 0.074432986 | 0.018232798 | 0.038720209 | 0.278016554 | 0.039384686 | 0.022231184 | 0.025246298 |
| L21-3 | 0.096340765 | 0.010576951 | 0.040951702 | 0.016567464 | 0.042298208 | 0.31059838 | 0.031302273 | 0.038188325 | 0.021937498 |
| L23-1 | 0.101062269 | 0.013701453 | 0.02672845 | 0.01700504 | 0.065422253 | 0.254981921 | 0.043789695 | 0.023705887 | 0.025285863 |
| L23-2 | 0.132291341 | 0.018031677 | 0.031858914 | 0.021532771 | 0.060425133 | 0.299843701 | 0.042752944 | 0.027638845 | 0.022772741 |
| L23-3 | 0.146163637 | 0.013965538 | 0.02447201 | 0.025012032 | 0.067812695 | 0.323136916 | 0.052061547 | 0.030499296 | 0.023266901 |
| L24-1 | 0.121394404 | 0.0151241 | 0.032966019 | 0.02815021 | 0.067308464 | 0.466444084 | 0.032769386 | 0.041509495 | 0.028648132 |
| L24-2 | 0.09234996 | 0.013201028 | 0.030856168 | 0.02949808 | 0.062076573 | 0.344189362 | 0.049661259 | 0.029409622 | 0.024565256 |
| L24-3 | 0.078274835 | 0.009214321 | 0.029893789 | 0.032976952 | 0.058650442 | 0.358696162 | 0.040086985 | 0.030121524 | 0.026599611 |
| L25-1 | 0.076446862 | 0.024577795 | 0.030952583 | 0.03879656 | 0.0485017 | 0.250569 | 0.038552525 | 0.022112545 | 0.02467740 |
| L25-2 | 0.060660052 | 0.01537017 | 0.035383182 | 0.033024796 | 0.033601455 | 0.100723041 | 0.037919002 | 0.03095474 | 0.010919549 |
| L25-3 | 0.086789038 | 0.011820301 | 0.01650192 | 0.030892398 | 0.045339433 | 0.309828885 | 0.035976196 | 0.031753313 | 0.00897991 |

GCMS

Non-responders

| ID | 42 | 48 | 49 | 54 | 55 | 57 | 59 | 63 | 67 |
|---|---|---|---|---|---|---|---|---|---|
| L1-1 | 0.079926244 | 0.595380744 | 0.081893435 | 0.021498988 | 2.143806711 | 0.020557427 | 1.061879648 | 0.287988925 | 0.122509486 |
| L1-2 | 0.01786623 | 0.422448479 | 0.023332272 | 0.004239569 | 0.96364515 | 0.009332176 | 0.501817742 | 0.276219974 | 0.075078439 |
| L1-3 | 0.029154715 | 0.551813947 | 0.042615556 | 0.012543464 | 1.275580297 | 0.019117259 | 0.624855121 | 0.278788882 | 0.07469693 |
| L5-1 | 0.019921256 | 0.525579674 | 0.024093644 | 0.008515464 | 1.478637374 | 0.01802471 | 0.77304865 | 0.250661892 | 0.085772916 |
| L5-2 | 0.02092406 | 0.552919687 | 0.028505015 | 0 | 1.093852528 | 0.007263448 | 0.56074759 | 0.243448981 | 0.131020371 |
| L5-3 | 0.03306696 | 0.512441764 | 0.05675854 | 0 | 2.16186149 | 0.024332413 | 1.232340256 | 0.398085192 | 0.089588393 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | | | | | | |
|---|---|---|---|---|---|---|
| L6-1 | 0.048121301 | 0.482621462 | 0.06726155 | 0.040455109 | 1.597903381 | 0.01461669 | 0.721883745 | 0.774280864 | 0.053039409 |
| L6-2 | 0.039634377 | 0.548873318 | 0.053632773 | 0.015072867 | 1.656118686 | 0.0123993 | 0.859708329 | 0.808491856 | 0.029177197 |
| L6-3 | 0.046518172 | 0.730135502 | 0.05425713 | 0.010262327 | 1.490382586 | 0.016748981 | 0.784645907 | 0.656957792 | 0.047038793 |
| L8-1 | 0.094220571 | 0.598265784 | 0.102961329 | 0.053164557 | 2.694081214 | 0.031200403 | 1.242666357 | 0.252761971 | 0.063492432 |
| L8-2 | 0.126679817 | 0.605161641 | 0.166898254 | 0.074179161 | 3.029413194 | 0.079465179 | 1.260443287 | 0.199391719 | 0.071983131 |
| L8-3 | 0.119197161 | 0.766740383 | 0.122711299 | 0.01794874 | 3.368700972 | 0.027674912 | 1.677163257 | 0.271928996 | 0.073736758 |
| L9-1 | 0.035965443 | 0.369192707 | 0.074054923 | 0.017326418 | 3.660289251 | 0.051064405 | 2.303393278 | 0.418896773 | 0.06264171 |
| L9-2 | 0.029905836 | 0.427551463 | 0.044574179 | 0 | 1.589410392 | 0.029122548 | 0.944623204 | 0.544492469 | 0.052632469 |
| L9-3 | 0.05463673 | 1.11501731 | 0.045594367 | 0.012855207 | 1.023092729 | 0.005078551 | 0.570989131 | 0.688298424 | 0.055297093 |
| L10-1 | 0.067428098 | 0.884305842 | 0.057291869 | 0.020586483 | 0.99313676 | 0.01677609 | 0.45151056 | 0.211442834 | 0.051286534 |
| L10-2 | 0.109130625 | 0.905277462 | 0.174579791 | 0.086283425 | 3.226522565 | 0.040550924 | 1.500917571 | 0.35413161 | 0.067538306 |
| L10-3 | 0.07177906 | 1.12202095 | 0.113323247 | 0.058697991 | 2.943062259 | 0.041411881 | 1.568687119 | 0.448081271 | 0.057904153 |
| L12-1 | 0.164358578 | 0.836103445 | 0.231157367 | 0.119056014 | 4.445414422 | 0.042773597 | 2.07229443 | 0.536408623 | 0.120077328 |
| L12-2 | 0.213875516 | 0.892138281 | 0.251137182 | 0.14856336 | 4.377004283 | 0.037128994 | 2.02769986 | 0.418378757 | 0.165858004 |
| L12-3 | 0.13792653 | 1.005333895 | 0.16191817 | 0.061147477 | 4.464368133 | 0.054594406 | 2.35239989 | 0.440028157 | 0.118448744 |
| L17-1 | 0.034820096 | 0.695729957 | 0.043154229 | 0.035814956 | 1.19073384 | 0.019312499 | 0.519465219 | 0.152152475 | 0.058635646 |
| L17-2 | 0.08156117 | 0.828803767 | 0.110227293 | 0.071527665 | 1.743160373 | 0.033958164 | 0.797873766 | 0.500095988 | 0.068169881 |
| L17-3 | 0.029822597 | 0.638568369 | 0.054658344 | 0.023788765 | 1.292283335 | 0.013720218 | 0.665093152 | 0.299597623 | 0.062377563 |
| L19-1 | 0.043813401 | 0.366772176 | 0.058729311 | 0.009605484 | 1.714738578 | 0.007636717 | 0.85324346 | 0.195942338 | 0.093518801 |
| L19-2 | 0.023364203 | 0.271694036 | 0.034016184 | 0 | 1.351535506 | 0.014808752 | 0.742296264 | 0.40028787 | 0.079212511 |
| L19-3 | 0.016298763 | 0.288756694 | 0.043846229 | 0.008012202 | 1.50907476 | 0.018530833 | 0.737169084 | 0.66391533 | 0.096202226 |
| L22-1 | 0.0369109 | 0.447821882 | 0.052070393 | 0.009521103 | 1.790737439 | 0.014710264 | 0.917546425 | 0.719019744 | 0.086661746 |
| L22-2 | 0.025616892 | 0.570163282 | 0.034668649 | 0 | 1.232836877 | 0.01465029 | 0.694596533 | 0.360074258 | 0.071083387 |
| L22-3 | 0.017557958 | 0.713480026 | 0.039436018 | 0 | 1.485660115 | 0.019226661 | 0.761178167 | 0.271138646 | 0.080650502 |

Responders

| | | | | | | | | | |
|---|---|---|---|---|---|---|---|---|---|
| L2-1 | 0.065831515 | 0.489812309 | 0.096813619 | 0.056193802 | 2.944993453 | 0.035696203 | 1.328232213 | 0.352265849 | 0.088162375 |
| L2-2 | 0.022271184 | 0.612727131 | 0.059265403 | 0.00681718 | 1.800964255 | 0.019575417 | 0.946986703 | 0.274983799 | 0.076793074 |
| L2-3 | 0.039036867 | 0.587341456 | 0.065541434 | 0.013446251 | 2.115335302 | 0.021619205 | 1.178233511 | 0.295968755 | 0.071031712 |
| L3-1 | 0.05465367 | 0.712475871 | 0.134132132 | 0.095029825 | 2.328326348 | 0.036937203 | 0.984426899 | 0.326391667 | 0.059392553 |
| L3-2 | 0.028461036 | 0.636015661 | 0.088696359 | 0.051401701 | 2.053732295 | 0.026361957 | 0.919802851 | 0.243601154 | 0.053984391 |
| L3-3 | 0.044119345 | 0.662118012 | 0.056379479 | 0.017639542 | 1.579693744 | 0.018310106 | 0.805454661 | 0.329078981 | 0.083306325 |
| L4-1 | 0.019631428 | 0.57012089 | 0.071527998 | 0.021434617 | 3.070779054 | 0.031584283 | 1.556776058 | 0.243936574 | 0.104844689 |
| L4-2 | 0.017281772 | 0.355203197 | 0.023034656 | 0 | 1.001375606 | 0.007941523 | 0.561254923 | 0.318423872 | 0.063004293 |
| L4-3 | 0.038767328 | 0.44183202 | 0.067052868 | 0.023690201 | 3.091940745 | 0.031309459 | 1.607519027 | 0.545656089 | 0.061098464 |
| L7-1 | 0.038145533 | 0.60902924 | 0.11245517 | 0.055997305 | 2.791143885 | 0.00934094 | 1.374658663 | 0.363290789 | 0.05123964 |
| L7-2 | 0.048620892 | 0.76244734 | 0.15930953 | 0.107755795 | 3.083308596 | 0.036108813 | 1.322484478 | 0.476109571 | 0.047919812 |
| L7-3 | 0.075589705 | 0.734937784 | 0.189518402 | 0.123008641 | 3.634933853 | 0.04104003 | 1.388641221 | 0.457537336 | 0.052512882 |
| L13-1 | 0.029478835 | 0.997899179 | 0.080724514 | 0.014445392 | 2.572664031 | 0.035085514 | 1.394343942 | 0.379023208 | 0.067244243 |
| L13-2 | 0.015276028 | 0.980864697 | 0.029485763 | 0 | 1.022669214 | 0.005747034 | 0.597987894 | 0.185345064 | 0.05252222 |
| L13-3 | 0.029877674 | 0.891776231 | 0.041530664 | 0.004676013 | 1.360824338 | 0.008646048 | 0.694533902 | 0.267195133 | 0.044010302 |
| L15-1 | 0.026370076 | 0.486901951 | 0.063912017 | 0.01470131 | 2.647763142 | 0.03192494 | 1.453144029 | 0.161209146 | 0.061905058 |
| L15-3 | 0.028206411 | 0.527609959 | 0.085292646 | 0.026368954 | 3.408232963 | 0.038182553 | 1.635471582 | 0.057124716 | 0.085138723 |
| L16-1 | 0.105773771 | 0.382015752 | 0.115204704 | 0.042137007 | 2.900842992 | 0.026328547 | 1.390697499 | 0.398579694 | 0.05321113 |
| L16-2 | 0.020716951 | 0.452656213 | 0.027583058 | 0 | 1.15446944 | 0.00372026 | 0.642441171 | 0.525422571 | 0.056568097 |
| L16-3 | 0.037548435 | 0.41416511 | 0.058097591 | 0.01469837 | 1.707237832 | 0.02020379 | 0.966077887 | 0.226241382 | 0.047376292 |
| L18-1 | 0.040984477 | 0.663196921 | 0.072237748 | 0.009920403 | 1.882731692 | 0.011228624 | 0.873855009 | 0.198883207 | 0.053801294 |
| L18-2 | 0.034491922 | 0.52821316 | 0.045744976 | 0.011331969 | 1.50276797 | 0.01484044 | 0.825229389 | 0.1007702 | 0.054454166 |
| L18-3 | 0.024967351 | 0.682134153 | 0.057477351 | 0.011331969 | 1.368026777 | 0.015727992 | 0.67025718 | 0.130780384 | 0.052217549 |

TABLE 1-continued

L number represents patient number. With respect to numbers appearing after hyphen (-), "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| ID | 68<br>2-<br>Aminoethanol-<br>3TMS | 71<br>Malic acid-<br>3TMS | 72<br>Thereitol-<br>4TMS | 73<br>Erythrinol-<br>4TMS | 74<br>Threonic<br>acid-4TMS | 76<br>2-Oxoglutaric<br>acid-<br>methyloxime-<br>2TMS | 83<br>Pyrophosphate-<br>4TMS | 87<br>Arabitol-<br>5TMS | 88<br>Fucose-<br>methyloxime-<br>5TMS |
|---|---|---|---|---|---|---|---|---|---|
| L21-1 | 0.051401959 | 0.521578988 | 0.081779351 | 0.0337608 | 1.835814563 | 0.028217564 | 0.817591021 | 0.185455878 | 0.097635761 |
| L21-2 | 0.029198594 | 0.442783891 | 0.03175664 | 0.005331182 | 1.013980911 | 0.006510342 | 0.556524745 | 0.066163508 | 0.101749534 |
| L21-3 | 0.022439639 | 0.501146609 | 0.035744784 | 0.005542744 | 1.122781543 | 0.009978859 | 0.680231945 | 0.111177921 | 0.101461327 |
| L23-1 | 0.049229059 | 0.624128047 | 0.076288492 | 0.041316688 | 1.998701047 | 0.030219386 | 0.945294107 | 0.248231114 | 0.04455158 |
| L23-2 | 0.049807231 | 0.572361155 | 0.052802959 | 0.01876107 | 1.426268626 | 0.015312077 | 0.787506512 | 0.258523497 | 0.06730749 |
| L23-3 | 0.051076538 | 0.740753734 | 0.102031637 | 0.071217498 | 2.518780388 | 0.027922081 | 1.210189221 | 0.259502638 | 0.065581807 |
| L24-1 | 0.050751216 | 0.69314114 | 0.087613766 | 0.033828793 | 1.864624633 | 0.029005281 | 0.905588372 | 0.245292862 | 0.069278801 |
| L24-2 | 0.057107325 | 0.511754483 | 0.136854648 | 0.087380712 | 2.872605135 | 0.0248774 | 1.292155353 | 0.293097168 | 0.088874088 |
| L24-3 | 0.054482896 | 0.524149492 | 0.109276453 | 0.082289981 | 2.317237579 | 0.025503505 | 1.008399569 | 0.105759537 | 0.100114886 |
| L25-1 | 0.039722896 | 0.462779706 | 0.051451509 | 0.009397832 | 1.314192369 | 0.010533341 | 0.702182867 | 0.270410526 | 0.066980094 |
| L25-2 | 0.064282651 | 0.340553888 | 0.104286496 | 0.025143795 | 3.175845796 | 0.049067735 | 1.758845796 | 0.253116175 | 0.040617468 |
| L25-3 | 0.054306775 | 0.379072851 | 0.053552689 | 0.01332219 | 2.309307309 | 0.02548183 | 1.26688854 | 0.242532976 | 0.040494429 |

GCMS

Non-responders

| L1-1 | 0.146412819 | 0.023903333 | 0.007224243 | 0.087380273 | 0.100578948 | 0.021695147 | 0 | 0.059918062 | 0.083507541 |
| L1-2 | 0.150314307 | 0.029241308 | 0.014282001 | 0.075451873 | 0.094410195 | 0.018532553 | 0.007549215 | 0.068305381 | 0.110005455 |
| L1-3 | 0.193284794 | 0.033517853 | 0.012051212 | 0.068678036 | 0.092162908 | 0.020124137 | 0.008592026 | 0.076853886 | 0.11071184 |
| L5-1 | 0.202292537 | 0.034008754 | 0 | 0.279455162 | 0.142365668 | 0.018123336 | 0.008200639 | 0.19262777 | 0.077117108 |
| L5-2 | 0.25953597 | 0.034619953 | 0.00996029 | 0.11732056 | 0.201992842 | 0.011430229 | 0.005613199 | 0.251994214 | 0.139389212 |
| L5-3 | 0.194973309 | 0.034899742 | 0.017622896 | 0.094426679 | 0.082487968 | 0.014213666 | 0 | 0.240427563 | 0.10594244 |
| L6-1 | 0.207666193 | 0.082534294 | 0.030095885 | 0.176932605 | 0.162251686 | 0.030651007 | 0.00862045 | 0.326044869 | 0.127022067 |
| L6-2 | 0.178861666 | 0.036764075 | 0 | 0.095723805 | 0.09877066 | 0.024738066 | 0.01372095 | 0.334982874 | 0.086835455 |
| L6-3 | 0.1718705 | 0.07099204 | 0.031054327 | 0.459173479 | 0.164628741 | 0.024933515 | 0.015055791 | 0.518913544 | 0.102407519 |
| L8-1 | 0.174923547 | 0.020493168 | 0.019935741 | 0.103743274 | 0.010258197 | 0 | 0 | 0.511051756 | 0.070630589 |
| L8-2 | 0.173534928 | 0.0361345 | 0 | 0.084634594 | 0.011553448 | 0.033280538 | 0 | 0.582083896 | 0.080913004 |
| L8-3 | 0.224191705 | 0.023086771 | 0.013824568 | 0.12899207 | 0.025054345 | 0.011934323 | 0 | 1.166994596 | 0.069982043 |
| L9-1 | 0.118564246 | 0.026840832 | 0 | 0.073004837 | 0.064150703 | 0.014025011 | 0.008400687 | 0.626046652 | 0.085995672 |
| L9-2 | 0.164518728 | 0.023555002 | 0.019244099 | 0.092399849 | 0.073043047 | 0.02264774 | 0.007951222 | 0.498036144 | 0.103596928 |
| L9-3 | 0.350560732 | 0.136179949 | 0.040262492 | 0.295697909 | 0.071489748 | 0.069841129 | 0.011592606 | 0.547429964 | 0.170443076 |
| L10-1 | 0.15713259 | 0.052578247 | 0.013082242 | 0.081264649 | 0.23981521 | 0.026866996 | 0.005791668 | 0.476257074 | 0.062782461 |
| L10-2 | 0.158774709 | 0.01684127 | 0.021151758 | 0.095598834 | 0.157453915 | 0.02447914 | 0.011214051 | 0.704275436 | 0.045643601 |
| L10-3 | 0.155224087 | 0.058692238 | 0.013075317 | 0.080275427 | 0.179775539 | 0.031299076 | 0.010233607 | 0.60049241 | 0.063087109 |
| L12-1 | 0.199508797 | 0.051527715 | 0.013228446 | 0.130643063 | 0.097851593 | 0.030700208 | 0 | 1.140296911 | 0.140248277 |
| L12-2 | 0.200077707 | 0.066496721 | 0 | 0.2025700031 | 0.113367575 | 0.030997688 | 0 | 0.794132141 | 0.091969599 |
| L12-3 | 0.215300657 | 0.08638732 | 0.008164124 | 0.172056198 | 0.167069195 | 0.056307058 | 0 | 0.998650198 | 0.10201164 |
| L13-1 | 0.173332519 | 0.036216391 | 0.012331027 | 0.06287689 | 0.09219035 | 0.04167066 | 0 | 0.107252878 | 0.069142762 |
| L17-1 | 0.14788475 | 0.0360393 | 0.013253645 | 0.172453138 | 0.151824685 | 0.03819642 | 0.021410849 | 0.125813638 | 0.074237073 |
| L17-2 | 0.15076189 | 0.030778379 | 0.0086105 | 0.120381146 | 0.083718504 | 0.024675235 | 0.011837838 | 0.129767511 | 0.068739717 |
| L17-3 | 0.183328884 | 0.018233735 | 0.020855579 | 0.05979235 | 0.114874914 | 0.015893143 | 0.015673862 | 0.778759248 | 0.070956639 |
| L19-1 | 0.14465244 | 0.018235771 | 0.018570409 | 0.112595705 | 0.069907148 | 0.012196154 | 0.015913462 | 1.726076386 | 0.056856255 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | |
|---|---|---|---|---|---|---|
| L19-3 | 0.115077169 | 0.026784842 | 0.025575804 | 0.077810897 | 0.02480853 | 0.016396416 | 2.080349877 | 0.063944161 |
| L22-1 | 0.13341004 | 0.045643534 | 0.030277748 | 0.133698836 | 0.021237973 | 0.016974792 | 0.483430898 | 0.074151833 |
| L22-2 | 0.126705115 | 0.044495705 | 0.030728587 | 0.108890454 | 0.019693818 | 0.010025412 | 0.394619576 | 0.075922458 |
| L22-3 | 0.149017304 | 0.041086306 | 0.025502029 | 0.103920103 | 0.14436552 | 0.0334608 | 0.006270028 | 0.080319376 |
| Responders | | | | | | | | |
| L2-1 | 0.130318638 | 0 | 0 | 0.07021388 | 0.092797905 | 0.015154954 | 0.078734177 | 0.068223483 |
| L2-2 | 0.153218072 | 0.038995308 | 0.015801343 | 0.074626092 | 0.07233469 | 0.0139817 | 0.090930299 | 0.069203453 |
| L2-3 | 0.191344428 | 0.034828749 | 0 | 0.079671504 | 0.043067455 | 0.027699007 | 0.092973101 | 0.048301301 |
| L3-1 | 0.154648453 | 0.044588978 | 0.02801593 | 0.087273707 | 0.115185295 | 0.008981701 | 0.386892858 | 0.045415022 |
| L3-2 | 0.125095822 | 0.031192925 | 0.019483359 | 0.105669056 | 0.122790951 | 0.032646123 | 0.19138143 | 0.066532559 |
| L3-3 | 0.145925769 | 0.051245944 | 0.010803521 | 0.090108818 | 0.12922129 | 0.028656538 | 0.14726317 | 0.061255965 |
| L4-1 | 0.203372521 | 0.020372808 | 0.019185088 | 0.234056557 | 0.144743014 | 0.032093909 | 0.324368693 | 0.095441272 |
| L4-2 | 0.147544332 | 0.05975216 | 0.024583658 | 0.239952682 | 0.271687949 | 0.01587914 | 0.257450235 | 0.090732192 |
| L4-3 | 0.122298858 | 0.020063197 | 0 | 0.179880742 | 0.186913903 | 0.018352972 | 0.28552256 | 0.08665738 |
| L7-1 | 0.29221451 | 0.017196165 | 0.043155818 | 0.740529779 | 0.195683817 | 0.023375917 | 0.365281671 | 0.123603075 |
| L7-2 | 0.291276914 | 0.044540729 | 0.042254322 | 2.509793023 | 0.182622042 | 0.023174825 | 0.518155463 | 0.133483234 |
| L7-3 | 0.185270169 | 0.038378329 | 0.023050599 | 0.144990625 | 0.091087889 | 0.032742362 | 0.534634901 | 0.14803257 |
| L13-1 | 0.160412084 | 0.069560533 | 0.031875926 | 0.14844095 | 0.092027652 | 0.016573354 | 1.084427885 | 0.074808098 |
| L13-2 | 0.162501893 | 0.076315713 | 0.029012212 | 0.208845407 | 0.21564907 | 0.023333483 | 0.822241408 | 0.070459151 |
| L13-3 | 0.193904187 | 0.067263988 | 0.03937351 | 0.161634033 | 0.117462489 | 0.023799936 | 1.297373501 | 0.077618328 |
| L15-1 | 0.116378775 | 0.013887163 | 0.023126631 | 0.080955636 | 0.156841059 | 0.011217201 | 0.213098049 | 0.109985088 |
| L15-3 | 0.128179474 | 0.016365951 | 0.031179667 | 0.092267287 | 0.1887936 | 0.019529017 | 0.252001001 | 0.138107515 |
| L16-1 | 0.134192484 | 0.020221734 | 0.033788931 | 0.104986811 | 0.09180365 | 0.01085158 | 0.110035948 | 0.111364337 |
| L16-2 | 0.092494734 | 0.034956035 | 0.023772549 | 0.111809705 | 0.057660922 | 0.027656936 | 0.125081782 | 0.080815162 |
| L16-3 | 0.165205468 | 0.021910818 | 0.020238601 | 0.081040406 | 0.131402799 | 0.017424095 | 0.075975977 | 0.10434633 |
| L18-1 | 0.158900202 | 0.024829421 | 0.016908689 | 0.083536915 | 0.218593994 | 0.013970177 | 0.532085034 | 0.069384803 |
| L18-2 | 0.123385016 | 0.057211417 | 0.01357211 | 0.072885171 | 0.368564722 | 0.023615516 | 0.152445677 | 0.049287978 |
| L18-3 | 0.144929921 | 0.031317161 | 0.018345039 | 0.060058408 | 0.144909355 | 0.020388361 | 0.122281407 | 0.061647146 |
| L21-1 | 0.156081263 | 0.02792348 | 0.031105369 | 0.103093181 | 0.120309125 | 0.024005882 | 0.255591677 | 0.063097809 |
| L21-2 | 0.158468245 | 0.044220391 | 0.029482822 | 0.131439765 | 0.369437883 | 0.019477013 | 0.284042941 | 0.053142824 |
| L21-3 | 0.156856787 | 0.024326667 | 0.03447184 | 0.093673339 | 0.25168793 | 0.015364822 | 0.283361212 | 0.065991601 |
| L23-1 | 0.096172461 | 0.023499803 | 0.017960519 | 0.083732491 | 0.102323751 | 0.023961931 | 0.507909248 | 0.078711539 |
| L23-2 | 0.120100031 | 0.037694071 | 0.006903199 | 0.119151818 | 0.154454517 | 0.013420861 | 0.543680317 | 0.070443889 |
| L23-3 | 0.128312036 | 0.023127471 | 0.01416344 | 0.074284969 | 0.121416974 | 0.015886081 | 0.361651217 | 0.082497875 |
| L24-1 | 0.165247436 | 0.042865787 | 0.012255413 | 0.0796642 | 0.120302894 | 0.021894412 | 0.443666833 | 0.076293359 |
| L24-2 | 0.112742088 | 0.024138577 | 0.009673122 | 0.080631901 | 0.072941274 | 0.017264884 | 0.426501962 | 0.068877418 |
| L24-3 | 0.110788727 | 0.033627582 | 0.012315069 | 0.085900682 | 0.095994232 | 0.020392253 | 0.432035591 | 0.076463623 |
| L25-1 | 0.146396004 | 0.065192165 | 0.063105418 | 1.579503065 | 0.061945007 | 0.025832831 | 0.687042746 | 0.1009607 |
| L25-2 | 0.092234526 | 0.026127072 | 0.027827476 | 0.180235395 | 0.034932206 | 0.029646168 | 0.708011119 | 0.101284914 |
| L25-3 | 0.146927413 | 0.038734895 | 0.027191092 | 0.160450692 | 0.058429113 | 0.020391748 | 0.784293641 | 0.066793186 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | GCMS | | | | | | | | |
|---|---|---|---|---|---|---|---|---|---|
| ID | 91 Isocitric acid-4TMS | 92 Hypoxanthine-2TMS | 93 Ornithine-4TMS | 96 1,5-Anhydro-D-sorbitol-4TMS | 97 Fructose-methyloxime-5TMS(1) | 101 Mannose-methyloxime-5TMS | 104 Lysine-4TMS | 105 Glucose-methyloxime-5TMS(3) | 112 scyllo-Inositol-6TMS |
| Non-responders | | | | | | | | | |
| L1-1 | 0.040111642 | 0.025276444 | 0.119432597 | 0.287820789 | 0.742040162 | 2.289787981 | 2.799262443 | 3.014543763 | 0.021952956 |
| L1-2 | 0.028421218 | 0.033411831 | 0.107321859 | 0.246821239 | 0.033812942 | 1.752629594 | 2.936847716 | 1.857154363 | 0.005876086 |
| L1-3 | 0.025726854 | 0.024809476 | 0.112564496 | 0.271472235 | 0.030832845 | 1.664351593 | 3.29756604 | 1.855649481 | 0.014472195 |
| L5-1 | 0.026020528 | 0.016689552 | 0.099245936 | 0.57198507 | 0.0301360 2 | 1.594864928 | 2.427256314 | 1.718458644 | 0.02085056 |
| L5-2 | 0.021241567 | 0.027035079 | 0.084382215 | 0.741632139 | 0.259140067 | 1.975285462 | 2.32705899 | 2.280824576 | 0.018995504 |
| L5-3 | 0.026197235 | 0.007677174 | 0.103943043 | 0.645183823 | 0.694104981 | 1.132767692 | 2.837478452 | 2.126564433 | 0.02445417 |
| L6-1 | 0.029192091 | 0.099761435 | 0.214947011 | 0.307358811 | 0.116910584 | 0.933656008 | 3.845487911 | 1.744120751 | 0.075937056 |
| L6-2 | 0.027194721 | 0.085866917 | 0.169161156 | 0.255265162 | 0.117672281 | 2.212276215 | 2.85926946 | 1.873898415 | 0.061360896 |
| L6-3 | 0.037634787 | 0.051109954 | 0.109039572 | 0.30878 9111 | 0.15024366 | 2.122059782 | 2.547031758 | 2.389869939 | 0.074687979 |
| L8-1 | 0.023520303 | 0.027863585 | 0.142747648 | 0.128533271 | 0.07663002 | 1.725320327 | 2.569953161 | 2.0003793 6 | 0.013734371 |
| L8-2 | 0.041452489 | 0.187643932 | 0.125951046 | 0.127534908 | 0.02325265 | 2.184058379 | 2.768367456 | 1.799898944 | 0.016625694 |
| L8-3 | 0.029822918 | 0.036498922 | 0.140857656 | 0.148332718 | 0.03530463 | 2.021230893 | 2.597592515 | 2.124378152 | 0.015199292 |
| L9-1 | 0.016777509 | 0.023491695 | 0.174115382 | 0.243341501 | 0.022879145 | 1.581238465 | 4.400090689 | 1.676844015 | 0.046808375 |
| L9-2 | 0.03237404 | 0.064043684 | 0.224662876 | 0.210760917 | 0.058509949 | 1.330750548 | 4.15516435 | 2.326214238 | 0.056013569 |
| L9-3 | 0.088655491 | 0.099194589 | 0.070440262 | 0.181814526 | 0.205522471 | 1.88144419 | 3.634822854 | 2.546927336 | 0.133920134 |
| L10-1 | 0.025112237 | 0.023040415 | 0.11301737 | 0.347357653 | 0.045177603 | 1.149456768 | 2.142891367 | 1.527138935 | 0.039936288 |
| L10-2 | 0.032448359 | 0.01574 7931 | 0.112781859 | 0.411027362 | 0.03674094 | 1.299693055 | 2.283399267 | 1.910706688 | 0.03906503 |
| L10-3 | 0.029728657 | 0.025713448 | 0.111022268 | 0.430611083 | 0.026150634 | 1.336983201 | 2.029377758 | 1.882793849 | 0.050149851 |
| L12-1 | 0.055041521 | 0.038043941 | 0.13066738 | 0.44810291 | 0.045205296 | 1.734361132 | 2.876797938 | 2.08897589 | 0.07423979 |
| L12-2 | 0.060763428 | 0.039668701 | 0.134737121 | 0.480592093 | 0.051315341 | 1.488372313 | 2.689018612 | 2.031007164 | 0.068259353 |
| L12-3 | 0.065625045 | 0.01250381 | 0.088223341 | 0.487089798 | 0.033316884 | 1.117135227 | 2.101518164 | 1.758820883 | 0.066183834 |
| L17-1 | 0.024705687 | 0.06235328 | 0.089642112 | 0.230659138 | 0.00185105 | 1.26410912 | 2.344099346 | 1.811194792 | 0.051863617 |
| L17-2 | 0.030596758 | 0.02730779 7 | 0.091442543 | 0.299074527 | 0.031683419 | 1.525991126 | 2.236377796 | 1.727943494 | 0.040793263 |
| L17-3 | 0.022344147 | 0.02180424 | 0.082733537 | 0.348313336 | 0.018539258 | 1.166382729 | 2.325794084 | 1.835755013 | 0.034783909 |
| L19-1 | 0.012675425 | 0.096245519 | 0.147724239 | 0.573888338 | 0.028978529 | 1.182103768 | 4.497673709 | 1.733229731 | 0.04187800 3 |
| L19-2 | 0.016844804 | 0.017848719 | 0.11766366 | 0.526736793 | 0.019509815 | 1.408940084 | 3.167020792 | 1.742268041 | 0.04046301 |
| L19-3 | 0.018991197 | 0.013415672 | 0.111840667 | 0.465856301 | 0.031095528 | 1.295595846 | 4.039451841 | 1.886024915 | 0.06421387 |
| L22-1 | 0.024098429 | 0.029324263 | 0.11162198 | 0.043475271 | 0.058300137 | 2.179988723 | 2.904724796 | 3.3366033 | 0.041783751 |
| L22-2 | 0.034447953 | 0.017395989 | 0.121596666 | 0.07908684 | 0.0577864 9 | 2.187568359 | 3.157683607 | 2.622627119 | 0.050123817 |
| L22-3 | 0.043703269 | 0.03002471 7 | 0.114927366 | 0.110088656 | 0.052894681 | 2.090237129 | 3.015958129 | 2.251292459 | 0.053273873 |
| Responders | | | | | | | | | |
| L2-1 | 0.019746835 | 0.052911392 | 0.111844461 | 0.434264513 | 0.038035792 | 0.844050633 | 2.866817983 | 1.865691838 | 0.062435618 |
| L2-2 | 0.021431349 | 0.02718059 | 0.108489074 | 0.4333 13461 | 0.013312942 | 0.911609943 | 2.676777521 | 1.691894554 | 0.040866793 |
| L2-3 | 0.019870206 | 0.026760999 | 0.128847305 | 0.367888117 | 0.037149789 | 1.131917915 | 2.903798484 | 1.935010882 | 0.044612623 |
| L3-1 | 0.030046258 | 0.02664 3837 | 0.09780794 | 0.191611742 | 0.073213571 | 0.861889814 | 2.538045841 | 2.021159766 | 0.075096082 |
| L3-2 | 0.016200976 | 0.006657372 | 0.116277634 | 0.221576264 | 0.042490907 | 1.029767815 | 2.750760144 | 1.88827037 | 0.056597949 |
| L3-3 | 0.030514359 | 0.022225451 | 0.117635444 | 0.230036769 | 0.026215303 | 1.236481628 | 2.925746281 | 1.855825147 | 0.062213381 |
| L4-1 | 0.032227316 | 0.123689347 | 0.214364607 | 0.123878474 | 0.043226968 | 1.266436305 | 4.137699908 | 1.549082354 | 0.172121102 |
| L4-2 | 0.029897273 | 0.127218502 | 0.135657093 | 0.133268085 | 0.093456431 | 1.041456986 | 3.167450158 | 1.440151509 | 0.156210263 |

TABLE 1-continued

L number represents patient number. With respect to numbers appearing after hyphen (-), "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | | | | | GCMS | | | | |
|---|---|---|---|---|---|---|---|---|---|
| ID | 114<br>myo-Inositol-<br>6TMS | 116<br>Oleic acid-<br>TMS | 120<br>Sucrose-<br>8TMS | 122<br>Indoxyl<br>sulfate-<br>2TMS | 123<br>3-Methyl-2-<br>oxobutyric acid-<br>methyloxime-<br>TMS | 124<br>Maltose-<br>methyloxime-<br>8TMS | 127<br>Gluconic<br>acid-<br>methyloxime-<br>5TMS | 132<br>Ribitol-<br>5TMS | 136<br>Glycine-<br>3TMS |
| L4-3 | 0.027317206 | 0.084516852 | 0.105692783 | 0.157668524 | 0.015969013 | 0.841660438 | 3.52415738 | 1.673416689 | 0.107841805 |
| L7-1 | 0.033527758 | 0.063870611 | 0.087911559 | 0.09612169 | 0.017581109 | 2.167631031 | 1.529273779 | 1.631368115 | 0.024065007 |
| L7-2 | 0.044865531 | 0.075824086 | 0.097614431 | 0.088816184 | 0.509028782 | 1.95375394 | 1.713359061 | 2.668736223 | 0.044717578 |
| L7-3 | 0.045150389 | 0.036896692 | 0.115921696 | 0.048028636 | 0.029783524 | 1.975382538 | 1.419768707 | 2.120346939 | 0.0384119 |
| L13-1 | 0.040256767 | 0.020083494 | 0.142977062 | 0.132383175 | 0.045733267 | 2.312928132 | 2.154293685 | 2.186636441 | 0.0402029 |
| L13-2 | 0.040816316 | 0.018906582 | 0.122346748 | 0.140879644 | 0.160778427 | 1.377390705 | 1.377536835 | 1.681281228 | 0.058317575 |
| L13-3 | 0.042140768 | 0.018329273 | 0.143343981 | 0.130836845 | 0.034322719 | 1.408326465 | 2.77536835 | 1.801528747 | 0.045330742 |
| L15-1 | 0.016652169 | 0.007387846 | 0.137162918 | 0.061942339 | 0.023971666 | 1.446085498 | 3.674804275 | 1.818472723 | 0.125201939 |
| L15-3 | 0.016354331 | 0.053911571 | 0.10775041 | 0.083407088 | 0.033054989 | 1.558942933 | 3.333147343 | 1.930532574 | 0.158232963 |
| L16-1 | 0.030332601 | 0.035022885 | 0.16415364 | 0.444745938 | 0.07682622 | 1.205251859 | 2.633408672 | 1.964171268 | 0.055515333 |
| L16-2 | 0.034082494 | 0.013329595 | 0.17130578 | 0.373983564 | 0.056010899 | 1.011873692 | 2.178806376 | 1.927079064 | 0.031138336 |
| L16-3 | 0.021413931 | 0 | 0.118665284 | 0.345919552 | 0.052799052 | 1.648571688 | 2.270258907 | 1.713405923 | 0.039555095 |
| L18-1 | 0.032072389 | 0.007905558 | 0.162926321 | 0.443237283 | 0.053750714 | 2.108745682 | 2.464723407 | 2.563418964 | 0.019488238 |
| L18-2 | 0.025276092 | 0.029342491 | 0.111532066 | 0.504797143 | 0.12391244 | 1.853670026 | 1.759269175 | 2.0123844 | 0.013407038 |
| L18-3 | 0.025748866 | 0.005758372 | 0.161655372 | 0.453155267 | 0.034268409 | 2.027152509 | 2.377456374 | 2.255200675 | 0.011676453 |
| L21-1 | 0.027026766 | 0.027099082 | 0.121726512 | 0.178455724 | 0.032464903 | 1.497676257 | 3.686998612 | 2.074123534 | 0.049343374 |
| L21-2 | 0.029916844 | 0.022861094 | 0.082303009 | 0.203199478 | 0.090960419 | 1.132791765 | 2.341960016 | 1.492097329 | 0.051710165 |
| L21-3 | 0.023645418 | 0.028622054 | 0.111241888 | 0.18268668 | 0.082287206 | 1.356360403 | 2.66644065 | 1.827826304 | 0.059726029 |
| L23-1 | 0.029332601 | 0 | 0.118123513 | 0.163318325 | 0.08569341 | 2.133048979 | 2.26945775 | 2.013595289 | 0.031012496 |
| L23-2 | 0.024538918 | 0.01774211 | 0.148004585 | 0.189027821 | 0.200401167 | 2.814207565 | 2.614483693 | 2.619214338 | 0.03372408 |
| L23-3 | 0.023928072 | 0.031461816 | 0.197375109 | 0.257923925 | 0.043160484 | 2.233096301 | 2.914929408 | 2.534131236 | 0.036018045 |
| L24-1 | 0.025530105 | 0.024157691 | 0.165761088 | 0.653457519 | 0.034964446 | 1.39240991 | 3.618180067 | 2.056108445 | 0.013740188 |
| L24-2 | 0.020678315 | 0.012914186 | 0.133847082 | 0.630631381 | 0.033957395 | 2.028613502 | 4.534602616 | 2.059412432 | 0.016328272 |
| L24-3 | 0.030093081 | 0.0101154697 | 0.12132777753 | 0.631778856 | 0.04207099044 | 1.527332302 | 3.290215939 | 1.929380319 | 0.005984619 |
| L25-1 | 0.030006325 | 0.053498414 | 0.182373712 | 0.230119876 | 0.028467411 | 1.626644632 | 3.48766628 | 1.403011091 | 0.067612592 |
| L25-2 | 0.0282488 | 0.019406781 | 0.18700044 | 0.383514956 | 0.018497435 | 1.41842498 | 1.543034999 | 1.649524626 | 0.028160163 |
| L25-3 | 0.035561449 | 0.015974059 | 0.195138658 | 0.399439463 | 0.017444528 | 1.884624811 | 2.671457209 | 1.522625728 | 0.03495818 |
| Non-responders | | | | | | | | | |
| L1-1 | 0.112780016 | 0.126449472 | 0.038138847 | 0.06347694 | 0.136403123 | 0.008305918 | 0.041495962 | 0.010631799 | 2.808224092 |
| L1-2 | 0.068916787 | 0.020934243 | 0.006670547 | 0.037929128 | 0.098128805 | 0 | 0.038939595 | 0.01413921 | 3.852629228 |
| L1-3 | 0.059705634 | 0.043076482 | 0 | 0.053252664 | 0.097309174 | 0.004476389 | 0.035500284 | 0.013988893 | 4.469419993 |
| L5-1 | 0.063845121 | 0.061057207 | 0.005613758 | 0.029525334 | 0.107378299 | 0 | 0.042455943 | 0.005056176 | 4.290546128 |
| L5-2 | 0.067715091 | 0.02957121 | 0.004758676 | 0.024167762 | 0.147993242 | 0.010744258 | 0.043467013 | 0.007537836 | 4.594799167 |
| L5-3 | 0.067152845 | 0.056418899 | 0.052708479 | 0.0137779 | 0.094984203 | 0.009586855 | 0.033156677 | 0.01222067 | 4.623933815 |
| L6-1 | 0.106744047 | 0.197577648 | 0.034270771 | 0.006721108 | 0.107702895 | 0.006913795 | 0.039941276 | 0.010405102 | 7.625911823 |
| L6-2 | 0.085342292 | 0.089196265 | 0.019189152 | 0.00846966 | 0.107351302 | 0.010709403 | 0.034125819 | 0.006840297 | 4.457694578 |
| L6-3 | 0.116825433 | 0.067708846 | 0.009319581 | 0.011439587 | 0.10580328 | 0.005222969 | 0.062146177 | 0.013559592 | 4.746640589 |
| L8-1 | 0.102496806 | 0.325808075 | 0.014090504 | 0.097015445 | 0.134626253 | 0.007896876 | 0.041102466 | 0.015917625 | 5.120396392 |
| L8-2 | 0.064063821 | 0.473030618 | 0.035398832 | 0.112395907 | 0.104486314 | 0.031686959 | 0.043318143 | 0.01679882 | 4.063315616 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L8-3 | 0.117392836 | 0.257803707 | 0.064861196 | 0.128820229 | 0.112667222 | 0.011384433 | 0.044480913 | 0.018197909 | 5.343749731 |
| L9-1 | 0.110346528 | 0.077038121 | 0.052090626 | 0 | 0.115596958 | 0.010938395 | 0.020985808 | 0.01619678 | 4.245998536 |
| L9-2 | 0.101224522 | 0.026919197 | 0.081011175 | 0.023645165 | 0.12013051 | 0.019897778 | 0.026879751 | 0.01021656 | 3.751258051 |
| L9-3 | 0.230754384 | 0.02836831 | 0.144121467 | 0.029015694 | 0.102335007 | 0.035155794 | 0.066608228 | 0.008528587 | 5.71464416 |
| L10-1 | 0.103738523 | 0.113871515 | 0.003648524 | 0.037916165 | 0.099154397 | 0.004924051 | 0.063170946 | 0.009417531 | 8.157695894 |
| L10-2 | 0.11036252 | 0.508232739 | 0.032626158 | 0.076739416 | 0.113112058 | 0.009823407 | 0.054019215 | 0.014592237 | 6.935382681 |
| L10-3 | 0.118022998 | 0.021261052 | 0.00591927 | 0.039105149 | 0.108888109 | 0.00991147 | 0.068097493 | 0.021289814 | 7.229235097 |
| L12-1 | 0.136625044 | 0.832443737 | 0.042469634 | 0.025362627 | 0.175629506 | 0.016000584 | 0.05237881 | 0.026031345 | 4.025557163 |
| L12-2 | 0.126445169 | 0.951821387 | 0.07863614 | 0 | 0.185862932 | 0.009808195 | 0.026411053 | 0.012831204 | 3.503856942 |
| L12-3 | 0.135270468 | 0.511516858 | 0.007612592 | 0 | 0.146591387 | 0.016865267 | 0.035269017 | 0.008309264 | 3.5282007 |
| L17-1 | 0.059142675 | 0.159142675 | 0 | 0 | 0.091343846 | 0.041007227 | 0.019050694 | 0 | 3.755316828 |
| L17-2 | 0.076522684 | 0.323060762 | 0 | 0.016683872 | 0.101218872 | 0.008910622 | 0.034794893 | 0.009486553 | 3.717855655 |
| L17-3 | 0.068812678 | 0.135505853 | 0.008022005 | 0 | 0.104778547 | 0.004804448 | 0.027892792 | 0.010659526 | 3.356970097 |
| L19-1 | 0.070751659 | 0.111900313 | 0.099863664 | 0 | 0.111342575 | 0.005424834 | 0.03588113 | 0.011250095 | 4.80231771 |
| L19-2 | 0.079293147 | 0.021130594 | 0.028936132 | 0.12761411 | 0.100847078 | 0.004947002 | 0.020812082 | 0.00483008 | 2.94173262 |
| L19-3 | 0.091672983 | 0.046282906 | 0.018279725 | 0.089041 | 0.113803029 | 0.008649272 | 0.032299916 | 0.005891735 | 3.76853432 |
| L22-1 | 0.097017149 | 0.071300545 | 0.006344346 | 0.026935965 | 0.145108574 | 0.008067954 | 0.052890941 | 0.005872187 | 2.884046079 |
| L22-2 | 0.129979845 | 0.025704521 | 0 | 0.035129512 | 0.124842187 | 0.007594518 | 0.050818358 | 0.009493147 | 3.139911138 |
| L22-3 | 0.11319626 | 0.056691946 | 0 | 0.037289041 | 0.115728477 | 0.011242256 | 0.047949156 | 0.015023499 | 3.456291391 |
| Responders | | | | | | | | |
| L2-1 | 0.061955478 | 0.366826713 | 0 | 0.063814928 | 0.126102139 | 0.012256656 | 0.030816237 | 0.007175906 | 4.870170231 |
| L2-2 | 0.060338526 | 0.052443019 | 0.005661111 | 0.05172244 | 0.123517976 | 0.005681848 | 0.026677726 | 0.013592887 | 4.975380388 |
| L2-3 | 0.062628627 | 0.088857036 | 0 | 0.076337886 | 0.145798129 | 0 | 0.027977408 | 0.009080329 | 5.053475971 |
| L3-1 | 0.099373076 | 0.44996348 | 0 | 0.058944751 | 0.095768916 | 0.004669322 | 0.050001739 | 0.01356451 | 4.754108481 |
| L3-2 | 0.10838551 | 0.313524137 | 0 | 0.031403862 | 0.082023553 | 0.009600198 | 0.043576459 | 0.006783992 | 4.999115094 |
| L3-3 | 0.114662613 | 0.083861627 | 0.021659197 | 0.024989662 | 0.105986268 | 0.005167063 | 0.045754775 | 0.013094613 | 5.20360167 |
| L4-1 | 0.162354561 | 0.20795697 | 0.020425764 | 0.343130135 | 0.144909446 | 0.015977486 | 0.042046813 | 0.012724494 | 4.895132616 |
| L4-2 | 0.177453164 | 0.023443468 | 0.043283421 | 0.227718652 | 0.083079662 | 0.036139518 | 0.073207666 | 0.00042502 | 4.491484344 |
| L4-3 | 0.118323593 | 0.195577942 | 0.097597853 | 0.199103017 | 0.110373063 | 0.014550489 | 0.071469829 | 0.007780647 | 3.692953248 |
| L7-1 | 0.066414849 | 0.300605084 | 0.064580351 | 0.062168437 | 0.097132168 | 0.015247387 | 0.061885744 | 0.014026393 | 2.967592537 |
| L7-2 | 0.113821395 | 0.552110505 | 0.364700904 | 0.056206459 | 0.091765776 | 0.013870028 | 0.060311886 | 0.01340264 | 3.77229405 |
| L7-3 | 0.088753983 | 0.744293076 | 0.047799179 | 0.040994139 | 0.130554499 | 0.017091271 | 0.054328871 | 0.013478962 | 4.190560793 |
| L13-1 | 0.178825695 | 0.17176011 | 0.069416887 | 0.111002379 | 0.114081788 | 0.010005836 | 0.19776451 | 0.015159133 | 4.916362167 |
| L13-2 | 0.198378976 | 0.047590208 | 0.087726024 | 0.256831851 | 0.08204664 | 0.02450543 | 0.234990545 | 0.027098682 | 4.548319862 |
| L13-3 | 0.173753317 | 0.064405214 | 0.119558633 | 0.309000702 | 0.088582772 | 0.028496224 | 0.232000837 | 0.018651757 | 4.192039012 |
| L15-1 | 0.139002113 | 0.091400522 | 0.013458432 | 0.369355039 | 0.080992917 | 0.007226296 | 0.052634522 | 0 | 4.394122033 |
| L15-3 | 0.130238196 | 0.297658445 | 0.02813907 | 0.388213337 | 0.101723939 | 0 | 0.049034132 | 0.006783992 | 3.63537538 |
| L16-1 | 0.166867079 | 0.314557508 | 0.077109526 | 0.055332758 | 0.093427936 | 0 | 0.070524242 | 0 | 3.805475985 |
| L16-2 | 0.13895779 | 0.035074664 | 0.013192992 | 0.039241061 | 0.080380188 | 0.018736205 | 0.070929405 | 0 | 3.646745559 |
| L16-3 | 0.115163184 | 0.047428847 | 0.018040831 | 0.037276102 | 0.099028681 | 0.008380195 | 0.069903441 | 0.008862749 | 3.311710773 |
| L18-1 | 0.071493963 | 0.148951236 | 0.00937236 | 0.035815264 | 0.1013086 | 0.006474162 | 0.046882034 | 0.0069194 | 4.380043397 |
| L18-2 | 0.068681883 | 0.05188081 | 0.0011313447 | 0.026121581 | 0.071685381 | 0 | 0.101945832 | 0.010254573 | 3.047927143 |
| L18-3 | 0.069009841 | 0.09656339 | 0.006308678 | 0.037744095 | 0.094252322 | 0.007110759 | 0.045785474 | 0.010586445 | 4.098481187 |
| L21-1 | 0.11159268 | 0.307408979 | 0.009097308 | 0.078505862 | 0.116505322 | 0.025826327 | 0.0570474 | 0.016261378 | 3.873683855 |
| L21-2 | 0.101626625 | 0.050273665 | 0.039004436 | 0.091148624 | 0.08513376 | 0.006034069 | 0.073637917 | 0.012774865 | 3.105840103 |
| L21-3 | 0.127812551 | 0.038882368 | 0.007874343 | 0.087487726 | 0.096606228 | 0.007404185 | 0.069762458 | 0.010452215 | 3.240026738 |
| L23-1 | 0.078330596 | 0.228984132 | 0.088097721 | 0.054493565 | 0.086842483 | 0.014981671 | 0.044707704 | 0.010191783 | 4.31306634 |
| L23-2 | 0.084203397 | 0.08646452 | 0.123752214 | 0.083229134 | 0.107590914 | 0.008257789 | 0.057127227 | 0.008513077 | 4.004866104 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| ID | 137 Benzoic acid-TMS | 139 3-Methyl-2-oxovaleric acid-methyloxime-TMS(2) | 152 Linoleic acid-TMS | 154 Hypotaurine-3TMS | 156 Elaidic acid-TMS | 3 Quinolinic acid | 6 Nicotinamide | 9 Kynurenine | 10 Kynurenic acid |
|---|---|---|---|---|---|---|---|---|---|
| L23-3 | 0.089500884 | | 0.319448755 | 0.076718256 | 0.095352467 | 0.103425942 | 0.005743637 | 0.040142489 | 0.009620704 | 4.542033796 |
| L24-1 | 0.085543107 | | 0.191897141 | 0.00791345 | 0.022054929 | 0.068588581 | 0.010943193 | 0.044635548 | 0.011998587 | 4.519121495 |
| L24-2 | 0.084440791 | | 0.43147121 | 0.005520808 | 0.039597881 | 0.087885442 | 0 | 0.036038755 | 0.011858551 | 2.765779313 |
| L24-3 | 0.074324166 | | 0.278281869 | 0.008276477 | 0.093086915 | 0.006588357 | 0.034881949 | 0.014905864 | 3.254390284 |
| L25-1 | 0.19072568 | | 0.050360823 | 0 | 0.131096513 | 0.095681579 | 0.025469269 | 0.051232376 | 0.009547241 | 3.782086847 |
| L25-2 | 0.110592776 | | 0.169618962 | 0.035153997 | 0.136571986 | 0.090542798 | 0.06270793 | 0.063158906 | 0.01200485 | 2.836731676 |
| L25-3 | 0.110297676 | | 0.047758793 | 0.154876738 | 0.135785789 | 0.11059931 | 0.01779015 | 0.073385156 | 0.01324678 | 4.756122237 |

LCMS

| ID | 137 Benzoic acid-TMS | 139 3-Methyl-2-oxovaleric acid-methyloxime-TMS(2) | 152 Linoleic acid-TMS | 154 Hypotaurine-3TMS | 156 Elaidic acid-TMS | 3 Quinolinic acid | 6 Nicotinamide | 9 Kynurenine | 10 Kynurenic acid |
|---|---|---|---|---|---|---|---|---|---|
| Non-responders | | | | | | | | | |
| L1-1 | 0.049566489 | 0.02532128 | 0.021033812 | 0.020288409 | 0.011405225 | 248815 | 207168 | 4548449 | 163962 |
| L1-2 | 0.029731897 | 0.01664708 | 0.005674725 | 0.018536214 | 0.003767285 | 307636 | 155647 | 5176997 | 112830 |
| L1-3 | 0.038068942 | 0.019640835 | 0.013832268 | 0.016727601 | 0.006685671 | 349830 | 189413 | 6027523 | 117153 |
| L5-1 | 0.032491522 | 0.017603684 | 0.009706491 | 0.027750173 | 0.005939963 | 355033 | 151940 | 4324578 | 270255 |
| L5-2 | 0.044599844 | 0.036250603 | 0.010822655 | 0.019834348 | 0.004515646 | 563034 | 104962 | 5235589 | 353783 |
| L5-3 | 0.052849462 | 0.021448666 | 0.012970451 | 0.016885938 | 0.008196249 | 430806 | 141511 | 5252615 | 193734 |
| L6-1 | 0.038468597 | 0.014391889 | 0.045088774 | 0.037679497 | 0.013093545 | 780218 | 327716 | 4219365 | 178439 |
| L6-2 | 0.047761013 | 0.007889546 | 0.025192068 | 0.032355211 | 0.01457718 | 1868400 | 447283 | 7054021 | 259329 |
| L6-3 | 0.044651442 | 0.008268959 | 0.013076494 | 0.02873733 | 0.012419855 | 2007629 | 273758 | 8650642 | 345132 |
| L8-1 | 0.095350908 | 0.022451903 | 0.061092401 | 0.037099834 | 0.015066001 | 221935 | 156055 | 4595986 | 232044 |
| L8-2 | 0.063296182 | 0.024583872 | 0.114038071 | 0.045135211 | 0.031910449 | 294546 | 198090 | 4228765 | 198216 |
| L8-3 | 0.079905831 | 0.025011384 | 0.059671613 | 0.041662729 | 0.026978958 | 365102 | 137884 | 5214993 | 195449 |
| L9-1 | 0.056028448 | 0.031263922 | 0.033014065 | 0.048097117 | 0.012799911 | 600626 | 131732 | 6152177 | 460473 |
| L9-2 | 0.043109035 | 0.011997279 | 0.018663676 | 0.057935162 | 0.009996788 | 247167 | 159577 | 4906158 | 347368 |
| L9-3 | 0.059165316 | 0.016675178 | 0.010712002 | 0.163370099 | 0.011596627 | 821880 | 102314 | 12015007 | 1852832 |
| L10-1 | 0.033247867 | 0.00976393 | 0.033435634 | 0.021068853 | 0.012198438 | 394333 | 183012 | 5681817 | 384037 |
| L10-2 | 0.05977864 | 0.016516278 | 0.133952667 | 0.013220642 | 0.038563382 | 695927 | 125706 | 7522110 | 462176 |
| L10-3 | 0.060228142 | 0.016193144 | 0.080620574 | 0.011102227 | 0.017211328 | 889626 | 28590 | 8852644 | 430690 |
| L12-1 | 0.119177599 | 0.018590344 | 0.195532968 | 0.032232179 | 0.050105171 | 1909554 | 85349 | 24649953 | 2161274 |
| L12-2 | 0.094007051 | 0.030438573 | 0.277188128 | 0.028467458 | 0.095712824 | 2662472 | 145637 | 25162670 | 2516580 |
| L12-3 | 0.077889374 | 0.021437176 | 0.123289162 | 0.03780171 | 0.040660968 | 3924392 | 82959 | 31805783 | 2799400 |
| L17-1 | 0.03149517 | 0.015341787 | 0.05773678 | 0.042011013 | 0.019164143 | 158668 | 123011 | 2080952 | 167338 |
| L17-2 | 0.022729331 | 0.013702798 | 0.086900299 | 0.02600742 | 0.030680069 | 326892 | 132636 | 3361666 | 181464 |
| L17-3 | 0.042050773 | 0.014854754 | 0.028932479 | 0.032500246 | 0.01026554 | 311692 | 108618 | 3199629 | 204509 |
| L19-1 | 0.031152277 | 0.020235871 | 0.024006559 | 0.043617954 | 0.01860556 | 178206 | 178260 | 3872078 | 428243 |
| L19-2 | 0.040079991 | 0.007168517 | 0.008555451 | 0.023493221 | 0.006854037 | 181095 | 188140 | 3312913 | 382838 |
| L19-3 | 0.044971564 | 0.024580673 | 0.015280381 | 0.034899348 | 0.005203514 | 101904 | 78175 | 2109093 | 162105 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | | | | | | |
|---|---|---|---|---|---|---|
| L22-1 | 0.048870716 | 0.01963355 | 0.020215726 | 0.019097214 | 0.02872375 | 552131 | 182361 | 4966801 | 204166 |
| L22-2 | 0.027421402 | 0.01637365 | 0.008743432 | 0.021297105 | 0.007967753 | 1257633 | 253388 | 7901764 | 282789 |
| L22-3 | 0.044616535 | 0.016337321 | 0.014371929 | 0.012721641 | 0.009447768 | 1396925 | 177517 | 7931848 | 355068 |
| Responders | | | | | | | | | |
| L2-1 | 0.090964644 | 0.020113488 | 0.093688346 | 0.032151899 | 0.009454387 | 275639 | 215612 | 4497329 | 182348 |
| L2-2 | 0.041716996 | 0.01628347 | 0.017595065 | 0.033977034 | 0.009632183 | 573335 | 200208 | 5773398 | 186230 |
| L2-3 | 0.04555945 | 0.014458829 | 0.034381637 | 0.029410798 | 0.009192107 | 670490 | 154256 | 5952703 | 213094 |
| L3-1 | 0.03282027 | 0.014464463 | 0.102633776 | 0.051875554 | 0.042458654 | 180382 | 136365 | 2813187 | 272341 |
| L3-2 | 0.046112846 | 0.012944318 | 0.079656945 | 0.031872039 | 0.034063723 | 314964 | 121146 | 3994459 | 260224 |
| L3-3 | 0.034887923 | 0.018731071 | 0.021662923 | 0.032302528 | 0.006191535 | 511465 | 139446 | 5108326 | 287099 |
| L4-1 | 0.082625997 | 0.020032379 | 0.042780627 | 0.044096954 | 0.008866294 | 325651 | 181007 | 3625575 | 280179 |
| L4-2 | 0.043445257 | 0.014179915 | 0.006662248 | 0.029754703 | 0.007193995 | 278810 | 73660 | 2888629 | 173700 |
| L4-3 | 0.074349348 | 0 | 0.063188027 | 0.027639984 | 0.028243069 | 284699 | 152456 | 3559581 | 132819 |
| L7-1 | 0.059744493 | 0.007205668 | 0.066685513 | 0.026332567 | 0.023493606 | 3208592 | 219773 | 11619897 | 2073278 |
| L7-2 | 0.058492866 | 0.014116354 | 0.10594529 | 0.047105042 | 0.047105042 | 2598621 | 199483 | 11457335 | 1416607 |
| L7-3 | 0.063028571 | 0.015308062 | 0.146373923 | 0.007486855 | 0.034339885 | 2038053 | 102800 | 10684978 | 1227093 |
| L13-1 | 0.059532253 | 0.020743368 | 0.035534408 | 0.041221888 | 0.01297751 | 510175 | 90081 | 4330929 | 296703 |
| L13-2 | 0.035093766 | 0.010811124 | 0.010569517 | 0.032681423 | 0.004587319 | 666499 | 108425 | 5125621 | 373427 |
| L13-3 | 0.038244817 | 0.010389203 | 0.013287198 | 0.040410687 | 0.008733206 | 828958 | 115124 | 6370872 | 571229 |
| L15-1 | 0.059525289 | 0.021082391 | 0.053628681 | 0.023008575 | 0.016894495 | 290858 | 146736 | 2843362 | 97176 |
| L15-3 | 0.082454689 | 0.02419479 | 0.101570016 | 0.012891061 | 0.061819371 | 274437 | 130057 | 2446176 | 110020 |
| L16-1 | 0.02442725 | 0.012087711 | 0.087037818 | 0.023168114 | 0.024540573 | 264428 | 119269 | 4656859 | 201884 |
| L16-2 | 0.031943576 | 0.01231226 | 0.017258734 | 0.019516281 | 0.004241888 | 327566 | 119432 | 5899018 | 253685 |
| L16-3 | 0.040515425 | 0.011117853 | 0.016965834 | 0.026483137 | 0.005030984 | 565119 | 74156 | 7983943 | 268218 |
| L18-1 | 0.032477024 | 0.013712072 | 0.038187437 | 0.025092434 | 0.018324912 | 275371 | 84851 | 4431991 | 182515 |
| L18-2 | 0.03082084 | 0.015246983 | 0.017223817 | 0.018552442 | 0.010004952 | 285921 | 94545 | 4876541 | 260117 |
| L18-3 | 0.035132189 | 0.009085113 | 0.023913334 | 0.026237313 | 0.026720619 | 218860 | 89021 | 4180872 | 221839 |
| L21-1 | 0.048692533 | 0.015321274 | 0.085848311 | 0.036344021 | 0.022576944 | 364618 | 147625 | 7227481 | 436761 |
| L21-2 | 0.028361276 | 0.027566208 | 0.018732116 | 0.025350003 | 0.010835206 | 435088 | 157430 | 8365158 | 397598 |
| L21-3 | 0.035648834 | 0.025286173 | 0.009620643 | 0.049671261 | 0.006003307 | 544622 | 231589 | 10034716 | 595874 |
| L23-1 | 0.0579845 | 0.019040898 | 0.041785061 | 0.046893442 | 0.018204073 | 571435 | 70676 | 5573960 | 228646 |
| L23-2 | 0.049833281 | 0.016932375 | 0.020902365 | 0.039501928 | 0.007085548 | 432513 | 57655 | 5406838 | 287552 |
| L23-3 | 0.045827655 | 0.016695677 | 0.059446866 | 0.044878628 | 0.018818619 | 399572 | 89551 | 5805400 | 255676 |
| L24-1 | 0.051597939 | 0.016099777 | 0.056894974 | 0.032420264 | 0.012969711 | 391653 | 276401 | 4587495 | 323748 |
| L24-2 | 0.06826248 | 0.021973962 | 0.093333403 | 0.026157497 | 0.03027859 | 594610 | 87580 | 4641103 | 350390 |
| L24-3 | 0.041904059 | 0.018540011 | 0.071106187 | 0.015392371 | 0.042290919 | 457509 | 136520 | 5262739 | 315963 |
| L25-1 | 0.050052044 | 0.01479648 | 0.014916007 | 0.0726676 | 0.024642539 | 394512 | 123199 | 4517445 | 904292 |
| L25-2 | 0.059418018 | 0 | 0.0428206 | 0.033364877 | 0.043522941 | 503837 | 69621 | 6016451 | 399259 |
| L25-3 | 0.063362093 | 0.010029347 | 0.017036064 | 0.024778016 | 0.011041079 | 662459 | 80959 | 5483825 | 542900 |

TABLE 1-continued

L number represents patient number. With respect to numbers appearing after hyphen (-). "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| ID | 13 Indoleacetate | 14 Indolelactate | 17 5-OH-Trp | 18 5-HIAA | 19 3-OH-Kynurenine | 20 3-OH-Anthralinic acid | 21 3-Indole-propionate | 23 Serotonin | 24 Tryptophan |
|---|---|---|---|---|---|---|---|---|---|
| Non-responders | | | | | | | | | |
| L1-1 | 1287229 | 408566 | 40972 | 25215 | 18566 | 18545 | 445181 | | 68800111 |
| L1-2 | 1066612 | 293346 | 24312 | 39626 | 25922 | 18577 | 1866273 | | 73260786 |
| L1-3 | 629449 | 330093 | 32080 | 40292 | 38894 | 12004 | 2353832 | 11327 | 77143255 |
| L5-1 | 780247 | 518113 | 44531 | 39966 | 14082 | 8326 | 118548 | | 72509216 |
| L5-2 | 1641298 | 625760 | 24822 | 38145 | 18324 | 22448 | 213465 | | 78281214 |
| L5-3 | 2587398 | 497039 | 30224 | 54617 | 11174 | 23505 | 85989 | | 67909314 |
| L6-1 | 672017 | 375495 | 43557 | 48080 | 28994 | 40429 | 96475 | 7701 | 54146198 |
| L6-2 | 352304 | 175583 | 16212 | 16214 | 119253 | 67259 | 13250 | | 20899368 |
| L6-3 | 674585 | 248375 | 28005 | 32243 | 117456 | 122645 | 94258 | | 30667491 |
| L8-1 | 1233689 | 338427 | 20156 | 52570 | 31279 | 5372 | 593200 | | 46190259 |
| L8-2 | 1217254 | 337818 | 12601 | 56578 | 39110 | 9669 | 523761 | | 42113673 |
| L8-3 | 942712 | 442444 | 12536 | 58495 | 27168 | 6758 | 959183 | 7628 | 48843772 |
| L9-1 | 887242 | 397087 | 41255 | 65263 | 27425 | 72418 | 1330 | | 59705028 |
| L9-2 | 6526060 | 372654 | 59596 | 73768 | 16957 | 47135 | 60805 | | 71966159 |
| L9-3 | 865530 | 657719 | 95607 | 181374 | 39055 | 30190 | 59106 | | 52632532 |
| L10-1 | 754166 | 255803 | 31029 | 45749 | 64110 | 12352 | 595639 | 5640 | 37426324 |
| L10-2 | 860061 | 329206 | 32515 | 34466 | 85883 | 25084 | 257984 | | 37195618 |
| L10-3 | 1288427 | 274433 | 22633 | 53816 | 128352 | 32821 | 384220 | | 34151151 |
| L12-1 | 924129 | 291358 | 16148 | 51728 | 585672 | 205764 | 20584 | | 32810796 |
| L12-2 | 1055247 | 398377 | 7555 | 50744 | 619400 | 449882 | 11119 | 6748 | 28933948 |
| L12-3 | 1427291 | 437675 | 7887 | 68420 | 1816011 | 582635 | 1026 | 9000 | 23321444 |
| L17-1 | 1137705 | 185296 | 45192 | 33211 | 7533 | 21386 | 17899 | 7386 | 61111824 |
| L17-2 | 827482 | 199432 | 35084 | 26296 | 20200 | 27623 | 8461 | 16746 | 42320271 |
| L17-3 | 1439931 | 242256 | 51398 | 34079 | 11517 | 25465 | 14619 | | 69383133 |
| L19-1 | 2239025 | 664525 | 85805 | 38371 | 20217 | 19047 | 555028 | | 98827251 |
| L19-2 | 1383245 | 499507 | 75998 | 32282 | 21674 | 34455 | 523619 | 21984 | 73422099 |
| L19-3 | 1126520 | 402749 | 43183 | 17729 | 8927 | 26109 | 1012074 | 6864 | 83204874 |
| L22-1 | 1534391 | 468955 | 55824 | 26331 | 20372 | 33403 | 2749 | 27100 | 77340483 |
| L22-2 | 1557776 | 446559 | 44159 | 65214 | 28037 | 63590 | 14700 | 6819 | 69804944 |
| L22-3 | 1430039 | 413197 | 47320 | 53623 | 42293 | 59575 | 22326 | 6143 | 66933136 |
| Responders | | | | | | | | | |
| L2-1 | 1503405 | 336392 | 48497 | 47301 | 24268 | 15316 | 523166 | 9656 | 55921244 |
| L2-2 | 1091539 | 300699 | 36165 | 39235 | 31862 | 14188 | 310980 | 24248 | 52980076 |
| L2-3 | 1563581 | 371917 | 33558 | 39769 | 51251 | 22532 | 843845 | 6484 | 52514899 |
| L3-1 | 1786756 | 235068 | 44464 | 31120 | 13691 | 14971 | 1224640 | | 44639048 |
| L3-2 | 1493850 | 268527 | 42691 | 32743 | 18753 | 19236 | 1602896 | | 46829850 |
| L3-3 | 1129354 | 225082 | 38248 | 34011 | 24305 | 12698 | 2013047 | | 48983718 |
| L4-1 | 1189506 | 561687 | 48113 | 70892 | 19353 | | 1026960 | 13012 | 56658846 |
| L4-2 | 948733 | 421030 | 49989 | 84497 | 16854 | 14800 | 916950 | | 55523996 |

TABLE 1-continued

L number represents patient number. With respect to numbers appearing after hyphen (-), "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | 25 N-Formyl-kynurenine | 27 Tyrosine | 32 Histidine | 35 Adenosine | 36 Guanosine | 37 Inosine | 39 Uridine | 40 Xanthosine | 41 GSSG |
|---|---|---|---|---|---|---|---|---|---|
| L4-3 | 62776 | 44006119 | 1529238 | 30880 | 8017 | 40439 | 333912 | 13868 | 39344 |
| L7-1 | 80081 | 38233560 | 1638276 | 21735 | 5285 | 28057 | 549927 | 11518 | 40880 |
| L7-2 | 79043 | 44978268 | 1682181 | 35316 | 15082 | 42701 | 534038 | 19098 | 107823 |
| L7-3 | 50558 | 46645215 | 1689027 | 17586 | 8829 | 7658 | 328321 | 9874 | 102930 |
| L13-1 | 50376 | 50056696 | 1874430 | 33696 | 13221 | 22527 | 787869 | 32674 | 82569 |
| L13-2 | 62163 | 44515980 | 1581224 | 16171 | 4118 | 6467 | 218350 | 11987 | 62231 |
| L13-3 | 65477 | 47805310 | 1620146 | 30535 | 8143 | 28783 | 707128 | 18806 | 125473 |
| L15-1 | 92638 | 43158576 | 1545682 | 21944 | 5352 | 8617 | 500449 | 3397 | 166285 |
| L15-3 | 100095 | 33246576 | 1111917 | 31843 | 6223 | 27583 | 422189 | 21859 | 142223 |
| L16-1 | 45397 | 35378094 | 1246477 | 79425 | 10067 | 58647 | 612699 | 142308 | 28583 |
| L16-2 | 32027 | 36559407 | 1400037 | 245558 | 77771 | 1541983 | 1439944 | 173826 | 50243 |
| L16-3 | 40343 | 37623163 | 1525906 | 81429 | 15172 | 67695 | 895959 | 200392 | 30462 |
| L18-1 | 52966 | 39553246 | 1248723 | 37393 | 15913 | 32966 | 428493 | 33378 | 34077 |

| | 25 N-Formyl-kynurenine | 27 Tyrosine | 32 Histidine |  |  |  |  |  |  | 36 Guanosine | 37 Inosine | 39 Uridine | 40 Xanthosine | 41 GSSG |

| ID | 25 N-Formyl-kynurenine | 27 Tyrosine | 32 Histidine | 35 Adenosine | 36 Guanosine | 37 Inosine | 39 Uridine | 40 Xanthosine | 41 GSSG |
|---|---|---|---|---|---|---|---|---|---|
| L4-3 | 1443071 | 511815 | 43352 | 89625 | 9350 | 5458 | 1165961 | | 71793350 |
| L7-1 | 1352791 | 864387 | 31199 | 134777 | 166707 | 36842 | 1306977 | | 34519338 |
| L7-2 | 501893 | 747059 | 26278 | 105498 | 175761 | 35373 | 215880 | | 25075193 |
| L7-3 | 824015 | 625921 | 15028 | 106271 | 203335 | 24782 | 355179 | | 29130284 |
| L13-1 | 2390110 | 529499 | 33361 | 94711 | 23814 | 12344 | 265166 | | 49267460 |
| L13-2 | 2098009 | 667029 | 37921 | 126596 | 29808 | 9465 | 743006 | 6919 | 49208813 |
| L13-3 | 1892187 | 692340 | 39608 | 109714 | 41275 | 15048 | 1217593 | | 50516275 |
| L15-1 | 505233 | 391806 | 40177 | 38219 | 24191 | | 1043064 | | 44469085 |
| L15-3 | 290107 | 307249 | 14662 | 37180 | 25450 | | 1869619 | | 29279555 |
| L16-1 | 2974904 | 664578 | 37670 | 71299 | 32790 | 10621 | 286931 | 10560 | 54224590 |
| L16-2 | 3301587 | 676095 | 35609 | 39077 | 35413 | 11718 | 446413 | | 53834012 |
| L16-3 | 2478805 | 626847 | 36968 | 46413 | 66843 | 18606 | 466742 | | 56219557 |
| L18-1 | 1042484 | 338461 | 29007 | 24502 | 31503 | 11763 | 1814 | | 59910385 |
| L18-2 | 1357998 | 480744 | 39552 | 28803 | 68748 | 15774 | 2583 | 12499 | 59131437 |
| L18-3 | 1212763 | 389436 | 32807 | 28062 | 27827 | 13855 | 6906 | | 54105082 |
| L21-1 | 2223269 | 580237 | 30350 | 51124 | 38566 | 46988 | 1505 | 19341 | 61483694 |
| L21-2 | 2285051 | 563768 | 23327 | 62756 | 69415 | 37101 | 2651 | | 74823594 |
| L21-3 | 1794258 | 742432 | 38703 | 72035 | 41548 | 52188 | 6113 | | 72473034 |
| L23-1 | 998696 | 389018 | 47452 | 46779 | 24923 | 16491 | 1089573 | | 69682120 |
| L23-2 | 1149781 | 550199 | 45351 | 44146 | 30633 | 32922 | 1827736 | | 80434945 |
| L23-3 | 1092693 | 546671 | 46077 | 49297 | 23253 | 25673 | 1912874 | | 91518264 |
| L24-1 | 1404231 | 501683 | 44376 | 41482 | 16014 | 16285 | 158709 | | 68894895 |
| L24-2 | 1540368 | 359715 | 63458 | 27601 | 27980 | 39583 | 65621 | | 56616761 |
| L24-3 | 1500132 | 404843 | 51070 | 35446 | 47844 | 15546 | 400066 | 8329 | 62245519 |
| L25-1 | 2453587 | 989785 | 62380 | 178279 | 33334 | 18239 | 3397881 | | 71226863 |
| L25-2 | 3476286 | 506316 | 23156 | 78165 | 63268 | 14695 | 2140836 | | 40878040 |
| L25-3 | 3159711 | 615132 | 44542 | 119519 | 44180 | 10103 | 2431096 | 9322 | 56018287 |

LCMS

Non-responders

| ID |
|---|
| L1-1 |
| L1-2 |
| L1-3 |
| L5-1 |
| L5-2 |
| L5-3 |
| L6-1 |
| L6-2 |
| L6-3 |
| L8-1 |
| L8-2 |
| L8-3 |
| L9-1 |

TABLE 1-continued

L number represents patient number. With respect to numbers appearing after hyphen (-), "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L9-2 | 79951 | 49355339 | 1543732 | 41358 | 4721 | 37293 | 183958 | 17863 | 112191 |
| L9-3 | 78556 | 53729577 | 1818155 | 32734 | 12848 | 37273 | 245241 | 88626 | 78801 |
| L10-1 | 51578 | 30511994 | 1688317 | 26087 | 6123 | 16912 | 775368 | 13398 | 79463 |
| L10-2 | 50497 | 32555723 | 1334200 | 23923 | 11410 | 25210 | 862989 | 20935 | 77323 |
| L10-3 | 55976 | 28932724 | 1345567 | 27345 | 11146 | 19629 | 989647 | 25163 | 25834 |
| L12-1 | 170874 | 42684870 | 1104339 | 49608 | 19037 | 75438 | 611715 | 34084 | 58908 |
| L12-2 | 176664 | 43507054 | 1433263 | 100463 | 27903 | 112113 | 882398 | 25854 | 105482 |
| L12-3 | 158576 | 45231570 | 1438705 | 53334 | 463018 | 1312508 | 1362078 | 64880 | 14705 |
| L17-1 | 52701 | 33030109 | 1445573 | 27919 | 9938 | 93026 | 847030 | 19981 | 167807 |
| L17-2 | 50308 | 27975576 | 1566254 | 34383 | 17210 | 32600 | 580974 | 12693 | 100241 |
| L17-3 | 67406 | 39404954 | 1718859 | 38674 | 11304 | 30417 | 752032 | 19271 | 64527 |
| L19-1 | 108270 | 57525566 | 2104915 | 32875 | 20000 | 162396 | 1970045 | 17629 | 192953 |
| L19-2 | 84974 | 41354045 | 1536886 | 54048 | 34476 | 60213 | 945358 | 10576 | 42027 |
| L19-3 | 87935 | 36304842 | 1990332 | 36364 | 16946 | 21031 | 953664 | 12459 | 47059 |
| L21-1 | 67900 | 49360171 | 1151741 | 91225 | 31292 | 57497 | 866570 | 18568 | 55270 |
| L22-2 | 109567 | 46424858 | 1379508 | 33901 | 10666 | 25729 | 908220 | 27270 | 32155 |
| L22-3 | 80163 | 51758418 | 1577671 | 94372 | 18796 | 80322 | 1691797 | 19991 | 36175 |
| Responders | | | | | | | | |
| L2-1 | 53782 | 30262172 | 1738369 | 32710 | 16220 | 77591 | 845985 | 11282 | 83390 |
| L2-2 | 53595 | 28593103 | 1841744 | 53321 | 11979 | 41071 | 771331 | 11282 | 58866 |
| L2-3 | 54896 | 29142963 | 1869801 | 35245 | 11555 | 39866 | 860531 | 16924 | 68311 |
| L3-1 | 33269 | 31245442 | 1594843 | 24013 | 9089 | 15593 | 867573 | 12223 | 99125 |
| L3-2 | 45204 | 29836349 | 1696867 | 19958 | 7371 | 5196 | 755067 | 20919 | 105314 |
| L3-3 | 45797 | 33014960 | 1572130 | 20701 | 9102 | 8735 | 687834 | 15983 | 111215 |
| L4-1 | 66168 | 39066221 | 1702189 | 39172 | 21960 | 170898 | 666134 | 16923 | 28792 |
| L4-2 | 36756 | 39990147 | 1455695 | 36029 | 13538 | 43851 | 662346 | 26089 | 15755 |
| L4-3 | 57316 | 34106577 | 1281497 | 55012 | 11944 | 51986 | 999540 | 35258 | 79433 |
| L7-1 | 66755 | 44602514 | 888302 | 31499 | 8829 | 39137 | 410553 | 36677 | 18063 |
| L7-2 | 69768 | 30903974 | 858471 | 30205 | 10350 | 60481 | 471342 | 31731 | 49067 |
| L7-3 | 63056 | 26439665 | 895215 | 52331 | 16010 | 49442 | 1040667 | 34082 | 17857 |
| L13-1 | 42693 | 30180019 | 1362028 | 27819 | 11937 | 17437 | 698880 | 34082 | 35937 |
| L13-2 | 41867 | 34950138 | 1600049 | 37992 | 10577 | 13456 | 874515 | 33147 | 105319 |
| L13-3 | 51442 | 42414780 | 1560015 | 42279 | 15025 | 22594 | 969006 | 27974 | 37410 |
| L15-1 | 53289 | 25070445 | 1780169 | 21400 | 11272 | 4579 | 585600 | 5644 | 108955 |
| L15-2 | 56049 | 19079743 | 1727929 | 137990 | 32409 | 169310 | 1790460 | 10107 | 90157 |
| L16-1 | 86360 | 36617430 | 1374499 | 47432 | 14877 | 57489 | 1104316 | 15042 | 66469 |
| L16-2 | 69654 | 39935996 | 1795295 | 28290 | 8973 | 17372 | 526189 | 19224 | 88968 |
| L16-3 | 73833 | 40852502 | 1613137 | 35575 | 15433 | 19165 | 843859 | 21390 | 43543 |
| L18-1 | 89100 | 36006336 | 1332654 | 84946 | 26770 | 38572 | 1013596 | 17393 | 79245 |
| L18-2 | 79090 | 35978636 | 1852199 | 1702015 | 289782 | 809547 | 2361299 | 22329 | 27321 |
| L18-3 | 63745 | 31638833 | 1553407 | 37298 | 7796 | 3304 | 921361 | 14335 | 104859 |
| L21-1 | 161170 | 35413909 | 1683744 | 71776 | 26552 | 62168 | 1282183 | 24444 | 103018 |
| L21-2 | 147096 | 36882214 | 2025685 | 1043831 | 122110 | 613632 | 3278795 | 41841 | 65572 |
| L21-3 | 164501 | 38787821 | 1569175 | 32117 | 8774 | 26959 | 1181190 | 25386 | 226888 |
| L23-1 | 91034 | 42496009 | 1484500 | 78270 | 11986 | 47669 | 704427 | 24916 | 34879 |
| L23-2 | 72084 | 54562531 | 1801625 | 80844 | 8261 | 46199 | 780923 | 22565 | 30040 |
| L23-3 | 76140 | 48429463 | 1414435 | 37437 | 12526 | 21376 | 478630 | 17631 | 94128 |
| L24-1 | 99117 | 49476266 | 1767009 | 63787 | 4912 | 33700 | 779489 | 23034 | 424684 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | LCMS | | | | |
|---|---|---|---|---|---|---|---|---|---|---|
| | | 42 | 43 | 44 Aminoadipic | 45 | 47 | 49 | 53 | 59 3- | 62 |
| ID | | GSH | AC_C0 | acid | Choline | AC_C6 | AC_C5:1 | AC_C2 | Methylhistidine | Phenylalanine |
| L24-2 | | 83530 | 47483510 | 1495171 | 43007 | 14494 | 28774 | 728555 | 20214 | 75904 |
| L24-3 | | 71001 | 4274302 | 1740698 | 221883 | 54129 | 394956 | 1885633 | 20450 | 60542 |
| L25-1 | | 78689 | 39142086 | 1605873 | 50848 | 12348 | 51394 | 1287410 | 35963 | 67795 |
| L25-2 | | 67986 | 33783263 | 1159830 | 34982 | 10393 | 12409 | 631050 | 30494 | 39019 |
| L25-3 | | 63385 | 41650372 | 1640021 | 99455 | 22213 | 40878 | 896289 | 41374 | 37626 |
| Non-responders | | | | | | | | | | |
| L1-1 | | 525923 | 7688359 | 896475 | 3905525 | 1147651 | 125627 | 32750932 | 38102 | 47193615 |
| L1-2 | | 418049 | 6566173 | 451387 | 2770264 | 558393 | 65879 | 18232577 | 64922 | 40607558 |
| L1-3 | | 694515 | 6199093 | 486805 | 2126353 | 1084093 | 63882 | 26261007 | 52397 | 42564603 |
| L5-1 | | 634916 | 6834732 | 437478 | 3051047 | 935642 | 112776 | 32411806 | 589653 | 51011358 |
| L5-2 | | 866254 | 7261132 | 369854 | 3271105 | 549183 | 109758 | 28065759 | 235657 | 56551206 |
| L5-3 | | 725785 | 7217687 | 359675 | 3069745 | 522008 | 101761 | 18857048 | 282153 | 47016205 |
| L6-1 | | 550825 | 6754727 | 341744 | 3200804 | 613994 | 80196 | 24878516 | 79926 | 52089088 |
| L6-2 | | 294526 | 5927813 | 253253 | 2792252 | 1278513 | 81890 | 30404385 | 148093 | 44745361 |
| L6-3 | | 423344 | 5725648 | 342781 | 3863904 | 1356785 | 96043 | 37403574 | 116056 | 41116162 |
| L8-1 | | 291121 | 5478022 | 369581 | 3546036 | 811926 | 66998 | 23633875 | 126722 | 34015541 |
| L8-2 | | 275082 | 5640775 | 378860 | 3011823 | 932292 | 76570 | 31582703 | 775207 | 44883420 |
| L8-3 | | 368441 | 6014266 | 309668 | 3561912 | 942236 | 66241 | 25009092 | 207367 | 43994705 |
| L9-1 | | 270590 | 7426575 | 606877 | 3499944 | 1416996 | 193337 | 23923081 | 159801 | 57061414 |
| L9-2 | | 249989 | 8214793 | 1442859 | 3113573 | 490547 | 197920 | 21920058 | 172178 | 85508843 |
| L9-3 | | 287104 | 12493548 | 882456 | 3693041 | 4115049 | 576312 | 73907268 | 218663 | 102984840 |
| L10-1 | | 515114 | 5415264 | 296721 | 3780447 | 1301390 | 89701 | 32036020 | 156295 | 43742994 |
| L10-2 | | 283929 | 4962600 | 275612 | 3768770 | 1288494 | 111747 | 30981104 | 557622 | 42373862 |
| L10-3 | | 412226 | 5204137 | 236716 | 2698552 | 1079337 | 73021 | 36637081 | 159848 | 40326957 |
| L12-1 | | 267303 | 7219576 | 510042 | 3782152 | 1726755 | 256725 | 49360013 | 244834 | 47868487 |
| L12-2 | | 367064 | 7709626 | 523353 | 4372541 | 1792180 | 239155 | 52063337 | 535302 | 52824745 |
| L12-3 | | 250003 | 6952957 | 462370 | 4880587 | 833273 | 292403 | 37859690 | 670076 | 67983468 |
| L17-1 | | 721600 | 4613567 | 522253 | 3710267 | 523277 | 129638 | 31728578 | 229366 | 42403700 |
| L17-2 | | 518429 | 4554120 | 557347 | 4181240 | 1383026 | 91262 | 33346766 | 103145 | 39538293 |
| L17-3 | | 606126 | 4967830 | 678778 | 3783036 | 620812 | 152567 | 34926162 | 293750 | 46123806 |
| L19-1 | | 1077258 | 6283476 | 641672 | 3529615 | 355925 | 197408 | 19277360 | 808578 | 61626326 |
| L19-2 | | 445794 | 6570661 | 678466 | 2736894 | 242872 | 147988 | 17578833 | 1212924 | 47837316 |
| L19-3 | | 555864 | 7060993 | 674413 | 2866157 | 216842 | 136091 | 15890209 | 133476 | 43565395 |
| L22-1 | | 342727 | 5769657 | 598972 | 4415733 | 630337 | 229620 | 24633489 | 594575 | 49646989 |
| L22-2 | | 403416 | 6578562 | 588815 | 4689391 | 785322 | 264341 | 25470883 | 135374 | 48747317 |
| L22-3 | | 534222 | 7104760 | 555845 | 4174172 | 562969 | 268988 | 31869745 | 177852 | 61440631 |
| Responders | | | | | | | | | | |
| L2-1 | | 444657 | 5766920 | 391763 | 4036359 | 873302 | 84801 | 24482198 | 78048 | 33768961 |
| L2-2 | | 633813 | 5412477 | 325930 | 3615673 | 832150 | 65348 | 22220790 | 824846 | 36007924 |
| L2-3 | | 565409 | 7059111 | 427416 | 3590622 | 694572 | 74092 | 23134194 | 180897 | 35825971 |

TABLE 1-continued

L number represents patient number. With respect to numbers appearing after hyphen (-), "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| ID | 66 Cysteine | 68 Arginine | 69 Glutamine | 70 Glutamic acid | 71 Alanine | 74 Citrulline | 75 Creatinine | 77 Pyroglutamic acid | 78 Taurine |
|---|---|---|---|---|---|---|---|---|---|
| L3-1 | 724783 | 5460241 | 330710 | 2385094 | 1289054 | 107184 | 30181027 | 250179 | 39708672 |
| L3-2 | 781662 | 5248330 | 281570 | 2240887 | 642381 | 93212 | 31624294 | 159016 | 32524669 |
| L3-3 | 757910 | 5854146 | 361480 | 2452958 | 1213075 | 88909 | 34751955 | 247130 | 40667303 |
| L4-1 | 185501 | 7521718 | 474559 | 5149121 | 1058407 | 185851 | 32513884 | 391339 | 55671945 |
| L4-2 | 123205 | 7968742 | 512848 | 4301942 | 359220 | 154335 | 25214276 | 568566 | 50510755 |
| L4-3 | 262743 | 6481311 | 403482 | 3514710 | 520569 | 158169 | 27786543 | 2516720 | 50321705 |
| L7-1 | 193188 | 4819218 | 248531 | 2665764 | 1279077 | 219284 | 42028810 | 377100 | 44662156 |
| L7-2 | 194174 | 4262377 | 266133 | 2352768 | 1172387 | 115638 | 30234922 | 161132 | 36414651 |
| L7-3 | 151049 | 3888917 | 180766 | 3606597 | 1004821 | 104638 | 31098724 | 379934 | 37566409 |
| L13-1 | 524671 | 4456396 | 287084 | 5346628 | 603190 | 122432 | 26743107 | 509540 | 43255839 |
| L13-2 | 633621 | 4470959 | 348524 | 5675313 | 427765 | 131784 | 20302015 | 579711 | 51312048 |
| L13-3 | 585163 | 5011272 | 472241 | 5676928 | 574929 | 225280 | 27128049 | 726862 | 53916077 |
| L15-1 | 778335 | 7294689 | 304810 | 3467621 | 241572 | 128087 | 18908557 | 166928 | 51368549 |
| L15-3 | 748758 | 6371737 | 214325 | 2987567 | 286665 | 113208 | 22022671 | 83563 | 48880761 |
| L16-2 | 316022 | 7217080 | 314201 | 3065952 | 531297 | 122679 | 22831701 | 327544 | 59538671 |
| L16-2 | 451801 | 7168236 | 283349 | 4338406 | 524118 | 138419 | 24482851 | 747473 | 64062314 |
| L16-3 | 332724 | 6989793 | 277393 | 4206038 | 1112465 | 106712 | 30673823 | 248565 | 59550459 |
| L18-1 | 616453 | 5249379 | 334552 | 3023082 | 1081673 | 71800 | 27140624 | 570686 | 36633847 |
| L18-2 | 291938 | 5604821 | 323855 | 3221867 | 781222 | 82603 | 27500047 | 265906 | 45205047 |
| L18-3 | 800244 | 7055385 | 307262 | 2826504 | 1118764 | 91221 | 29895496 | 114725 | 33645443 |
| L21-1 | 745543 | 5436544 | 379742 | 3147264 | 857519 | 175431 | 32286252 | 1338688 | 50469649 |
| L21-2 | 127566 | 6480711 | 347086 | 3228125 | 462094 | 147617 | 29980989 | 372232 | 70294229 |
| L21-3 | 1521411 | 5351390 | 533508 | 3217634 | 974232 | 177127 | 33622343 | 361227 | 53753064 |
| L23-1 | 400061 | 5274300 | 177500 | 2807480 | 700960 | 85213 | 31141899 | 115183 | 40823126 |
| L23-2 | 436659 | 5559318 | 387563 | 3754356 | 645305 | 101338 | 28832177 | 109222 | 48407507 |
| L23-3 | 735277 | 5760257 | 319638 | 4475630 | 703218 | 103564 | 31377343 | 115452 | 44724429 |
| L24-1 | 1777357 | 8012344 | 352380 | 3874126 | 609498 | 225276 | 26484748 | 340073 | 49213231 |
| L24-2 | 501969 | 7244774 | 661042 | 3670596 | 678490 | 292612 | 30304249 | 164546 | 50288445 |
| L24-3 | 635488 | 8230494 | 384650 | 3114836 | 393381 | 236335 | 24689613 | 2304506 | 53769330 |
| L25-1 | 324777 | 8898574 | 455295 | 5531597 | 388537 | 385500 | 29962999 | 587963 | 62637549 |
| L25-2 | 444386 | 2778028 | 301497 | 5805260 | 159708 | 66936 | 12971979 | 357986 | 73770765 |
| L25-3 | 343173 | 4830665 | 400102 | 5464852 | 434476 | 152497 | 27235647 | 788859 | 53288640 |
| | | | | LCMS | | | | | |
| Non-responders | | | | | | | | | |
| L1-1 | 2857768 | 4863089 | 21185375 | 4200391 | 13766850 | 4975418 | 2218993 | 2537728 | 110255 |
| L1-2 | 2269148 | 6229920 | 22596055 | 3402335 | 15192714 | 6185157 | 1944324 | 2258641 | 88522 |
| L1-3 | 2917882 | 6533238 | 26659172 | 2182056 | 12935004 | 6529316 | 2276431 | 3189475 | 70718 |
| L5-1 | 1730395 | 7546622 | 19639125 | 1533600 | 9984660 | 9540604 | 3089826 | 2543528 | 64078 |
| L5-2 | 1964141 | 7273134 | 22439790 | 1610494 | 14119536 | 8919735 | 3344373 | 2578027 | 83540 |
| L5-3 | 1997837 | 7180643 | 18670255 | 1619283 | 14353396 | 9262397 | 2938968 | 2487579 | 81699 |
| L6-1 | 1036833 | 5537619 | 22303099 | 2073767 | 15591793 | 10674058 | 2145627 | 4286625 | 61105 |
| L6-2 | 768319 | 3590128 | 18311607 | 2077420 | 10549949 | 8433064 | 2248780 | 3647390 | 122651 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L6-3 | 1367667 | 5885056 | 19233409 | 1535330 | 10873056 | 10871604 | 2619686 | 2660881 | 174760 |
| L8-1 | 2461181 | 8184213 | 28534354 | 1942920 | 16283551 | 11266084 | 2648961 | 3312959 | 127089 |
| L8-2 | 2509241 | 7807937 | 26621704 | 2526189 | 15119236 | 9328414 | 2656370 | 3319684 | 106362 |
| L8-3 | 2248092 | 9658103 | 29195593 | 1544307 | 17141567 | 11602197 | 2767073 | 3628124 | 100139 |
| L9-1 | 1341492 | 9437560 | 22460448 | 1083898 | 10505067 | 11342188 | 2434592 | 2957653 | 99776 |
| L9-2 | 559249 | 11422498 | 16575741 | 2293762 | 13022814 | 11276671 | 1938267 | 1955163 | 134673 |
| L9-3 | 455105 | 10146740 | 21757946 | 950348 | 18244050 | 2610654 | 3537437 | 4147806 | 259294 |
| L10-1 | 2578441 | 7337271 | 22775697 | 1069560 | 11137878 | 12830190 | 2366278 | 2050243 | 115352 |
| L10-2 | 1843844 | 6378420 | 19843640 | 1338251 | 10116026 | 10532130 | 2301843 | 2139600 | 100845 |
| L10-3 | 1989483 | 6678047 | 22376391 | 1285801 | 11863891 | 11382182 | 2434008 | 2196156 | 123476 |
| L12-1 | 868152 | 6753790 | 24025391 | 1410683 | 12703066 | 7316486 | 3243572 | 2734993 | 98193 |
| L12-2 | 1120359 | 6118162 | 23608241 | 1796314 | 15295473 | 8639726 | 2833903 | 2658369 | 144211 |
| L12-3 | 284240 | 6299476 | 26728446 | 1272049 | 21304167 | 7374157 | 3146983 | 2893710 | 166766 |
| L17-1 | 3224093 | 7635827 | 23503138 | 1476161 | 12850020 | 10117955 | 2032475 | 2199363 | 103608 |
| L17-2 | 996502 | 6262543 | 23238507 | 1429615 | 11358273 | 8961346 | 2062731 | 2166240 | 109060 |
| L17-3 | 1888499 | 6182524 | 21140551 | 1348829 | 9523638 | 9029027 | 2080848 | 2240519 | 87271 |
| L19-1 | 2214523 | 10687626 | 21767204 | 1943797 | 13702408 | 7444685 | 3007759 | 1823222 | 128920 |
| L19-2 | 1499875 | 7218288 | 18493802 | 4034911 | 11330203 | 9034877 | 2529322 | 1395742 | 148693 |
| L19-3 | 938938 | 8978590 | 23930527 | 2777921 | 16468240 | 8077009 | 2654233 | 1671314 | 121730 |
| L22-1 | 1076096 | 5776936 | 17554705 | 4082698 | 19668285 | 8130330 | 2412677 | 2951586 | 133154 |
| L22-2 | 1736840 | 6564722 | 20986891 | 4302982 | 17029140 | 7856195 | 2387258 | 3327179 | 174356 |
| L22-3 | 2226363 | 6921065 | 23532930 | 3406845 | 19987645 | 6972376 | 2777039 | 3395602 | 178203 |

Responders

| | | | | | | | | | |
|---|---|---|---|---|---|---|---|---|---|
| L2-1 | 2353938 | 6971666 | 23397328 | 1999213 | 14492259 | 8011737 | 2082145 | 2546784 | 115525 |
| L2-2 | 2472325 | 7304923 | 24285859 | 1513644 | 12545882 | 8101450 | 2073921 | 2342282 | 133056 |
| L2-3 | 2518328 | 7798923 | 24061113 | 1912770 | 15356308 | 7623144 | 2226472 | 2194622 | 134331 |
| L3-1 | 2826030 | 6434338 | 22744227 | 1848880 | 11476680 | 10417090 | 2515310 | 2640486 | 95755 |
| L3-2 | 2755322 | 7406714 | 25541012 | 1335183 | 12264463 | 11465308 | 2435048 | 2378625 | 88415 |
| L3-3 | 2349339 | 7288452 | 25547197 | 1159106 | 12370246 | 10149476 | 2310744 | 2564720 | 115487 |
| L4-1 | 2304138 | 10281302 | 22330444 | 2213414 | 12280798 | 11580547 | 3768982 | 2622769 | 199469 |
| L4-2 | 1097584 | 9346346 | 21522578 | 2426769 | 15141166 | 10945857 | 3646668 | 2645906 | 158262 |
| L4-3 | 1326679 | 7061823 | 18675933 | 1352804 | 11735971 | 8240699 | 3513925 | 2260200 | 143341 |
| L7-1 | 1875249 | 4038418 | 20946119 | 1344890 | 6037609 | 6788997 | 5030384 | 4262493 | 131261 |
| L7-2 | 1538754 | 4708295 | 23830879 | 1821889 | 8325238 | 6436134 | 3788674 | 3723873 | 93062 |
| L7-3 | 1963815 | 5260479 | 27672014 | 1732983 | 8753494 | 10433752 | 3261182 | 3285735 | 95090 |
| L13-1 | 3314497 | 6803435 | 21344429 | 1986534 | 15609056 | 12749290 | 3698417 | 2323572 | 101591 |
| L13-2 | 2850843 | 8561291 | 21918049 | 1394638 | 18339206 | 15087078 | 4307383 | 2492912 | 108153 |
| L13-3 | 2558994 | 7925489 | 19352658 | 1651373 | 14105938 | 13506953 | 4516954 | 2514863 | 94305 |
| L15-1 | 2497707 | 8192411 | 21936911 | 931446 | 10796666 | 10443391 | 2394481 | 2135300 | 122512 |
| L15-3 | 2637626 | 7614355 | 23058093 | 1125286 | 12528730 | 9791897 | 2410673 | 1919940 | 186777 |
| L16-1 | 1627158 | 8295668 | 20308436 | 1855784 | 16443679 | 13043328 | 2720893 | 2426915 | 137905 |
| L16-2 | 1304829 | 8860909 | 22682890 | 2055997 | 18933228 | 9211137 | 2410079 | 2170831 | 92377 |
| L16-3 | 1967196 | 7189098 | 20209811 | 1534004 | 10081835 | 11194615 | 2818819 | 1929729 | 79334 |
| L18-1 | 2543946 | 7606624 | 24826576 | 1448641 | 12852178 | 10149618 | 2418828 | 2065973 | 108291 |
| L18-2 | 980716 | 6901476 | 23061093 | 1756262 | 13468879 | 9345759 | 2312561 | 2192421 | 138132 |
| L18-3 | 3419555 | 7396160 | 27286995 | 1512059 | 13637810 | 9704331 | 2382662 | 1911636 | 151913 |
| L21-1 | 1843192 | 8454037 | 22082447 | 1387624 | 11035296 | 10735959 | 3105413 | 2179067 | 88761 |
| L21-2 | 79770 | 10237848 | 25452718 | 1177620 | 12838131 | 11651540 | 3209321 | 2185788 | 115180 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| ID | 79 Asparagine | 80 Cystine | 81 Cystathionine | 84 Isoleucine | 85 Leucine | 86 Creatine | 87 asy-Dimethyl-arginine | 88 sym-Dimethyl-arginine | 90 2-Aminoisobutyric acid |
|---|---|---|---|---|---|---|---|---|---|
| L21-3 | 1999001 | 8810517 | 20349549 | | | | | | |
| L23-1 | 2247963 | 7890225 | 22918811 | | | | | | |
| L23-2 | 2050289 | 8208861 | 24967778 | | | | | | |
| L23-3 | 2643837 | 9081052 | 20672199 | | | | | | |
| L24-1 | 2463008 | 10750359 | 27440895 | | | | | | |
| L24-2 | 1614948 | 8117632 | 23078973 | | | | | | |
| L24-3 | 2603418 | 9297386 | 24889200 | | | | | | |
| L25-1 | 1034621 | 8528572 | 19823648 | | | | | | |
| L25-2 | 1776821 | 6288079 | 18139922 | | | | | | |
| L25-3 | 1609358 | 7860339 | 19484827 | | | | | | |

(continued)

| | | | | | 1786655 | 9103122 | 11241089 | 3495655 | 2205136 | 105687 |
| | | | | | 1507935 | 10701977 | 8545589 | 2364189 | 2097476 | 96486 |
| | | | | | 2191660 | 12664682 | 9735131 | 2122882 | 2042641 | 112223 |
| | | | | | 1647133 | 11467503 | 9512201 | 2323270 | 2092005 | 103877 |
| | | | | | 1479521 | 18658205 | 10430609 | 2685344 | 2014143 | 99027 |
| | | | | | 1508951 | 15103011 | 8392889 | 2856357 | 1867255 | 92389 |
| | | | | | 1485071 | 22072325 | 8455704 | 2507173 | 1890578 | 154326 |
| | | | | | 899257 | 16457158 | 12673559 | 3321898 | 1943271 | 154976 |
| | | | | | 1881498 | 9932733 | 11134355 | 3031985 | 2027332 | 166089 |
| | | | | | 1271280 | 11013005 | 12647609 | 3460925 | 2015559 | 145334 |

LCMS

Non-responders

| ID | 79 Asparagine | 80 Cystine | 81 Cystathionine | 84 Isoleucine | 85 Leucine | 86 Creatine | 87 asy-Dimethyl-arginine | 88 sym-Dimethyl-arginine | 90 2-Aminoisobutyric acid |
|---|---|---|---|---|---|---|---|---|---|
| L1-1 | 639573 | 3072155 | 18694 | 18858365 | 19951624 | 9737513 | 361641 | 347714 | 391268 |
| L1-2 | 638455 | 2400197 | 18072 | 22377068 | 17249577 | 5480494 | 365658 | 331823 | 93658 |
| L1-3 | 514168 | 1913270 | 6680 | 22843320 | 19139753 | 4122114 | 351884 | 403073 | 131464 |
| L3-1 | 344117 | 1305039 | 18398 | 21330403 | 19694880 | 5819456 | 304971 | 468481 | 178909 |
| L5-1 | 456370 | 1572467 | 28044 | 17669772 | 17008420 | 5082549 | 305587 | 486204 | 147001 |
| L5-2 | 441996 | 1480138 | 24301 | 18278686 | 15302635 | 4571072 | 295680 | 376967 | 187499 |
| L5-3 | 677032 | 3001153 | 9970 | 16251244 | 13161375 | 12645898 | 526539 | 431016 | 157327 |
| L6-1 | 697472 | 3235815 | 11441 | 12622611 | 11697476 | 7764321 | 456909 | 414470 | 139822 |
| L6-2 | 537566 | 3476995 | 11216 | 11386842 | 9378922 | 9996160 | 471910 | 551295 | 123558 |
| L6-3 | 682941 | 3026912 | 18072 | 19647590 | 11601220 | 6406880 | 468793 | 464518 | 212701 |
| L8-1 | 794608 | 3265396 | 20406 | 21093843 | 14128679 | 6603481 | 479194 | 557010 | 373151 |
| L8-2 | 697668 | 2892455 | 20255 | 19368853 | 15530938 | 6604314 | 447429 | 534395 | 230620 |
| L8-3 | 676713 | 2623308 | 47404 | 22328679 | 17030717 | 7519038 | 465734 | 515137 | 260392 |
| L9-1 | 600062 | 2221183 | 79468 | 25062328 | 23382342 | 15897702 | 469432 | 426286 | 143525 |
| L9-2 | 1442695 | 3194432 | 275542 | 19205563 | 17763360 | 98695089 | 509029 | 1018646 | 198152 |
| L9-3 | 678875 | 2801262 | 5607 | 9543142 | 10484902 | 9330874 | 309956 | 395915 | 191030 |
| L10-1 | 466573 | 2551193 | 3737 | 12105824 | 9548264 | 9939383 | 292703 | 346819 | 166608 |
| L10-2 | 561636 | 3225278 | 7475 | 10983601 | 8153472 | 8205789 | 315918 | 440482 | 155065 |
| L10-3 | 685823 | 2362090 | 30222 | 15062514 | 12222781 | 10854422 | 398885 | 515234 | 234321 |
| L12-1 | 577464 | 1871378 | 37024 | 18613843 | 15626678 | 11246160 | 421587 | 476624 | 222782 |
| L12-2 | 740333 | 2800831 | 51864 | 15219949 | 13855002 | 6746104 | 412632 | 485042 | 187069 |
| L12-3 | 595333 | 1991851 | 9035 | 13081561 | 10980333 | 6917293 | 296561 | 278361 | 238116 |
| L17-1 | 551271 | 1375060 | 3115 | 12418359 | 10616649 | 8368770 | 260570 | 308750 | 205241 |
| L17-2 | 434166 | 1781371 | 5641 | 12918085 | 11587667 | 9958328 | 278083 | 300354 | 227242 |
| L19-1 | 767392 | 2943723 | 20251 | 15799605 | 15546783 | 10093263 | 293458 | 281701 | 161425 |
| L19-2 | 478633 | 2605149 | 26794 | 17261570 | 16176980 | 19285693 | 255554 | 225669 | 135743 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L19-3 | 813062 | 2027945 | 28507 | 14782534 | 12263428 | 13032889 | 276838 | 274846 | 189372 |
| L22-1 | 501754 | 3209646 | 21495 | 20079715 | 17851273 | 5683076 | 466738 | 309164 | 206593 |
| L22-2 | 587794 | 3429778 | 32403 | 17550825 | 15466100 | 6207462 | 457142 | 337328 | 237224 |
| L22-3 | 702240 | 4458666 | 18694 | 18193291 | 14713319 | 5980480 | 420750 | 403349 | 285310 |
| Responders | | | | | | | | | |
| L2-1 | 533197 | 2796282 | 7771 | 17092572 | 12798288 | 9696442 | 375499 | 359071 | 189982 |
| L2-2 | 541777 | 3299841 | 8100 | 14566065 | 13180305 | 10586686 | 348237 | 369505 | 138752 |
| L2-3 | 720021 | 3523102 | 17777 | 16158245 | 12988696 | 13367882 | 352424 | 379103 | 162626 |
| L3-1 | 483407 | 2171920 | 4049 | 11704381 | 10634410 | 8557601 | 431588 | 529659 | 203229 |
| L3-2 | 658119 | 1974680 | 4430 | 10258909 | 8597907 | 6529177 | 394856 | 442933 | 183260 |
| L3-3 | 717713 | 2719388 | 4051 | 11590034 | 11165699 | 9825696 | 400977 | 487862 | 237772 |
| L4-1 | 617788 | 5107160 | 62943 | 24946851 | 20099090 | 24162699 | 395368 | 727743 | 311172 |
| L4-2 | 561941 | 4537963 | 52566 | 18129816 | 14186205 | 11451807 | 407257 | 662251 | 223783 |
| L4-3 | 286089 | 3104734 | 33961 | 18276268 | 16220227 | 12180647 | 451514 | 701404 | 183288 |
| L7-1 | 395075 | 3400601 | 48302 | 10391634 | 8589328 | 2135560 | 524430 | 1027970 | 125853 |
| L7-2 | 394728 | 3463587 | 46743 | 11199113 | 7346185 | 2469149 | 620287 | 969198 | 113037 |
| L7-3 | 427139 | 3704820 | 20181 | 11329226 | 7891947 | 1745002 | 541958 | 801877 | 97969 |
| L13-1 | 537090 | 4169608 | 16512 | 16020290 | 13059355 | 3360168 | 409741 | 444563 | 197535 |
| L13-2 | 573858 | 4567446 | 16306 | 17301086 | 15585455 | 3224237 | 455237 | 499040 | 129693 |
| L13-3 | 652257 | 3888573 | 27418 | 20368410 | 17276188 | 3401098 | 429258 | 476196 | 142221 |
| L15-1 | 667733 | 2875536 | 1869 | 12653662 | 12289038 | 7781829 | 340581 | 472774 | 116024 |
| L15-3 | 734757 | 3577029 | 15580 | 10915320 | 8342328 | 4392937 | 283119 | 371545 | 98078 |
| L16-1 | 512680 | 4157376 | 21809 | 13607805 | 12245353 | 4822126 | 330907 | 378794 | 110913 |
| L16-2 | 509878 | 3166038 | 13605 | 15882068 | 13741057 | 3870849 | 313908 | 319187 | 151077 |
| L16-3 | 285634 | 3297541 | 5521 | 14252965 | 14093917 | 4392682 | 368323 | 421540 | 112177 |
| L18-1 | 631702 | 3153202 | 8725 | 14127192 | 11407551 | 4425771 | 336662 | 390788 | 135157 |
| L18-2 | 660360 | 4340602 | 21082 | 12567835 | 10517964 | 4998198 | 372036 | 448197 | 133389 |
| L18-3 | 775649 | 4093172 | 19628 | 11327234 | 9559514 | 4581343 | 334821 | 398242 | 173962 |
| L21-1 | 752746 | 2722885 | 12722 | 17880508 | 16219415 | 7828324 | 424958 | 453452 | 223135 |
| L21-2 | 1070586 | 5511960 | 10592 | 17033328 | 14329104 | 6028600 | 394683 | 446480 | 160679 |
| L21-3 | 533865 | 2497337 | 21502 | 22868255 | 19642298 | 11580605 | 454596 | 499538 | 240515 |
| L23-1 | 585112 | 3333414 | 6853 | 12903542 | 10238639 | 2252339 | 308559 | 252848 | 129406 |
| L23-2 | 958749 | 3323634 | 27105 | 15029544 | 12897225 | 3599661 | 360562 | 284491 | 133534 |
| L23-3 | 677649 | 2546773 | 6126 | 14829020 | 13755072 | 4654731 | 403578 | 272328 | 109801 |
| L24-1 | 764861 | 3231391 | 10592 | 16982628 | 15654023 | 6570167 | 372330 | 375766 | 197136 |
| L24-2 | 640927 | 2616602 | 13484 | 17629087 | 15723162 | 5985955 | 346489 | 292738 | 231877 |
| L24-3 | 916514 | 4816921 | 12773 | 12709176 | 11468725 | 5918543 | 355364 | 328191 | 260220 |
| L25-1 | 610537 | 2941258 | 81651 | 16763678 | 15974577 | 17933985 | 428416 | 808390 | 190588 |
| L25-2 | 351512 | 2551326 | 44936 | 9470149 | 7757846 | 9951749 | 268144 | 485872 | 94175 |
| L25-3 | 492131 | 3517326 | 51721 | 15564001 | 11223771 | 13114088 | 338411 | 562717 | 191215 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | LCMS | | | | | |
|---|---|---|---|---|---|---|---|---|---|
| ID | 93 Thyroxine | 96 Hippurate | 101 Citric acid | 102 Isocitric acid | 103 Succinic acid | 106 2-Hydroxy-butyric acid | 107 3-Hydroxy-butyric acid | 110 Lactic acid | 113 2-Hydroxy-butyric acid |
| Non-responders | | | | | | | | | |
| L1-1 | 5719 | 285619 | 10469068 | 179125 | 180227 | 2554639 | 2040863 | 843460 | 36214 |
| L1-2 | 1341 | 241125 | 6690191 | 107865 | 157823 | 659626 | 380013 | 650344 | 31931 |
| L1-3 | 8211 | 63993 | 9086266 | 121972 | 282399 | 746407 | 944872 | 989048 | 37037 |
| L5-1 | 8449 | 75258 | 9788549 | 143178 | 228402 | 1075156 | 1184257 | 1060789 | 41410 |
| L5-2 | 15083 | 243517 | 10520717 | 96188 | 243556 | 829493 | 260545 | 1003679 | 46121 |
| L5-3 | 12931 | 185324 | 8672904 | 135330 | 197399 | 643666 | 156281 | 816427 | 47884 |
| L6-1 | 13255 | 194039 | 7714078 | 100211 | 331241 | 844022 | 440354 | 2360299 | 62430 |
| L6-2 | 4698 | 1528100 | 9180017 | 141590 | 289145 | 743930 | 5186765 | 1692825 | 54239 |
| L6-3 | 4986 | 489396 | 11750066 | 170498 | 487294 | 890978 | 2897830 | 1885182 | 60233 |
| L8-1 | 10613 | 536002 | 11296713 | 110184 | 223980 | 671172 | 1146805 | 781948 | 83838 |
| L8-2 | 7602 | 814423 | 11788709 | 108843 | 210741 | 1570230 | 6683571 | 940117 | 79753 |
| L8-3 | 14469 | 1080230 | 13484559 | 188873 | 253879 | 695112 | 1184542 | 793568 | 113018 |
| L9-1 | 13568 | 47705 | 7854913 | 53702 | 210584 | 1811225 | 405222 | 956824 | 63834 |
| L9-2 | 4927 | 161161 | 7232555 | 180631 | 209839 | 1413856 | 550698 | 1294270 | 68529 |
| L9-3 | 2691 | 798284 | 23360033 | 493881 | 465298 | 6169858 | 5829404 | 2961318 | 445578 |
| L10-1 | 13527 | 191685 | 13614817 | 106532 | 218847 | 1124865 | 5971263 | 623316 | 50340 |
| L10-2 | 4193 | 123180 | 14500171 | 129710 | 284077 | 1228451 | 4099879 | 984800 | 50311 |
| L10-3 | 14622 | 753984 | 20051176 | 139059 | 292283 | 959311 | 4767227 | 1029544 | 60445 |
| L12-1 | 3026 | 136892 | 14412344 | 212870 | 565579 | 1785530 | 4378676 | 1068263 | 208585 |
| L12-2 | 4653 | 303395 | 15501949 | 268502 | 712524 | 1596971 | 4839394 | 1404216 | 167362 |
| L12-3 | 3499 | 147339 | 12661598 | 166896 | 866453 | 1751360 | 1357354 | 1684995 | 231586 |
| L17-1 | 17460 | 45633 | 11687715 | 114754 | 235409 | 1016285 | 3247999 | 754008 | 52154 |
| L17-2 | 12588 | 47275 | 12033510 | 132438 | 402475 | 1033128 | 4777066 | 1219422 | 57695 |
| L17-3 | 18946 | 33641 | 11119308 | 98254 | 254917 | 1503028 | 4102634 | 1068897 | 58684 |
| L19-1 | 13499 | 563303 | 5922418 | 57436 | 209468 | 845734 | 378223 | 974398 | 47273 |
| L19-2 | 15005 | 319674 | 4094416 | 64697 | 138611 | 727545 | 394925 | 862680 | 39527 |
| L19-3 | 11522 | 703643 | 4215610 | 42670 | 151429 | 816193 | 247501 | 1061845 | 63857 |
| L21-1 | 2322 | 166291 | 6955434 | 47267 | 196849 | 1412645 | 663311 | 1722101 | 39682 |
| L22-2 | 16652 | 216829 | 8573839 | 160443 | 181593 | 1823917 | 1264876 | 1165590 | 34117 |
| L22-3 | 13362 | 515059 | 11077133 | 160500 | 219110 | 1692121 | 2068501 | 1067169 | 37463 |
| Responders | | | | | | | | | |
| L2-1 | 9042 | 1040222 | 9663139 | 106662 | 198465 | 1242131 | 1853822 | 1015600 | 30921 |
| L2-2 | 17560 | 197708 | 9411674 | 72368 | 220272 | 1063446 | 2350900 | 720976 | 32868 |
| L2-3 | 8461 | 834034 | 9424072 | 86117 | 256576 | 1018492 | 684625 | 901677 | 41624 |
| L3-1 | 14085 | 1071791 | 14295237 | 135430 | 364161 | 1176024 | 5106335 | 975293 | 64626 |
| L3-2 | 17999 | 975510 | 10857183 | 99516 | 273279 | 938638 | 2266958 | 547446 | 51473 |
| L3-3 | 16374 | 554197 | 10338872 | 118431 | 419458 | 1281659 | 2517898 | 975466 | 38847 |
| L4-1 | 12504 | 1060673 | 8133796 | 149104 | 272944 | 1274469 | 5602794 | 885765 | 109640 |
| L4-2 | 4898 | 1447138 | 6293673 | 110004 | 212216 | 855603 | 340608 | 1339782 | 92651 |
| L4-3 | 12619 | 2026047 | 8297411 | 155037 | 379066 | 729896 | 471937 | 2062602 | 96242 |

TABLE 1-continued

L number represents patient number. With respect to numbers appearing after hyphen (-), "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| ID | 114<br>2-Hydroxy-<br>isovaleric<br>acid | 115<br>3-Hydroxy<br>isovaleric<br>acid | 116<br>Glyceric<br>acid | 117<br>Malic<br>acid | 119<br>Betaine | 120<br>Urea | 123<br>Uric acid | 124<br>Acetylglycine | 125<br>4-Hydroxy-<br>proline |
|---|---|---|---|---|---|---|---|---|---|
| | | | | | LCMS | | | | |
| L7-1 | 6790 | 920341 | 12223209 | 232782 | 177716 | 1242709 | 8673561 | 936883 | 81670 |
| L7-2 | 7731 | 951916 | 12895672 | 303639 | 253623 | 1128794 | 4496302 | 1112756 | 96107 |
| L7-3 | 5617 | 1470317 | 12204460 | 103299 | 172719 | 716297 | 6872551 | 930015 | 60848 |
| L13-1 | 9849 | 768394 | 14690519 | 168253 | 278169 | 706521 | 2955595 | 974855 | 50362 |
| L13-2 | 15811 | 4727813 | 17092720 | 210537 | 301734 | 434070 | 599195 | 710041 | 50577 |
| L13-3 | 15865 | 3939357 | 15351766 | 205476 | 293740 | 486118 | 1232230 | 870515 | 40238 |
| L15-1 | 9658 | 1206696 | 7039486 | 86557 | 194503 | 272585 | 435928 | 417350 | 42141 |
| L15-2 | 10648 | 1334361 | 9052101 | 72550 | 204761 | 263736 | 1487392 | 488015 | 48045 |
| L15-3 | 21143 | 143197 | 5932881 | 116098 | 147381 | 492387 | 243715 | 835230 | 37555 |
| L16-1 | 17164 | 467633 | 7807973 | 139234 | 120366 | 842360 | 309104 | 1397393 | 50920 |
| L16-2 | 20227 | 307236 | 8365564 | 105072 | 176691 | 641360 | 990644 | 767876 | 54020 |
| L16-3 | 8241 | 393654 | 9629961 | 96041 | 191588 | 680640 | 3237746 | 560551 | 36953 |
| L18-1 | 10110 | 418220 | 8794138 | 81007 | 206472 | 784653 | 3470526 | 603104 | 33506 |
| L18-2 | 10704 | 371227 | 9750881 | 91987 | 181185 | 640752 | 1709888 | 488418 | 37538 |
| L18-3 | 15607 | 142738 | 7674965 | 76349 | 234904 | 875487 | 3748510 | 698542 | 38208 |
| L21-2 | 16892 | 139836 | 7820060 | 84155 | 285007 | 729233 | 932515 | 482232 | 40737 |
| L21-3 | 12502 | 156845 | 7885505 | 89806 | 221228 | 1367339 | 2214783 | 698599 | 39702 |
| L23-1 | 17599 | 472392 | 11074857 | 112929 | 212725 | 422093 | 2280823 | 633904 | 39061 |
| L23-2 | 15933 | 1113642 | 10114429 | 109561 | 237522 | 710720 | 2427161 | 931595 | 32219 |
| L23-3 | 19522 | 1048297 | 12139920 | 114244 | 240155 | 662253 | 2261554 | 1079201 | 47157 |
| L24-1 | 15317 | 226246 | 10718973 | 99091 | 226008 | 582377 | 473950 | 685139 | 44563 |
| L24-2 | 12162 | 72431 | 8767533 | 94456 | 210100 | 1358593 | 1554016 | 808307 | 37805 |
| L24-3 | 10202 | 350871 | 8586907 | 73553 | 244575 | 728360 | 41841 | 697152 | 40522 |
| L25-1 | 4995 | 5093276 | 7357545 | 147369 | 260677 | 665690 | 548271 | 1125214 | 124507 |
| L25-2 | 19463 | 802120 | 6140534 | 131854 | 176361 | 309350 | 412961 | 521084 | 70491 |
| L25-3 | 12137 | 1133199 | 6520556 | 124323 | 269613 | 463691 | 607638 | 487154 | 52126 |
| Non-responders | | | | | | | | | |
| L1-1 | 493262 | 247768 | 89447 | 67966 | 19876112 | 30942378 | 5714105 | 298601 | 1127871 |
| L1-2 | 327425 | 230344 | 76188 | 41832 | 19021326 | 32982641 | 7985108 | 261739 | 1667863 |
| L1-3 | 354112 | 191529 | 87665 | 58494 | 20255851 | 27684604 | 6557308 | 495379 | 1709840 |
| L5-1 | 476993 | 215971 | 1028968 | 50328 | 28950098 | 28896969 | 4910770 | 394715 | 2743027 |
| L5-2 | 702603 | 254520 | 121869 | 62278 | 36467657 | 27384857 | 11179127 | 302400 | 2930698 |
| L5-3 | 506082 | 156568 | 92619 | 56820 | 27209713 | 25191624 | 4494569 | 274308 | 2233171 |
| L6-1 | 183280 | 386480 | 137775 | 105368 | 23783250 | 26341137 | 4165674 | 609482 | 1454953 |
| L6-2 | 186798 | 526738 | 140187 | 96550 | 27066076 | 20408214 | 3645449 | 538468 | 1607407 |
| L6-3 | 147272 | 319120 | 117208 | 151744 | 26987245 | 23189234 | 4642882 | 521998 | 2035974 |
| L8-1 | 796159 | 185782 | 75519 | 79994 | 15269241 | 29674552 | 3608102 | 447362 | 2654352 |
| L8-2 | 1968661 | 252919 | 68977 | 97457 | 11028666 | 40982629 | 7493591 | 511966 | 2220649 |
| L8-3 | 1233881 | 182693 | 76523 | 101229 | 14615414 | 39364220 | 6189220 | 420057 | 3042073 |
| L9-1 | 502194 | 126424 | 80943 | 72202 | 21260649 | 38881595 | 1429821 | 493200 | 1742748 |

TABLE 1-continued

L number represents patient number. With respect to numbers appearing after hyphen (-). "1" represents "pretreatment"; "2" represents "after the 1st treatment"; and "3" represents "after the 2nd treatment". Metabolite values for 145 items of "pretreatment", "after the 1st treatment" and "after the 2nd treatment" of each patient were shown, as classified into "non-responder" and "responder" groups.

| | | | | | | | |
|---|---|---|---|---|---|---|---|
| L9-2 | 393616 | 135887 | 97294 | 16539348 | 39435855 | 1673252 | 360241 | 1522481 |
| L9-3 | 857232 | 327855 | 199537 | 336406 | 10696407 | 36581583 | 3237160 | 2271916 | 2476083 |
| L10-1 | 331327 | 38767 | 60289 | 52521 | 30039378 | 28421287 | 7657408 | 360136 | 2189185 |
| L10-2 | 503230 | 112937 | 62424 | 87000 | 31100525 | 30872607 | 7792098 | 295887 | 1794162 |
| L10-3 | 377883 | 63435 | 80393 | 100476 | 30336547 | 26704009 | 9828832 | 359957 | 2262464 |
| L12-1 | 879251 | 184938 | 107077 | 156552 | 24577770 | 35586522 | 6733072 | 1056718 | 2833042 |
| L12-2 | 1272619 | 157483 | 96961 | 205001 | 21303476 | 36755760 | 9123662 | 1143820 | 3577704 |
| L12-3 | 2536034 | 169228 | 108456 | 208358 | 26756186 | 37141236 | 17980621 | 564223 | 4271549 |
| L17-1 | 224572 | 81388 | 62930 | 71419 | 32209275 | 23669601 | 4247981 | 257798 | 2275611 |
| L17-2 | 287975 | 84856 | 57438 | 106202 | 29962848 | 23739347 | 3472374 | 347216 | 2119984 |
| L17-3 | 326855 | 103646 | 73594 | 30367 | 34382197 | 26927820 | 4590203 | 477733 | 1339075 |
| L19-1 | 335252 | 193188 | 70684 | 37286 | 31081174 | 37088284 | 11751064 | 343690 | 3024310 |
| L19-2 | 364362 | 157119 | 56476 | 19148 | 32674968 | 34810026 | 7357449 | 266821 | 2073094 |
| L19-3 | 336824 | 133121 | 52284 | 37739 | 24062926 | 31157790 | 8105632 | 220942 | 2294714 |
| L22-1 | 421109 | 120722 | 93945 | 71490 | 29004772 | 32080969 | 8101221 | 251946 | 2239557 |
| L22-2 | 328967 | 100908 | 84863 | 58906 | 33762564 | 32961610 | 9188049 | 244354 | 1686889 |
| L22-3 | 469934 | 102774 | 84823 | 74291 | 31669275 | 31691038 | 16893088 | 256517 | 1594303 |
| Responders | | | | | | | | |
| L2-1 | 308617 | 84944 | 73139 | 42569 | 33792634 | 27830826 | 9436971 | 306815 | 1474650 |
| L2-2 | 485466 | 102287 | 63843 | 49071 | 33405044 | 31694135 | 8785948 | 322378 | 1408047 |
| L2-3 | 484690 | 96347 | 62972 | 50923 | 29567931 | 30992410 | 10609844 | 289142 | 2534020 |
| L3-1 | 227496 | 85265 | 90462 | 122396 | 18871022 | 29181857 | 4206093 | 709500 | 1918440 |
| L3-2 | 182938 | 73539 | 52540 | 76717 | 17641394 | 25884483 | 5178546 | 502014 | 1812143 |
| L3-3 | 220006 | 86903 | 60331 | 107502 | 20620677 | 26025871 | 5402931 | 660636 | 1789126 |
| L4-1 | 359710 | 268682 | 68869 | 132530 | 25787703 | 42734394 | 11881647 | 557945 | 3135543 |
| L4-2 | 324925 | 201412 | 72044 | 100414 | 23016628 | 34255074 | 13404750 | 391273 | 2700510 |
| L4-3 | 311714 | 194081 | 91735 | 109424 | 21636340 | 41057219 | 9040360 | 685768 | 1404251 |
| L7-1 | 477986 | 302775 | 98143 | 68793 | 15069763 | 30806219 | 6491191 | 352797 | 1926249 |
| L7-2 | 468212 | 248879 | 89888 | 142779 | 13719419 | 26595791 | 5921014 | 383356 | 2054402 |
| L7-3 | 613188 | 145050 | 73306 | 97227 | 16146076 | 26524367 | 10073128 | 374406 | 2479676 |
| L13-1 | 230799 | 126326 | 89519 | 95871 | 31037344 | 29698058 | 8180246 | 471943 | 2518159 |
| L13-2 | 256515 | 109843 | 95299 | 83459 | 31870286 | 36943128 | 10687771 | 486116 | 3097062 |
| L13-3 | 287861 | 129874 | 101257 | 76447 | 35544816 | 41632172 | 11803355 | 532022 | 3307624 |
| L15-1 | 219731 | 121395 | 66491 | 51254 | 28461311 | 42043914 | 5705830 | 691054 | 1478948 |
| L15-2 | 298776 | 114759 | 50797 | 44641 | 36225425 | 36241052 | 14833162 | 686158 | 1374581 |
| L15-3 | 444167 | 91704 | 84046 | 27266 | 28556773 | 35563052 | 10933587 | 327199 | 3271317 |
| L16-1 | 427993 | 93575 | 76520 | 46385 | 34914895 | 31182019 | 3909507 | 307873 | 3064835 |
| L16-2 | 475489 | 108032 | 85956 | 34860 | 34399998 | 29122332 | 6626778 | 379819 | 2365428 |
| L18-1 | 367439 | 111468 | 67196 | 53502 | 27964947 | 25103942 | 9914478 | 199654 | 2535034 |
| L18-2 | 753073 | 103689 | 67545 | 45400 | 23609724 | 28052985 | 15834081 | 235500 | 1954296 |
| L18-3 | 317265 | 87041 | 48548 | 38349 | 25106092 | 25183781 | 9472198 | 253150 | 2202653 |
| L21-1 | 350473 | 147967 | 60977 | 59909 | 17992761 | 42848457 | 5793472 | 898241 | 1366463 |

TABLE 1-continued

| | | | | | | |
|---|---|---|---|---|---|---|
| L21-2 | 601763 | 119358 | 58175 | 39517 | 42050706 | 17683370 | 11118833 | 697365 | 2166829 |
| L21-3 | 354679 | 185598 | 65215 | 47397 | 36814358 | 16689542 | 6253599 | 634835 | 1768190 |
| L23-1 | 360682 | 129848 | 69243 | 68825 | 28644584 | 54598628 | 7258477 | 652754 | 1900345 |
| L23-2 | 403637 | 213564 | 66270 | 62755 | 34213018 | 37006925 | 9742423 | 412196 | 2455697 |
| L23-3 | 305537 | 146986 | 80248 | 64744 | 31446570 | 42451213 | 4097647 | 504613 | 2579759 |
| L24-1 | 435775 | 75586 | 78306 | 77452 | 28926015 | 35677402 | 8844273 | 393177 | 2749461 |
| L24-2 | 702286 | 57830 | 76885 | 63414 | 29160644 | 33251255 | 7882466 | 218234 | 2150975 |
| L24-3 | 787182 | 50288 | 71045 | 63324 | 29005525 | 29694500 | 15345310 | 317416 | 1808609 |
| L25-1 | 462515 | 338090 | 73459 | 104192 | 26051595 | 10234933 | 7950502 | 654218 | 1692160 |
| L25-2 | 189063 | 188741 | 97641 | 53616 | 40060635 | 24799414 | 10041969 | 579059 | 1407783 |
| L25-3 | 234222 | 118986 | 78917 | 60057 | 44034155 | 20030415 | 11583888 | 657679 | 2506901 |

L number represents patient number. With respect to numbers appearing after hyphen (-), "1" represents "pretreatment"; "2" represents "after the 1st treatment"; and "3" represents "after the 2nd treatment", Metabolite values for 145 items of "pretreatment", "after the 1st treatment" and "after the 2nd treatment" of each patient were shown, as classified into "non-responder" and "responder" groups.

TABLE 2

Out of the individual metabolite items shown in Table 1, items which showed a significant difference (p < 0.05) in Mann-Whitney U test were extracted from "Pre-treatment" items, "2 weeks after 1st Nivolumab" items and "2 weeks after 2nd Nivolumab" items.

| Metabolites showing p-value < 0.05 in our analysis | High or low in responders | P-value (Mann-Whitney U test) |
|---|---|---|
| Pre-treatment | | |
| Hippurate | High | 0.0101 |
| Indoxyl sulfate | High | 0.0499 |
| Uric acid | High | 0.0356 |
| Aminoadipic acid | low | 0.0101 |
| 2 weeks after 1st Nivolumab | | |
| Gluconic acid | High | 0.0037 |
| Cystine | High | 0.0101 |
| Thyroxine | High | 0.0127 |
| Indoxyl sulfate | High | 0.0428 |
| 3-Methyl-2-oxobutyric acid | low | 0.0015 |
| Nicotinamide | low | 0.0294 |
| 2-Aminoethanol | low | 0.0356 |
| Lactic acid | low | 0.0429 |
| 2 weeks after 2nd Nivolumab (4 weeks after 1st Nivolumab) | | |
| Ornithine | High | 0.0089 |
| Cystine | High | 0.0499 |
| 4-Cresol | High | 0.0258 |
| Decanoic acid | High | 0.0499 |
| Pyruvic acid | low | 0.0090 |
| 2-Hydroxybutyric acid | low | 0.0111 |
| 2-Oxoglutaric acid | low | 0.0249 |
| Pyroglutamic acid | low | 0.0299 |
| Lactic acid | low | 0.0169 |

REFERENCE

1. Roy S, Trinchieri G. Microbiota: a key orchestrator of cancer therapy. Nature reviews Cancer 2017, 17(5): 271-285.
2. Sivan A, Corrales L, Hubert N, Williams J B, Aquino-Michaels K, Earley Z M, et al. Commensal *Bifidobacterium* promotes antitumor immunity and facilitates anti-PD-L1 efficacy. Science 2015, 350(6264): 1084-1089.
3. Vetizou M, Pitt J M, Daillere R, Lepage P, Waldschmitt N, Flament C, et al. Anticancer immunotherapy by CTLA-4 blockade relies on the gut microbiota. Science 2015,
4. Leslie M. Gut Microbes May Up PD-1 Inhibitor Response. Cancer Discov 2017, 7(5): 448-448.
5. Williams H R, Cox I J, Walker D G, Cobbold J F, Taylor-Robinson S D, Marshall S E, et al. Differences in gut microbial metabolism are responsible for reduced hippurate synthesis in Crohn's disease. BMC gastroenterology 2010, 10: 108.
6. Li M, Wang B, Zhang M, Rantalainen M, Wang S, Zhou H, et al. Symbiotic gut microbes modulate human metabolic phenotypes. Proceedings of the National Academy of Sciences of the U.S. Pat. No. 2,008,105(6): 2117-2122.
7. Borghaei H, Paz-Ares L, Horn L, Spigel D R, Steins M, Ready N E, et al. Nivolumab versus Docetaxel in Advanced Nonsquamous Non-Small-Cell Lung Cancer. The New England journal of medicine 2015, 373(17): 1627-1639.

All publications, patents and patent applications cited herein are incorporated herein by reference in their entirety.

INDUSTRIAL APPLICABILITY

By using the biomarkers of the present invention, the efficacy of therapy with a PD-1 signal inhibitor can be judged before or at an early stage of the therapy. As a result, the efficiency of therapy can be improved while reducing its cost.

The invention claimed is:

1. A method of therapy for a cancer in a subject in need thereof, the method comprising
    administering a first dose of a PD-1 signal inhibitor to the subject, wherein the PD-1 signal inhibitor is an antibody selected from the group consisting of anti-PD-1 antibody, anti-PD-L1 antibody and anti-PD-L2 antibody,
    detecting in the subject at least one difference, relative to a non-responder, in a peripheral blood concentration of an energy metabolism-related metabolite or an intestinal flora-related metabolite, wherein said non-responder is a patient with cancer who has progressive disease (PD) according to the RECIST classification within 3 months after administering a first dose of the PD-1 signal inhibitor, and
    treating the subject by administering a of the PD-1 signal inhibitor to the subject if the at least one difference is detected,
    wherein the at least one difference is selected from the group consisting of:
    a higher level in a peripheral blood concentration of hippurate before administering the first dose of the PD-1 signal inhibitor to the subject and the non-responder,
    a higher level in a peripheral blood concentration of indoxyl sulfate before administering the first dose of the PD-1 signal inhibitor to the subject and the non-responder,
    a higher level in a peripheral blood concentration of uric acid before administering the first dose of the PD-1 signal inhibitor to the subject and the non-responder,
    a lower level in a peripheral blood concentration of aminoadipic acid before administering the first dose of the PD-1 signal inhibitor to the subject and the non-responder,
    a higher level in a peripheral blood concentration of gluconic acid after administering the first dose of the PD-1 signal inhibitor to the subject and the non-responder,
    a higher level in a peripheral blood concentration of cystine after administering the first dose of the PD-1 signal inhibitor to the subject and the non-responder,
    a higher level in a peripheral blood concentration of thyroxine after administering the first dose of the PD-1 signal inhibitor to the subject and the non-responder,
    a higher level in a peripheral blood concentration of indoxyl sulfate after administering the first dose of the PD-1 signal inhibitor to the subject and the non-responder,
    a lower level in a peripheral blood concentration of 3-methyl-2-oxobutyric acid after administering the first dose of the PD-1 signal inhibitor to the subject and the non-responder,
    a lower level in a peripheral blood concentration of nicotinamide after administering the first dose of the PD-1 signal inhibitor to the subject and the non-responder,
    a lower level in a peripheral blood concentration of 2-aminoethanol after administering the first dose of the PD-1 signal inhibitor to the subject and the non-responder, and a lower level in a peripheral blood concentration of lactic acid after administering the first dose of the PD-1 signal inhibitor to the subject and the non-responder.

2. The method according to claim 1, wherein the antibody is nivolumab.

3. The method according to claim 1, wherein one of the at least one difference before administering the first dose of the PD-1 signal inhibitor to the subject and the non-responder is detected in combination with another one of the at least one difference after administering the first dose of the PD-1 signal inhibitor to the subject and the non-responder.

4. The method according to claim 1, wherein the at least one difference comprises the higher level in a peripheral blood concentration of hippurate before administering the first dose to the subject and the non-responder.

5. The method according to claim 1, wherein the at least one difference comprises the higher level in a peripheral blood concentration of indoxyl sulfate before administering the first dose to the subject and the non-responder.

6. The method according to claim 1, wherein the at least one difference comprises the higher level in a peripheral blood concentration of uric acid before administering the first dose to the subject and the non-responder.

7. The method according to claim 1, wherein the at least one difference comprises the lower level in a peripheral blood concentration of aminoadipic acid before administering the first dose to the subject and the non-responder.

8. The method according to claim 1, wherein the at least one difference comprises the higher level in a peripheral blood concentration of gluconic acid after administering the first dose to the subject and the non-responder.

9. The method according to claim 1, wherein the at least one difference comprises the higher level in a peripheral blood concentration of cystine after administering the first dose to the subject and the non-responder.

10. The method according to claim 1, wherein the at least one difference comprises the higher level in a peripheral blood concentration of thyroxine after administering the first dose to the subject and the non-responder.

11. The method according to claim 1, wherein the at least one difference comprises the higher level in a peripheral blood concentration of indoxyl sulfate after administering the first dose to the subject and the non-responder.

12. The method according to claim 1, wherein the at least one difference comprises the lower level in a peripheral blood concentration of 3-methyl-2-oxobutyric acid after administering the first dose to the subject and the non-responder.

13. The method according to claim 1, wherein the at least one difference comprises the lower level in a peripheral blood concentration of nicotinamide after administering the first dose to the subject and the non-responder.

14. The method according to claim 1, wherein the at least one difference comprises the lower level in a peripheral blood concentration of 2-aminoethanol after administering the first dose to the subject and the non-responder.

15. The method according to claim 1, wherein the at least one difference comprises the lower level in a peripheral blood concentration of lactic acid after administering the first dose to the subject and the non-responder.

16. A method of therapy for a cancer in a subject in need thereof, the method comprising
detecting in the subject at least one difference, relative to a non-responder, in peripheral blood concentration of an energy metabolism-related metabolite or an intestinal flora-related metabolite, wherein said non-responder is a patient with cancer who has progressive disease (PD) according to the RECIST classification within 3 months after administering a first dose of a PD-1 signal inhibitor, and
administering a therapeutically effective amount of the PD-1 signal inhibitor to the subject if the at least one difference is detected, wherein the PD-1 signal inhibitor is an antibody selected from the group consisting of anti-PD-1 antibody, anti-PD-L1 antibody and anti-PD-L2 antibody,
wherein the at least one difference is selected from the group consisting of:
a higher level in a peripheral blood concentration of hippurate,
a higher level in a peripheral blood concentration of indoxyl sulfate,
a higher level in a peripheral blood concentration of uric acid, and
a lower level in a peripheral blood concentration of aminoadipic acid.

17. A method of therapy for a cancer in a subject in need thereof, the method comprising
administering a first dose of a PD-1 signal inhibitor to the subject,
administering a second dose of the PD-1 signal inhibitor to the subject two weeks after the first dose, wherein the PD-1 signal inhibitor is an antibody selected from the group consisting of anti-PD-1 antibody, anti-PD-L1 antibody and anti-PD-L2 antibody,
detecting in the subject at least one first difference, relative to a non-responder, in a peripheral blood concentration of an energy metabolism-related metabolite or an intestinal flora-related metabolite, wherein said non-responder is a patient with cancer who has progressive disease (PD) according to the RECIST classification within 3 months after administering a first dose of a PD-1 signal inhibitor, and
administering an additional dose of the PD-1 signal inhibitor to the subject two weeks after the second dose if the at least one first difference is detected,
wherein the first difference is selected from the group consisting of:
a higher level in a peripheral blood concentration of ornithine after administering the second dose of the PD-1 signal inhibitor to the subject and the non-responder,
a higher level in a peripheral blood concentration of cystine after administering the second dose of the PD-1 signal inhibitor to the subject and the non-responder,
a higher level in a peripheral blood concentration of 4-cresol after administering the second dose of the PD-1 signal inhibitor to the subject and the non-responder,
a higher level in a peripheral blood concentration of decanoic acid after administering the second dose of the PD-1 signal inhibitor to the subject and the non-responder,
a lower level in a peripheral blood concentration of pyruvic acid after administering the second dose of the PD-1 signal inhibitor to the subject and the non-responder,
a lower level in a peripheral blood concentration of 2-hydroxybutyric acid after administering the second dose of the PD-1 signal inhibitor to the subject and the non-responder, a lower level in a peripheral blood concentration of 2-oxoglutaric acid after administering the second dose of the PD-1 signal inhibitor to the subject and the non-responder, a lower level in a peripheral blood concentration of pyroglutamic acid after administering the second dose of the PD-1 signal inhibitor to the subject and the non-responder, and a lower level in a peripheral blood concentration of lactic acid after administering the second dose of the PD-1 signal inhibitor to the subject and the non-responder.

18. The method according to claim 17, further detecting at least one second difference, relative a non-responder, in a peripheral blood concentration of an energy metabolism-related metabolite or an intestinal flora-related metabolite, wherein the second difference is selected from the group consisting of:

a higher level in a peripheral blood concentration of hippurate before administering the first dose of the PD-1 signal inhibitor to the subject and the non-responder, a higher level in a peripheral blood concentration of indoxyl sulfate before administering the first dose of the PD-1 signal inhibitor to the subject and the non-responder, a higher level in a peripheral blood concentration of uric acid before administering the first dose of the PD-1 signal inhibitor to the subject and the non-responder, a lower level in a peripheral blood concentration of aminoadipic acid before administering the first dose of the PD-1 signal inhibitor to the subject and the non-responder, a higher level in a peripheral blood concentration of gluconic acid after administering the first dose of the PD-1 signal inhibitor to the subject and the non-responder, a higher level in a peripheral blood concentration of cystine after administering the first dose of the PD-1 signal inhibitor to the subject and the non-responder, a higher level in a peripheral blood concentration of thyroxine after administering the first dose of the PD-1 signal inhibitor to the subject and the non-responder, a higher level in a peripheral blood concentration of indoxyl sulfate after administering the first dose of the PD-1 signal inhibitor to the subject and the non-responder, a lower level in a peripheral blood concentration of 3-methyl-2-oxobutyric acid after administering the first dose of the PD-1 signal inhibitor to the subject and the non-responder, a lower level in a peripheral blood concentration of nicotinamide after administering the first dose of the PD-1 signal inhibitor to the subject and the non-responder, a lower level in a peripheral blood concentration of 2-aminoethanol after administering the first dose of the PD-1 signal inhibitor to the subject and the non-responder, and a lower level in a peripheral blood concentration of lactic acid after administering the first dose of the PD-1 signal inhibitor to the subject and the non-responder.

* * * * *